(12) United States Patent
Dobbs

(10) Patent No.: US 8,350,655 B2
(45) Date of Patent: Jan. 8, 2013

(54) SHIELDED POWER COUPLING DEVICE

(75) Inventor: John M. Dobbs, Beverly, MA (US)

(73) Assignee: Analogic Corporation, Peabody, MA (US)

( * ) Notice: Subject to any disclaimer, the term of this patent is extended or adjusted under 35 U.S.C. 154(b) by 1036 days.

(21) Appl. No.: 11/699,529

(22) Filed: Jan. 29, 2007

(65) Prior Publication Data

US 2007/0188284 A1   Aug. 16, 2007

Related U.S. Application Data

(63) Continuation-in-part of application No. 10/787,270, filed on Feb. 26, 2004, now Pat. No. 7,868,723.

(60) Provisional application No. 60/450,038, filed on Feb. 26, 2003.

(51) Int. Cl.
*H01F 21/06* (2006.01)
*H01F 27/02* (2006.01)
*H01F 27/36* (2006.01)
*H01F 21/04* (2006.01)

(52) U.S. Cl. ....... 336/130; 336/83; 336/84 C; 336/84 R; 336/115; 336/120; 336/121; 336/131; 336/132; 336/133; 336/134; 336/135; 336/136

(58) Field of Classification Search ............ 336/65, 336/83, 84 C, 84 R, 115, 120, 121, 130–136
See application file for complete search history.

(56) References Cited

U.S. PATENT DOCUMENTS 2,958,057 A * 10/1960 Berman .................. 336/135
3,336,662 A    8/1967 Howland et al.
3,999,093 A * 12/1976 Kirtley, Jr. ................ 310/198
4,145,591 A    3/1979 Takeda
4,259,654 A    3/1981 Persson et al.
4,293,884 A   10/1981 Schiller (Continued)

FOREIGN PATENT DOCUMENTS

CA    20022434479 A1   10/2002

(Continued)

OTHER PUBLICATIONS

Crepaz et al. The Reduction of the External Electromagnetic Field Produced by Reactors and Inductors for Power Electronics, ICEM, 1986, pp. 419-423.

(Continued)

*Primary Examiner* — Mohamad Musleh
*Assistant Examiner* — Tsz Chan
(74) *Attorney, Agent, or Firm* — McDermott Will & Emery LLP

(57) ABSTRACT

Axisymmetric solid of revolution derivable from section at FIG. 5 is generally toroidal with electric current(s) in windings 110, 160 preferably flowing circumferentially along major circle(s) during power coupling device operation. Current(s) in windings 110, 160; current(s) in half-shields 120, 170; and the volume of space swept out by shield airgap(s) 101 emerge from plane of paper perpendicularly at FIG. 5 but as these emerge therefrom they curve to follow toroidal major circle(s). Cores 115, 165 preferably shunt and align magnetic flux such that magnetic field lines escape therefrom primarily only in region(s) of core airgap(s) and such that magnetic flux loops lie in planes of toroidal minor circle(s). Half-shield(s) 120, 170 preferably have electrically conductive material(s) distributed therein as is sufficient to substantially cancel magnetic flux lines impinging thereon before effects of such impinging magnetic flux lines would reach shield airgap(s) 101 and/or outer surface(s) of half-shields 120, 170.

58 Claims, 23 Drawing Sheets

U.S. PATENT DOCUMENTS

| | | | |
|---|---|---|---|
| 4,323,781 A | 4/1982 | Baumann et al. | |
| 4,335,423 A | 6/1982 | Koizumi et al. | |
| 4,496,202 A | 1/1985 | Beckmann et al. | |
| 4,564,812 A | 1/1986 | Van Dijk | |
| 4,725,781 A | 2/1988 | Roschmann | |
| 4,785,246 A | 11/1988 | Sugimoto | |
| 4,798,540 A | 1/1989 | Bernardi | |
| 4,912,735 A * | 3/1990 | Beer | 378/15 |
| 5,023,768 A * | 6/1991 | Collier | 363/68 |
| 5,105,095 A | 4/1992 | Rudy et al. | |
| 5,191,309 A | 3/1993 | Laros | |
| 5,296,810 A | 3/1994 | Morich | |
| 5,414,360 A | 5/1995 | Westphal et al. | |
| 5,499,281 A | 3/1996 | Weedon et al. | |
| 5,512,828 A | 4/1996 | Pausch et al. | |
| 5,530,425 A | 6/1996 | Harrison | |
| 5,570,073 A | 10/1996 | Muller | |
| 5,572,129 A | 11/1996 | Carlson | |
| 5,572,178 A * | 11/1996 | Becker et al. | 336/120 |
| 5,608,771 A * | 3/1997 | Steigerwald et al. | 378/15 |
| 5,717,552 A * | 2/1998 | Varian | 360/125.01 |
| 5,827,445 A | 10/1998 | Yoshida et al. | |
| 5,841,067 A | 11/1998 | Nakamura et al. | |
| 5,939,882 A | 8/1999 | Gebhardt et al. | |
| 5,986,531 A | 11/1999 | Carrozzi | |
| 6,015,476 A * | 1/2000 | Schlueter et al. | 156/345.46 |
| 6,058,000 A | 5/2000 | Koenck et al. | |
| 6,160,869 A | 12/2000 | Zapalac et al. | |
| 6,236,209 B1 | 5/2001 | Arz et al. | |
| 6,239,361 B1 | 5/2001 | Snaper | |
| 6,256,175 B1 | 7/2001 | Zhang | |
| 6,326,788 B1 | 12/2001 | Mulder et al. | |
| 6,346,816 B1 | 2/2002 | Damadian et al. | |
| 6,351,123 B1 | 2/2002 | Gebhardt | |
| 6,351,626 B1 | 2/2002 | Lohr | |
| 6,373,921 B1 | 4/2002 | Kliman et al. | |
| 6,388,548 B1 * | 5/2002 | Saito et al. | 336/90 |
| 6,407,470 B1 | 6/2002 | Seelig | |
| 6,437,571 B1 | 8/2002 | Danby et al. | |
| 6,448,500 B1 | 9/2002 | Hosaka et al. | |
| 6,469,508 B1 | 10/2002 | Damadian et al. | |
| 6,496,007 B1 | 12/2002 | Damadian et al. | |
| 6,501,016 B1 | 12/2002 | Sosnowski | |
| 6,576,877 B2 | 6/2003 | Dabelstein et al. | |
| 6,590,305 B2 | 7/2003 | Wang et al. | |
| 6,590,391 B1 | 7/2003 | Shudo et al. | |
| 6,590,953 B2 | 7/2003 | Suzuki et al. | |
| 6,617,852 B1 | 9/2003 | Danby et al. | |
| 6,636,406 B1 | 10/2003 | Anthony | |
| 6,653,924 B2 | 11/2003 | Vinciarelli et al. | |
| 6,687,108 B1 | 2/2004 | Anthony et al. | |
| 6,713,737 B1 | 3/2004 | Verhagen | |
| 6,762,088 B2 | 7/2004 | Acosta et al. | |
| 6,794,792 B2 | 9/2004 | Wang | |
| 6,839,401 B2 | 1/2005 | Nokita | |
| 2004/0000974 A1 | 1/2004 | Odenaal et al. | |
| 2005/0030013 A1 * | 2/2005 | Terada et al. | 324/207.25 |
| 2005/0140483 A1 | 6/2005 | Wobben | |
| 2006/0022785 A1 | 2/2006 | Dobbs | |
| 2006/0208727 A1 | 9/2006 | Matsumoto | |

FOREIGN PATENT DOCUMENTS

| | | |
|---|---|---|
| DE | 10 2004 035603 A1 | 3/2006 |
| DE | 10 2004 051170 A1 | 5/2006 |
| EP | 926690 A1 * | 6/1999 |
| GB | 0990418 B1 | 4/1965 |
| JP | 61020308 A * | 1/1986 |
| JP | 63192212 A * | 8/1988 |
| JP | 01123406 | 5/1989 |
| JP | 2211123 A1 | 8/1990 |
| JP | 06181124 | 6/1994 |
| JP | 08051039 | 2/1996 |
| JP | 8335511 A1 | 12/1996 |
| JP | 11354346 | 12/1999 |
| JP | 2000114077 | 4/2000 |
| JP | 2002198238 | 7/2002 |
| JP | 2003114203 A1 | 4/2003 |
| JP | 2004166923 A1 | 6/2004 |
| WO | WO2006008274 A1 | 1/2006 |

OTHER PUBLICATIONS

Miyoshi et al. Reduction of Magnetic Flux Leakage From an Induction Heating Range, IEEE Transactions on Industry Applications, vol. 1A-19, No. 4, Jul./Aug. 1983.

Pedder et al. A Contactless Electrical Energy Transmission System, IEEE Transactions on Industrial Electronics, vol. 46, No. 1, Feb. 1999.

Williamson Labs, http://www.williamson-labs.com/480_shi.htm.

International Search Report for corresponding PCT Application No. PCT/US08/52326, 2 pp.

Written Opinion for corresponding PCT Application No. PCT/US08/52326, 10 pp.

Supplementary European Search Report dated Jan. 3, 2011 from correspondingEuropean Application No. 08728478.2.

* cited by examiner

SHIELDED POWER COUPLING DEVICE

CROSS-REFERENCE TO RELATED APPLICATIONS

This application is a continuation-in-part application claiming benefit of priority under 35 USC 120 from commonly owned U.S. patent application Ser. No. 10/787,270, filed 26 Feb. 2004 now U.S. Pat. No. 7,868,723, entitled "Power Coupling Device," now pending, which in turn claims benefit of priority under 35 USC 119(e) from U.S. Provisional Application Ser. No. 60/450,038, entitled "Non-Contacting Power Coupling Device," filed 26 Feb. 2003, now expired; moreover, the content of said application Ser. No. 10/787,270 and the content of said Provisional Application Ser. No. 60/450,038 are hereby incorporated herein by reference in their entireties.

FEDERALLY SPONSORED RESEARCH

Not applicable.

NAMES OF PARTIES TO JOINT RESEARCH AGREEMENT

Not applicable.

INCORPORATION BY REFERENCE OF MATERIAL ON COMPACT DISC

Not applicable.

FIELD

The present disclosure relates to a shielded power coupling device; more particularly, relates to a shielded power coupling device capable of reducing radio frequency (RF) emission and/or other electromagnetic interference, reducing leakage inductance, and/or improving efficiency during inductive transfer of electric power in the context, for example, of a computed tomography (CT) scanner such as might be used in medical or security applications or the like, or in the context of other such applications where transfer of electric power between or among bodies capable of engaging in relative rotation is desired.

BACKGROUND

When power coupling devices are used to inductively transfer electric power in noncontact fashion, e.g., from stationary subsystems to rotating subsystems in medical CT scanners or the like, it is often desired that such power coupling devices be shielded. Lack of adequate shielding may, for example, result in undesirable RF emission, increased leakage inductance, and/or reduced power transfer efficiency. Moreover, where power is being transferred between or among bodies capable of engaging in relative rotation, it may be impossible or impractical to employ an unbroken Faraday cage or other such integral shield that would completely surround the power coupling device, it being instead necessary to employ a shield that only partially encloses the power coupling device or to divide such shield into multiple parts split so as to form gap(s) permitting relative rotation between or among such bodies.

SUMMARY

In accordance with one aspect of the present invention, a shielded power coupling device is designed to reduce radio frequency (RF) emission and/or other electromagnetic interference, reduce leakage inductance, and/or improve efficiency during inductive transfer of electric power in the context, for example, of a computed tomography (CT) scanner such as might be used in medical or security applications or the like, or in the context of other such applications where transfer of electric power between or among bodies capable of engaging in relative rotation is desired. For example, shielded power coupling device(s) in accordance with embodiment(s) of the present invention might to be used to transfer power of on the order of 2.5 kW or more as might be required to operate a CT scanner employed in a security-related application or the like; or, shielded power coupling device(s) in accordance with embodiment(s) of the present invention might to be used to transfer power of on the order of 25 kW or more as might be required to operate a CT scanner employed in a medical application or the like.

An axisymmetric solid of revolution derivable from cross-sectional profile shown at FIG. 5 is generally toroidal with electric current(s) in windings 110, 160 preferably flowing circumferentially, e.g., along toroid major circle(s), during power coupling device operation. Current(s) in windings 110, 160; current(s) in shield(s) 120, 170; and the volume of space swept out by airgap(s) 101 during operation of the shielded power coupling device emerge from the plane of the paper perpendicularly at FIG. 5 but as these emerge therefrom they curve to follow toroid major circle(s). Shield(s) 120, 170 may be, for example, two-part wraparound shield(s) comprising half-shields 120, 170 having shield airgap(s) adjacent to core airgap(s); it is alternatively or additionally possible to employ any suitable shield configuration, including, without limitation, the following configurations: single-part, multipartite, adjacent-airgap, nonadjacent-airgap, cutback, wraparound, and so forth. Cores 115, 165 preferably shunt and align magnetic flux such that magnetic field lines escape therefrom primarily only in region(s) of core airgap(s) and such that magnetic flux loops linking respective cores 115, 165 lie in meridional planes, e.g., planes of toroid minor circles(s). Half-shield(s) 120, 170 preferably have electrically conductive material(s) distributed therein as is sufficient to permit flow of electric current(s) such as will induce magnetic field (s) capable of substantially canceling magnetic flux lines impinging thereon before effects of such impinging magnetic flux lines would reach shield airgap(s) 101 and/or outer surface(s) of half-shields(s) 120, 170; e.g., before electric current(s) induced in half-shield(s) 120, 170 by such impinging flux lines would be conducted to shield airgap(s) 101 and/or outer surface(s) of half-shields(s) 120, 170.

In a representative meridional section of one embodiment such as is shown in FIG. 5, field-canceling currents flowing in half-shields(s) 120, 170; currents flowing in windings 110, 160; and volumes of space swept out by shield airgap(s) 101 are all preferably substantially mutually parallel; moreover, lines of aligned magnetic flux linking cores 115, 165 are substantially perpendicular to field-canceling currents flowing in half-shields(s) 120, 170; to currents flowing in windings 110, 160; and to imaginary surfaces bounding volumes of space swept out by shield airgap(s) 101. That is, magnetic field(s) preferably have no substantial component parallel to an imaginary surface bounding the volume of space swept out by shield airgap(s) 101 during operation of the power coupling device, and the net current(s) flowing in half-shields(s) 120, 170 preferably have no component perpendicular to an imaginary surface bounding the volume of space swept out by shield airgap(s) 101 during operation of the power coupling device. That is, fringing field(s) 103 preferably do not have a component which would tend to cause induced electric currents to cross shield airgap(s) 101.

Half-shield(s) 120, 170 preferably have electrically conductive material(s) at such location(s), in such distribution(s), and in such electrical conductivity or conductivities and thickness(es) as is sufficient to permit flow of electric current (s) such as will induce magnetic field(s) capable of substantially canceling magnetic flux lines impinging thereon before effects of such impinging magnetic flux lines would reach shield airgap(s) 101 and/or outer surface(s) of half-shields(s) 120, 170; e.g., before electric current(s) induced in half-shield(s) 120, 170 by such impinging flux lines would be conducted to outer surface(s) of half-shield(s) 120, 170. More preferably, half-shield(s) 120, 170 comprise electrically conductive material(s) forming substantially continuous electrical path(s) constituting closed electric circuit(s) around the axis of rotation, e.g., circumferential path(s) along circle(s) coaxial with major circle(s) of the toroidal volume occupied by the overall axisymmetric structure. More preferably, such continuous electrical path(s) are capable of supporting electric current(s) sufficient to induce magnetic field(s) such as will substantially cancel magnetic field(s) due to electric current(s) flowing in windings 110, 160 during operation of the power coupling device.

This being the case, it is therefore preferred in one or more embodiments of the present invention that half-shield(s) 120, 170 have, adjacent to core airgap(s), fringe field canceling zone(s) of thickness(es) and electrical conductivity or conductivities sufficient to substantially cancel fringing fields due to magnetic flux emanating from core airgap(s) before effects of such emanating magnetic flux would reach shield airgap(s) 101 and/or outer surface(s) of half-shields(s) 120, 170; e.g., before electric currents produced thereby in half-shield(s) 120, 170 would be conducted to outer surface(s) of half-shield(s) 120, 170. It is furthermore preferred that, where present, such fringe field canceling zone(s) comprise electrically conductive material forming substantially continuous electrical path(s) constituting closed electric circuit(s) around the axis of rotation, e.g., circumferential path(s) along circle (s) coaxial with major circle(s) of the toroidal volume occupied by the overall axisymmetric structure. It is still furthermore preferred that continuous electrical path(s) at fringe field canceling zone(s), where present, be capable of supporting electric current(s) sufficient to induce magnetic field(s) capable of substantially canceling magnetic field(s) due to electric current(s) flowing in windings 110, 160 during operation of the power coupling device.

It is furthermore preferred that arrangement of windings 110, 160 and/or distribution of reluctance-lowering material at cores 115, 165 be such as to align magnetic flux such that magnetic flux loops lie in meridional planes, e.g., planes of minor circle(s) where the overall axisymmetric structure is more or less toroidal. It is furthermore preferred in one or more embodiments of the present invention that E-cores or the like having multiple core recesses be employed so as to permit a net instantaneous current in the primary windings of substantially zero (i.e., such that respective magnetization currents at respective primary windings mutually cancel). It is furthermore preferred, especially where core(s) 115, 165 comprise a multiplicity of core segments, that there be minimal interruption to axisymmetry, e.g., due to arrangement, including spacing, of core segments, or due to manner in which winding lead wire(s) enter and/or exit core recess(es); e.g., passageway(s) are preferably employed. It is furthermore preferred that winding lead wire(s), for example, pass through core(s) in such fashion and at such location(s) as will substantially eliminate or minimize formation of virtual current loop(s).

BRIEF DESCRIPTION OF DRAWINGS

These and other features, aspects, and advantages of the present invention will become better understood with regard to the following description, appended claims, and accompanying drawings where:

DETAILED DESCRIPTION

The present disclosure relates to a shielded power coupling device; more particularly, to a shielded power coupling device capable of reducing RF emission and/or other electromagnetic interference, reducing leakage inductance, and/or improving efficiency during inductive transfer of electric power in the context, for example, of a computed tomography (CT) scanner such as might be used in medical or security applications or the like, or in the context of other such applications where transfer of electric power between or among bodies capable of engaging in relative rotation is desired.

As used herein, the terms "electromagnetic interference," "radio frequency (RF) emission," and the like can in their most general senses include interference from surrounding equipment as it affects operation of power coupling device(s) in accordance with embodiment(s) of the present invention, but such terms are especially intended to refer to interference generated by power coupling device(s) in accordance with embodiment(s) of the present invention, particularly as it would affect sensitive electronic equipment such as might comprise portion(s) of CT scanner(s) or such as might be used in conjunction with CT scanner(s) or other such system(s) in the context of which power coupling device(s) in accordance with embodiment(s) of the present invention may be used.

Although the singular may be used herein for convenience in introducing terms such as "body," "object," "stator," "rotor," "airgap," "shield," "core," "winding," "center," "axis," etc., a similar situation will of course exist, and the present invention should be understood to in general be applicable, where plurality or pluralities of one or more of such features is or are present. Conversely, where plurality or pluralities are discussed, this is not to necessarily exclude the singular. Also, with regard to usage of prepositions "between" and "among," except where otherwise clear from context, use of "between" is not intended to necessarily imply limitation to two objects, and use of "among" is not intended to necessarily imply limitation to more than two objects.

Note that the term "noncontact" is used herein to refer to the ability to transfer power in inductive fashion between or among bodies capable of relative rotation, and should not be understood to necessarily preclude possible contact between or among such bodies for other purposes, including, e.g., electrostatic discharge, exchange or transmission of data, mechanical drive or support, braking and safety mechanisms, low-voltage power transfer, or even high-voltage power transfer such as might be desired in addition to power transferred inductively by of the types of power coupling device(s) disclosed herein.

Figure 1:
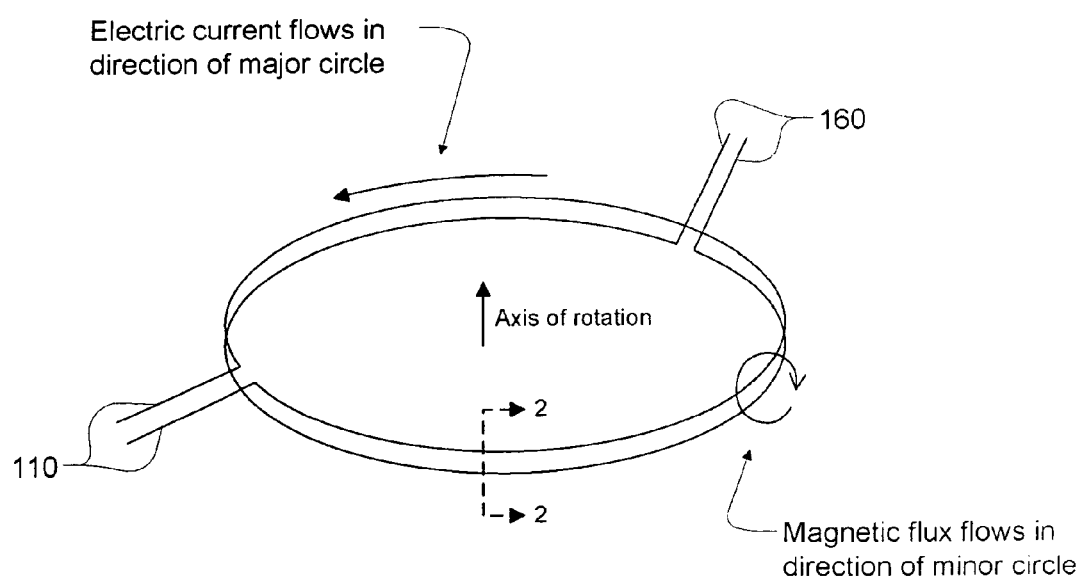
FIG. 1 is a perspective view of two windings 110, 160 in close mutual proximity, the windings 110, 160 being centered on an axis of rotation and lying in mutually parallel planes that are more or less perpendicular to the axis of rotation, which is to say that windings 110, 160 are coaxial with the axis of rotation.

Referring to FIG. 1, two more or less circular coils of more or less equal diameter comprising electrically conductive wire or the like (hereinafter "windings") 110, 160 are shown in close mutual proximity, these windings 110, 160 being centered on an axis of rotation and lying in mutually parallel planes that are more or less perpendicular to the axis of rotation, which is to say that windings 110, 160 are coaxial with the axis of rotation. If a torus is imagined that is centered on the axis of rotation and that has major radius equal to the radius of curvature of the windings, flow of electric current along a major circle of the torus will cause flow of loops of magnetic flux along minor circles of the torus in accordance with the so-called right hand rule (if wire is grasped with right hand such that thumb points in direction of electric current flow, induced magnetic flux will be in direction of curl of fingers around wire). Note that no attempt has been made in the drawings to accurately portray the sense or sign of current or flux flow, i.e., forward/backward or clockwise/counterclockwise, the intention here only being to indicate paths respectively traversed by electric current on the one hand and magnetic flux on the other; furthermore, where the electric current flowing therethrough is an alternating electric current, direction of current and flux flow will alternate in time-varying fashion, but no attempt has been made to portray this as well. Note that, except where otherwise clear from context, "current(s)" as used herein refers to alternating electric current(s).

Single-turn windings 110, 160 are shown, but either or both of these windings 110, 160 may instead have multiple turns or fractional turn(s) ("fractional turn" meaning a turn of less than 360° or having such a fractional remainder in addition to a single turn or multiple turns). Where windings 110, 160 are in relative rotation with respect to each other, a frame of reference may be imagined such that one of the windings appears to be stationary, in which case the assembly can be viewed as having a stationary side (e.g., at winding 110) and a rotating side (e.g., at winding 160) with an airgap therebetween to allow for relative motion.

Note that in the present specification, except where otherwise clear from context, the terms "gap" and "airgap" are used more or less interchangeably; although the term "airgap" may be used herein, as this should be understood to be mere deference to convention, it should be understood that such gaps are not limited to air, it being possible for vacuum, oil, and/or other fluid, and/or sliding and/or roller bearings or other such contrivance(s) permitting relative movement to completely or partially fill such space(s).

For example, in applications where power must be transferred to or from a rotating part, instead of, or in addition to, using sliding or rubbing contact(s) (e.g., brush(es) or the like) for electrical connection between stationary and rotating sides, it may be convenient to employ such a pair of windings, making electrical connection to stationary electronic circuitry via the stationary side, making electrical connection to rotating electronic circuitry via the rotating side, and transferring power across the airgap therebetween by mutual induction after the fashion of a transformer. In such a case, the two windings 110, 160 will be mutually inductively coupled by magnetic flux lines such that when an oscillating electric current is applied to one of the windings an electromotive force appears on the other of the windings.

Figure 2:
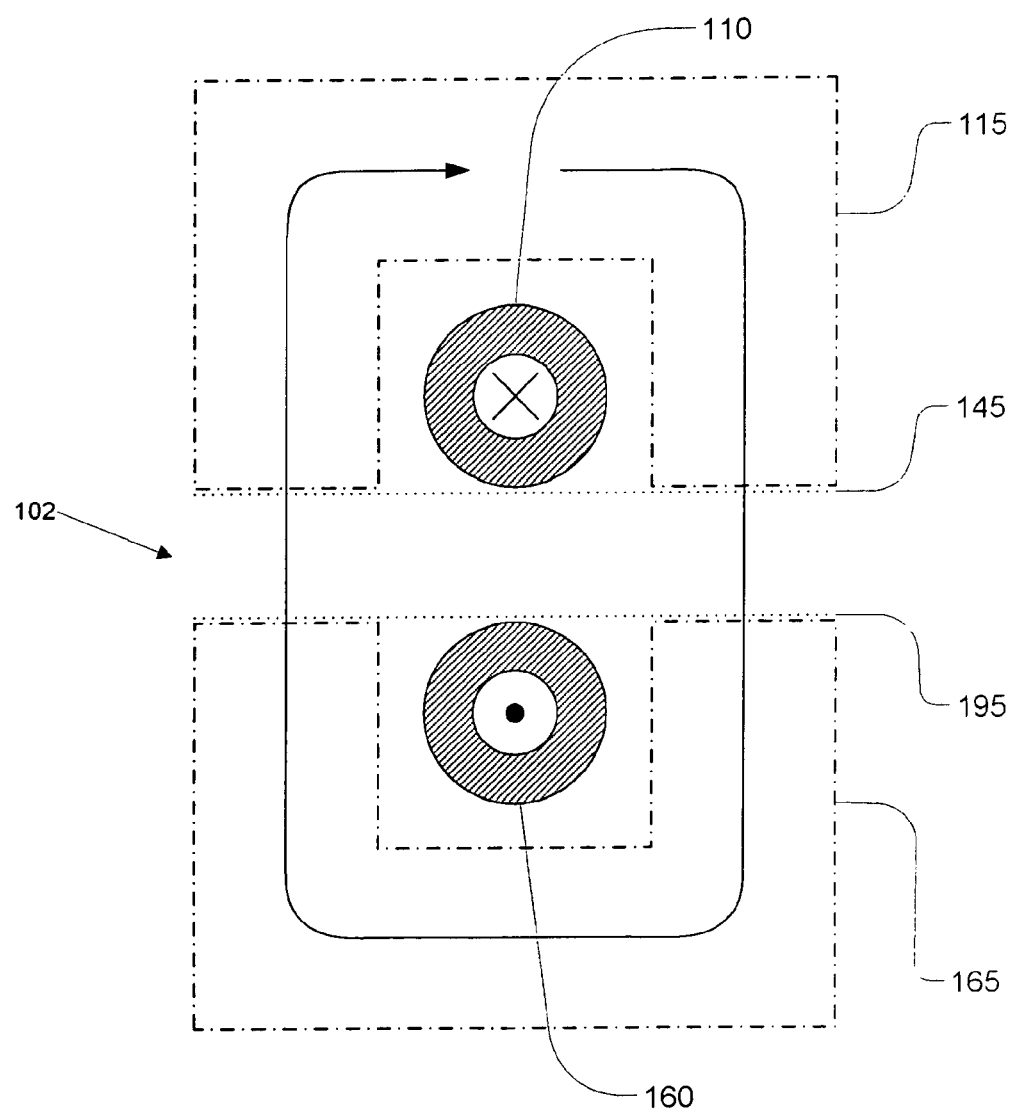
FIG. 2 is a sectional view of windings 110, 160 shown in FIG. 1, to which has been added in broken line the outline of a reluctance-lowering distribution of material 115, 165 improving mutual inductive coupling between windings 110, 160 by lowering reluctance of the path taken by magnetic flux lines mutually linking windings 110, 160.

Referring now to FIG. 2, this is a sectional view of windings 110, 160 shown in FIG. 1, to which has been added in broken line the outline of C-shaped ferromagnetic half-cores 115, 165 or other such reluctance-lowering distribution of material improving mutual inductive coupling between windings 110, 160 by lowering reluctance of the path taken by magnetic flux lines mutually linking windings 110, 160. Stating this another way, a toroidal shell of ferrite (an electrically nonconductive ferromagnetic ceramic material) or the like might be placed around windings 110, 160 in order to increase coupling therebetween; and where it is desired that the two windings 110, 160 be capable of moving with respect to each other, it will be convenient if this ferrite shell is split to allow movement between the one half-core which is fixed to the stationary winding 110 and the other half-core which moves with the rotating winding 160. In such case, the path taken by a loop of magnetic flux mutually linking the two windings 110, 160 will have two segments through ferrite and two segments through air.

Note that as used herein, terms such as "half-couple," "half-shell," "half-core," "half-shield," and the like are used as shorthand to refer to one of multiple (e.g., two) parts making up a whole constituting an inductive couple, shell, or the like, and as such should not be interpreted overly literally to mean that there must be exactly two such components or that such components must be of equal size, volume, mass, or the like; nor should similar implication that there must be exactly two such components be drawn from use of the term "couple." Rather, as used herein, except where otherwise clear from context, such terms should be understood to be representative of the more general case in which multiple parts may make up such a whole. Note that the term "rotary transformer half-couple" is used herein to refer to structure on one or the other side (primary or secondary) of a rotary transformer that is not itself a functioning rotary transformer, as distinct from the combined structure of both the primary and secondary sides that together constitute a functioning rotary transformer. Furthermore, especially with respect to half-cores and half-shields, the prefix "half-" may sometimes be omitted for convenience of description.

With respect to use of the term "core," this term is used herein to refer generally to reluctance-lowering (alternatively described as magnetically permeable) material, without regard to arrangement of such material in relation to a winding or the like. That is, whereas the term "core" might be narrowly interpreted to suggest that such reluctance-lowering material should be axially oriented or centrally located within the turn(s) of a winding as might be the case in a conventional transformer, the term is used herein out of deference to convention despite employment in embodiments in which rotary transformers may have so-called reverse topology in which core material is distributed in more or less toroidal fashion to reinforce magnetic flux loops in planes of toroid minor circles around windings wound in the direction of toroid major circles.

With continued reference to FIG. 2, if stationary winding 110 is, for example, connected to an alternating current (AC) power source after the fashion of a transformer primary winding, rotating winding 160, to which a load may be connected, may serve as transformer secondary winding. In such a rotary transformer, primary winding(s) may serve as inductive field generating element(s), secondary winding(s) may serve as inductive coupling field receiving element(s), and reluctance-lowering material(s) may serve as inductive coupling efficiency increasing element(s). Note that as used herein, the term "transformer" refers to apparatuses transferring power by mutual induction without regard to whether reluctance-decreasing material is present, without regard to the presence or relative amount of any leakage inductance, and without regard to whether the ratio of the number of turns on one side (i.e., primary or secondary side, or side which is above or below airgap 102 in FIG. 2) to the number of turns on the other side is such as to make power transfer step-up, step-down, or one-to-one, i.e., such as to make electromotive forces at respective windings be in ratio that is step-up, step-down, or one-to-one.

With continued reference to FIG. 2, such a rotary transformer structure would in this case comprise primary (e.g., stationary) winding 110, secondary (e.g., rotating) winding 160, primary core (e.g., ferrite half-core) 115, secondary core (e.g., ferrite half-core) 165, and airgap 102 which allows secondary winding 160 and secondary core 165 to rotate with respect to primary winding 110 and primary core 115. In the description given with reference to FIG. 2, note that even where half-cores are meant, the prefix "half-" may sometimes be omitted for convenience of description. FIG. 2 is a meridional section (also referred to as "radial section") through the more or less axisymmetric toroidal structure formed by the windings and core half-shells. Because FIG. 2 is derived from what may be referred to as the "stacked" or "axially displaced" winding arrangement shown in FIG. 1 in which there are two windings of more or less equal radius, the resulting more or less axisymmetric toroidal structure would have an axis of axisymmetry that is vertical as viewed in FIG. 2. If in FIG. 1 there had been instead two concentrically arranged (also referred to as "radially displaced") windings of mutually different radii, and section 2-2 was taken at 90° to the section shown in FIG. 2, the resulting more or less axisymmetric toroidal structure would have an axis of axisymmetry that is horizontal as viewed in FIG. 2. Stating this another way, the cross-sectional profile shown in FIG. 2 can be used to form a solid of revolution having an axis of axisymmetry which is vertical as viewed in FIG. 2 to obtain the axially displaced configuration shown in FIG. 1; or the cross-sectional profile shown in FIG. 2 might be used to form a solid of revolution having an axis of axisymmetry which is horizontal as viewed in FIG. 2 to obtain a radially displaced configuration in which the windings are arranged concentrically, the ferrite half-core at the winding of larger radius having open side thereof facing inward and the ferrite half-core at the winding of smaller radius having open side thereof facing outward such that the respective open sides of the ferrite half-cores mutually oppose each other across the airgap therebetween. Note that during operation of the rotary transformer the volume of space swept out by core airgap 102 and bounded by imaginary surfaces 145 and 195 to which the core-airgap interfaces of ferromagnetic half-cores 115, 165 more or less conform would in either the case of the axially displaced configuration or the case of the radially displaced configuration be annular, but as the volume of space swept out by core airgap 102, and imaginary surfaces 145 and 195 bounding core airgap 102, will during operation of the rotary transformer be closer to being planar (squat, flat, and washer-like) for the axially displaced configuration, this configuration is sometimes referred to herein as "planar configuration" (also referred to as "plane circular" configuration); and as the volume of space swept out by core airgap 102, and imaginary surfaces 145 and 195 bounding core airgap 102, will during operation of the rotary transformer be closer to being cylindrical for the radially displaced configuration, this configuration is sometimes referred to herein as "cylindrical configuration."

Now, if the axis of rotation is also the axis of symmetry of windings 110, 160 and ferromagnetic half-cores 115, 165, coupling will be substantially unaffected by rotary motion about that axis. In the context of rotary transformers discussed herein, to the extent that the configuration of the rotary transformer is axisymmetric, the axis of axisymmetry of the rotary transformer may be understood to be substantially collinear with the axis of rotation of the rotary transformer; i.e., except where otherwise clear from context, when one of either the axis of axisymmetry or the axis of rotation is said the other may generally be understood to be implied. Note that the term "rotary transformer" is used herein to refer to an inductive power transfer apparatus in which one side is rotatable relative to the other, regardless of whether one or both sides are rotatable relative to, e.g., a stationary exterior point.

Although the foregoing discussion describes how solids of revolution having axes of axisymmetry which are vertical or horizontal as viewed in FIG. 1 might be obtained from a cross-sectional profile such as is shown in FIG. 2, it is in general possible to have axes of axisymmetry and rotation in any direction (but in whatever direction is chosen for the axes of axisymmetry and rotation, it is preferred that the axis of axisymmetry be more or less collinear with the axis of rotation). Where axes of axisymmetry and rotation are other than horizontal or vertical as viewed in FIG. 1, as the volume of space swept out by the core airgap, and the imaginary surfaces bounding the core airgap and to which the core-airgap interfaces more or less conform, during operation of the rotary transformer will be more or less conical, such a configuration is sometimes referred to herein as a "conical configuration" (see, e.g., FIG. 16). Note that in addition to axisymmetry, there may also, to more or less extent, be symmetry with respect to the airgap such that, for example as can be seen at FIG. 2, one side of the rotary transformer (e.g., secondary side) can be understood to be more or less a reflection across the airgap of the winding/core structure on the other side of the rotary transformer (e.g., primary side). As a result of such symmetry whereby primary and secondary sides may, to more or less extent, be reflections of each other across the airgap, dimensions in such case will, for cylindrical and conical configurations, generally contract as one proceeds radially inward toward the axis of rotation and expand as one proceeds radially outward away from the axis of rotation.

Especially because it is preferred for practical operation in accordance with one or more embodiments of the present invention that such power coupling devices be made to operate at frequencies above 20 kHz, it can be expected that the structure of, say, ferrite and copper (to give specific examples of materials that may be used for core half-shells 115, 116 and windings 110, 160) shown in FIG. 2 will generate a dipole field and will radiate strongly to the surrounding space. Where such radiation is undesirable, the ferrite shells might be surrounded by electrically conductive shell(s) serving as shield (see FIG. 4) and designed to carry a current capable of inducing a magnetic field such as will more or less exactly cancel the magnetic field due to the net current in the windings. To the extent that this can be accomplished, escape of radiation to the exterior of such a shield might be expected to be reduced or eliminated.

Note that as used herein, the terms "shield," "shielding," and so forth may, depending upon context, refer narrowly to Faraday-type shielding or other such shielding tending to cancel electromagnetic fields by means of electrical conduction, may refer more generally to shielding including shunting and/or alignment of magnetic fields by appropriate arrangement of windings and/or through use of core or other such low-reluctance material in prescribed geometries, or may refer to any of the various ordinary or specialized meanings with which the terms are used in the art. Specific note is made of the fact that the terms "shield," "shielding," and so forth may be used herein to refer not only to cancellation of electromagnetic fields by electrically conductive parts but also to alignment, channeling, confinement, shunting, and/or guidance of magnetic flux by low-reluctance parts to facilitate cancellation of electromagnetic fields by electrically conductive parts or otherwise prevent or assist in preventing escape of such magnetic flux to the exterior.

Figure 3:
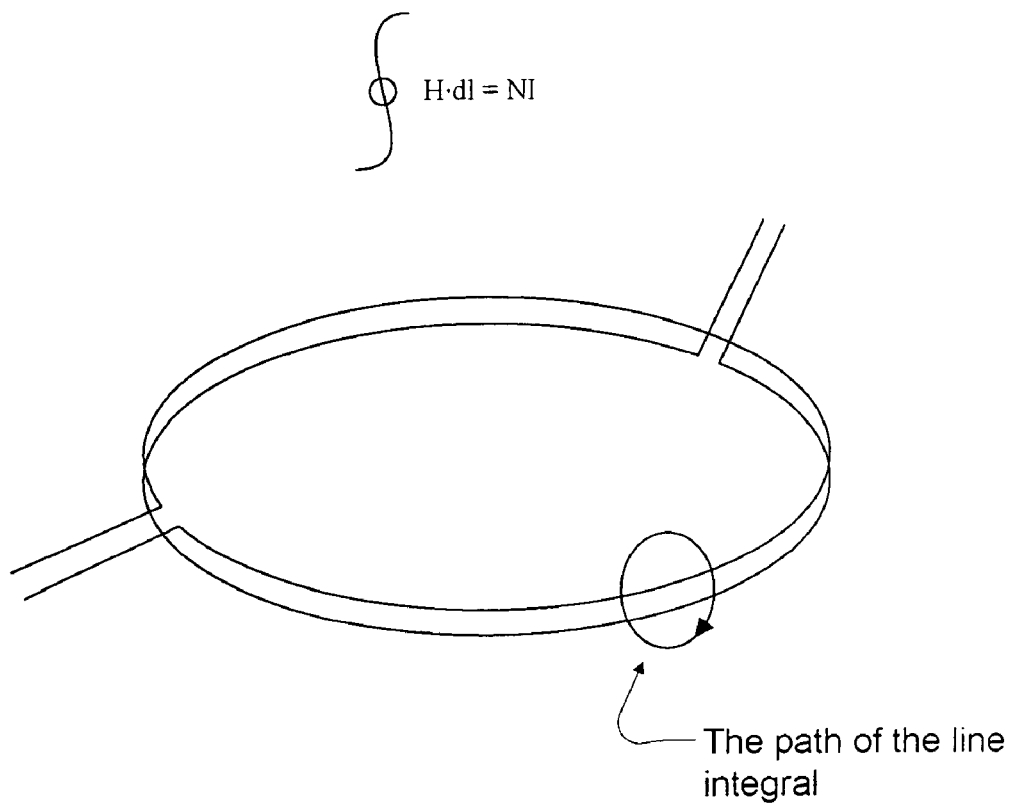
FIG. 3 is a perspective view of windings 110, 160 shown in FIG. 1 indicating the path of a closed line integral around the wires making up windings 110, 160.

Referring to FIG. 3, this is a perspective view of windings 110, 160 shown in FIG. 1 indicating the path of a closed line integral around the wires making up windings 110, 160. FIG. 3 is presented as bases for discussion to evaluate radiation which might be generated by such a structure under different circumstances. Here, H and dl are vector quantities, and the integral is the closed line integral of their scalar product around a path going through the central region circumscribed by the two windings.

Figure 4:
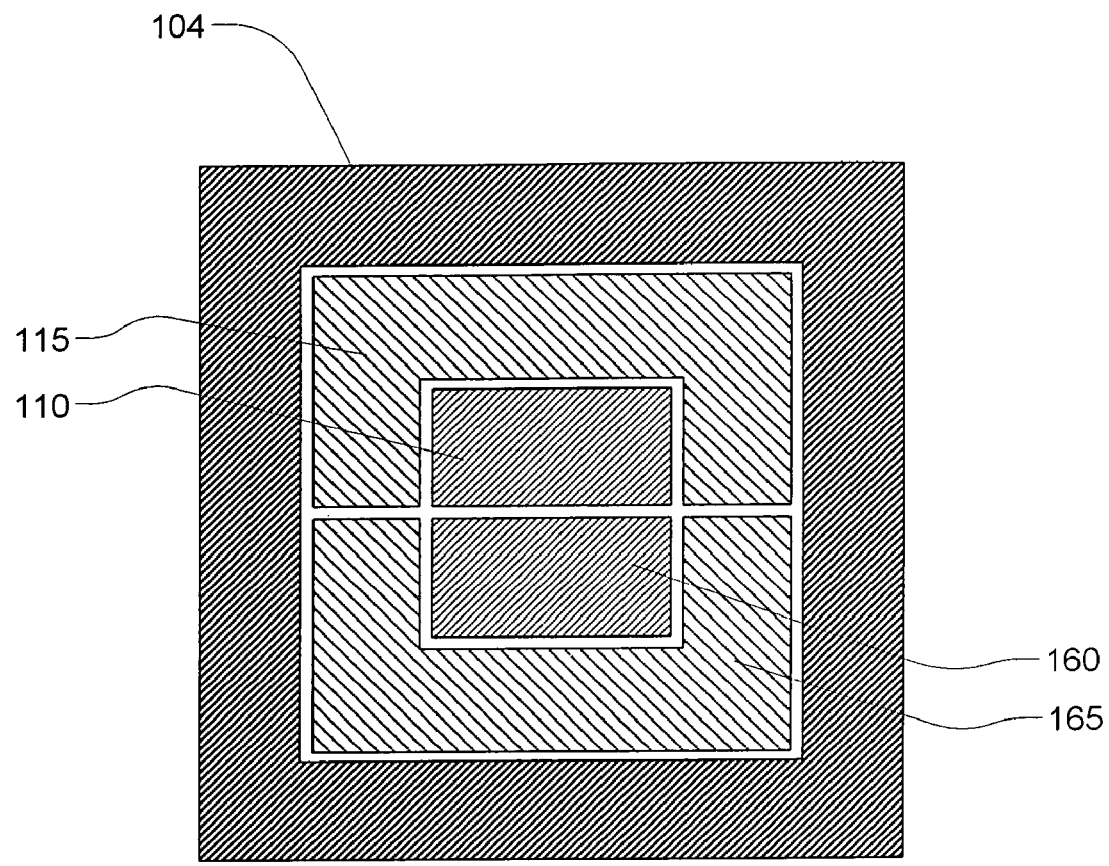
FIG. 4 is a sectional view showing a structure in which the winding/core system shown in FIG. 2 is completely surrounded by a single common shield 104.

Referring now to FIG. 4, this is a sectional view showing a structure in which the winding/core system of FIG. 2 is completely surrounded by a single common shield 104. At FIG. 4, shield 104 may be, for example, a shell of metal (e.g., an aluminum alloy; but any electrically conductive material may be used). Winding regions 110, 160 contain wires carrying currents perpendicular to the plane of the paper in FIG. 4. Core regions 115, 165 contain ferromagnetic material(s) which, for frequencies above 20 kHz, are preferably ferrite, an electrically nonconductive ferromagnetic ceramic. Note that core regions 115 and 165 are shown in the drawing as two separate parts because presence of airgap to allow relative rotation was previously contemplated; for the purpose of the present explanation, core regions 115 and 165 might just as well be formed from a single continuous part.

Now, Maxwell's equations predict that any oscillating magnetic field will induce an oscillating electric field at right angles thereto. In a metal, for example, this electric field causes currents to flow which tend to cancel the magnetic field. For this reason, oscillating magnetic fields should not be able to penetrate very far into a metal. If shield 104 is thick enough, the oscillating magnetic fields in it should be substantially zero beyond a certain penetration depth. From FIG. 3, it is also to be expected that the sum of the currents induced in shield 104 at FIG. 4 will be in the same direction and magnitude as but opposite in sign to the net current in the wires in regions 110 and 160; i.e., electric currents induced in shield 104 should be of such magnitude and direction as to cancel the magnetic field produced by the current flowing in windings 110, 160. That is, H is expected to be zero at the outer surface of the aluminum shell serving as shield 104, so the total current inside this closed surface is expected to be zero, and the sum of the currents induced on or near the inner surface of shield 104 is expected to be equal in magnitude but opposite in sign to the sum of the currents in windings 110, 160. Based on this fact, it is to be expected that flow of current in shield 104 will be in a direction that is perpendicular to the plane of the paper in FIG. 4, which is to say that the current in shield 104 will flow in more or less the same direction, though opposite in sign, as the net current flowing in the wires at windings 110, 160.

Bearing in mind that the three-dimensional axisymmetric solid of revolution derivable from the cross-sectional profile shown in FIG. 4 is generally toroidal with electric current in windings 110, 160 flowing more or less circumferentially along major circle(s) (or along circle(s) coaxial with major circle(s)) during operation of the power coupling device, magnetic flux lines produced at such time can be understood to lie in meridional planes of the overall axisymmetric structure, and as it is preferred that any directionality in the reluctance-lowering distribution of material at core regions 115 and 165 should preferably be designed to reinforce rather than alter this magnetic flux line geometry, a situation is obtained which is similar to that described with reference to FIG. 1 inasmuch as loops of magnetic flux mutually linking the primary and secondary windings can be understood to lie in the planes of minor circles of the toroidal volume occupied by that more or less axisymmetric structure. This being the case, at FIG. 4, it will be understood that the currents flowing in the wires at windings 110, 160, and the currents induced thereby and flowing in shield 104, come out of and go into the plane of the paper perpendicularly at FIG. 4; but that as those currents emerge from the plane of the paper, they curve to follow (preserve their geometric relationship with respect to) major circle(s) of the toroidal volume occupied by the overall axisymmetric structure, the specific direction in which such toroid major circle(s) run depending upon where the axis of axisymmetry (and therefore the axis of rotation) is relative to the cross-section shown in FIG. 4 and depending upon whether the cross-section shown in FIG. 4 is part of a rotary transformer having planar, cylindrical, or conical configuration as described above.

Figure 5:
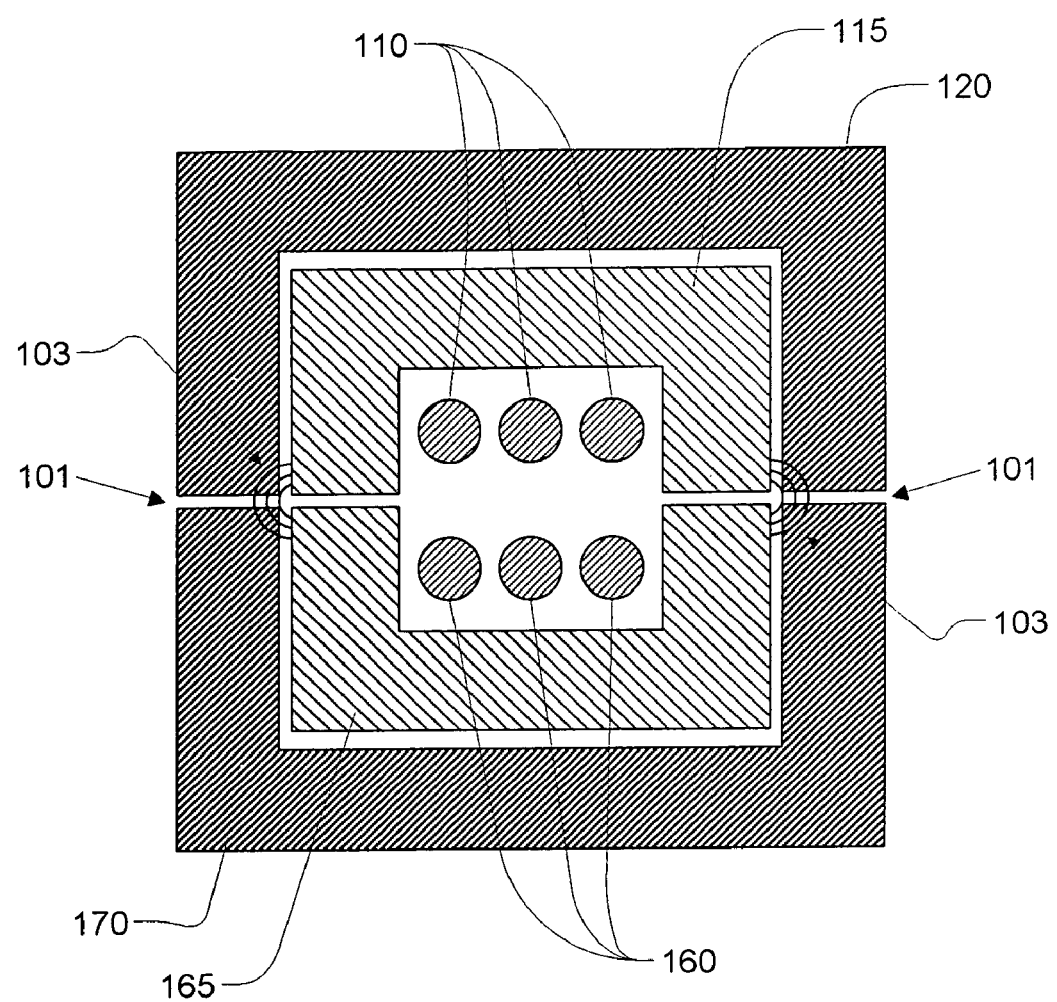
FIG. 5 is a sectional view showing a situation in which common shield 104 shown in FIG. 4 has been split into two half-shields 120, 170 by shield airgaps 101.

Referring to FIG. 5, this shows a sectional view of a situation in which shield 104 shown in FIG. 4 has been split into two half-shields 120, 170, with shield airgaps 101 intervening therebetween. At FIG. 5, two mutually opposed three-turn windings are disposed within mutually opposed C-shaped core recesses. At this time, if separation of shield 104 into half-shields 120, 170 by shield airgaps 101 is such that the volumes of space swept out by shield airgaps 101 during operation of the rotary transformer are perpendicular to the plane of the paper in FIG. 4, then, from the foregoing discussion, it is to be expected that presence of shield airgaps 101 need not in general necessarily impede flow of the aforementioned electric currents which are induced in the shield shell during operation of the power coupling device, inasmuch as such electric currents, to the extent that they behave as contemplated in the description above, would not be expected to have a component which would tend to cause such induced electric currents to cross shield airgaps 101. In the description given with reference to FIG. 5, note that even where half-cores are meant, the prefix "half-" may sometimes be omitted for convenience of description.

Again bearing in mind that the three-dimensional axisymmetric solid of revolution derivable from the cross-sectional profile shown in FIG. 5 is generally toroidal with electric current in windings 110, 160 flowing more or less circumferentially along major circle(s) (or along circle(s) coaxial with major circle(s)) during operation of the power coupling device, as was the case with the currents flowing in windings 110, 160 and the field-canceling currents induced thereby and flowing in shield 104 described with reference to FIG. 4, the currents flowing in windings 110, 160 and the field-canceling currents induced thereby and flowing in half-shields 120, 170 at FIG. 5 should similarly be understood to come out of and go into the plane of the paper perpendicularly at FIG. 5; but that as those currents emerge from the plane of the paper, they curve to follow (preserve their geometric relationship with respect to) major circle(s) of the toroidal volume occupied by the overall axisymmetric structure, the specific direction in which such toroid major circle(s) run depending upon where the axis of axisymmetry (and therefore the axis of rotation) is relative to the cross-section shown in FIG. 5 and depending upon whether the cross-section shown in FIG. 5 is part of a rotary transformer having planar, cylindrical, or conical configuration as described above.

Such field-canceling electric current(s) flowing in shield 104 and described with reference to FIG. 4, or flowing in half-shields 120, 170 and described with reference to FIG. 5, might be called "image currents" because they resemble, except for sign, electric current(s) flowing in windings 110, 160. More specifically, the term "image current(s)" as used herein refers to current(s) capable of canceling magnetic field (s) formed by current(s) of which they are an image.

To permit such field-canceling image current(s) to flow more or less circumferentially along circle(s) coaxial with major circle(s) of the toroidal volume occupied by the overall axisymmetric structure, it is preferred that half-shield(s) 120, 170 comprise electrically conductive material forming substantially continuous electrical path(s) constituting closed electric circuit(s) around the axis of rotation, e.g., circumferential path(s) along circle(s) coaxial with major circle(s) of the toroidal volume occupied by the overall axisymmetric structure. It is furthermore preferred that such continuous electrical path(s) be capable of supporting electric current(s) sufficient to induce magnetic field(s) such as will substantially cancel magnetic field(s) due to electric current(s) flowing in windings 110, 160 during operation of the power coupling device.

An axisymmetric solid of revolution such as that derivable from the cross-sectional profile shown in FIG. 5 may be described in terms of "global" characteristics which pertain to the overall axisymmetric structure or may be described in terms of "local" characteristics which pertain to a representative meridional cross-section thereof. That is, with respect to overall or global characteristics, the axisymmetric solid of revolution derivable from the cross-sectional profile shown in FIG. 5 is generally toroidal, with current(s) in windings 110, 160; current(s) in half-shields 120, 170; and the volumes of space swept out by shield airgaps 101 emerging from the plane of the paper perpendicularly at FIG. 5 but curving to follow toroid major circle(s) as these emerge therefrom; moreover, loops of magnetic flux aligned by cores 115, 165 lie in planes of toroid minor circle(s). With respect to cross-sectional or local characteristics, if description is confined to the situation existing in the plane of the paper at FIG. 5, to the extent that field-canceling currents flowing in half-shields 120, 170; currents flowing in windings 110, 160; and volumes of space swept out by shield airgaps 101 respectively emerge perpendicularly from the plane of the paper at FIG. 5, it may be convenient to say that these are all, e.g., in the section shown in FIG. 5, mutually parallel; moreover, to the extent that loops of aligned magnetic flux lie in the plane of the paper at FIG. 5, it may be convenient to say that the lines of aligned magnetic flux are, e.g., in the section shown in FIG. 5, perpendicular to field-canceling currents flowing in half-shields 120, 170; to currents flowing in windings 110, 160; and to imaginary surfaces bounding volumes of space swept out by shield airgaps 101.

From the foregoing, to the extent that magnetic flux lines of the time-varying magnetic field at core regions 115, 165 are, e.g., in the section shown in FIG. 5, more or less perpendicular to current(s) in windings 110, 160; to current(s) in half-shields 120, 170; and to surfaces bounding volumes of space swept out by shield airgaps 101, it can be seen that such lines of magnetic flux will not tend to induce flow of current across shield airgaps 101. In other words, in such case it is to be expected that there will be no tendency for current to flow in a direction that would bridge shield airgap 101; which is to say that that there will be no tendency for current to flow in a direction perpendicular to an imaginary surface bounding the volume of space swept out by shield airgap 101 during operation of the power coupling device. That is, when shield 104 shown in FIG. 4 is split into two half-shields 120, 170 as shown in FIG. 5, shield airgaps 101 which intervene therebetween being, e.g., in the section shown in FIG. 5, perpendicular to the magnetic field (i.e., an imaginary surface bounding the volume in space swept out by airgap 101 during operation of the power coupling device being perpendicular to the magnetic field) and separating half-shields 120, 170 by small amounts, it is to be expected that little or no loss of shielding will result, since the currents flowing in half-shields 120, 170 are expected to be essentially the same as those in unsplit common shield 104 shown in FIG. 4. That is, where, e.g., in the section shown in FIG. 5, the magnetic fields have no component parallel to shield airgaps 101 (i.e., have no component parallel to an imaginary surface bounding the volume of space swept out by airgap 101 during operation of the power coupling device) and the net currents flowing in half-shields 120, 170 have no component perpendicular to shield airgaps 101 (i.e., have no component perpendicular to an imaginary surface bounding the volume of space swept out by airgap 101 during operation of the power coupling device), it is to be expected that half-shields 120, 170 can be designed such that little or no radiation is able to reach the exterior of the shield despite presence of shield airgaps 101.

With continued reference to FIG. 5, the current flowing in the shielded transformer-like system shown in the drawing will be the magnetization current plus the two load currents, the two load currents being essentially equal in magnitude but opposite in phase (one load current being in the primary and the other load current which is induced thereby being in the secondary). Ferrites in core regions 115, 165 channel and shunt magnetic field flux loops such that very little magnetic flux would escape therefrom if core regions 115 and 165 were formed from a single continuous part; but because core regions 115 and 165 are split into two separate parts to permit relative rotation, most of the magnetic flux entering and exiting core regions 115, 165 does so in the neighborhood of the core airgap periphery at the regions marked 103, where fringing fields (also referred to as "fringe fields") are shown emanating therefrom in schematic fashion in the drawing.

At such time, electric currents will be induced in half-shields 120, 170 on and near the inner surfaces of half-shields 120, 170 in the neighborhood of the core airgap periphery where fringing fields 103 impinge thereon, such induced currents tending to cancel the fringing fields 103 that induced them. To the extent that such phenomena as misalignment of core regions 115 and 165, nonuniformity in distribution of reluctance-lowering material in core regions 115 and 165, aberrations or deviations in surface topology or geometry at the core airgap, and the like may cause fringing fields 103 to have a component which would tend to cause such induced electric currents to cross shield airgaps 101, it can be expected that the problem of shielding fringing fields 103 to prevent emission of radiation to the exterior of the power coupling device will be made more difficult. To the extent that fringing fields 103 do not have a component which would tend to cause such induced electric currents to cross shield airgaps 101, it is to be expected, if half-shields 120, 170 are of sufficient thickness and electrical conductivity, that it will in general be possible to cancel the magnetic field responsible for such induced currents before such currents can be conducted to the outer surfaces of half-shields 120, 170.

This being the case, it is therefore preferred in one or more embodiments of the present invention that half-shields 120, 170 have, adjacent to core airgap(s), fringe field canceling zone(s) of thickness(es) and electrical conductivity or conductivities sufficient to substantially cancel fringing fields due to magnetic flux emanating from core airgap(s) before effects of such emanating magnetic flux would reach outer surfaces of half-shields 120, 170; e.g., before electric currents produced thereby in half-shields 120, 170 would be conducted to outer surface(s) of half-shields 120, 170. It is furthermore preferred that, where present, such fringe field canceling zone(s) comprise electrically conductive material(s) forming substantially continuous electrical path(s) constituting closed electric circuit(s) around the axis of rotation, e.g., circumferential path(s) along circle(s) coaxial with major circle(s) of the toroidal volume occupied by the overall axisymmetric structure. It is still furthermore preferred that continuous electrical path(s) at fringe field canceling zone(s), where present, be capable of supporting electric current(s) sufficient to induce magnetic field(s) such as will substantially cancel magnetic field(s) due to electric current(s) flowing in windings 110, 160 during operation of the power coupling device.

To better understand fringing field(s) such as might emanate from core airgap(s) for various core/shield geometries and how such fringing field(s) might be canceled by fringe field canceling zone(s) on or near inner surface(s) of shield(s), reference is now made to FIGS. 6 through 10.

Referring to FIGS. 6 through 10, these drawings show results of finite element simulation to determine where current will flow in the shield, i.e., location(s) and extent(s) of fringe field canceling zone(s), when the shield is subjected to a fringing field emanating from a core airgap between mutually opposed ferrite E-cores. At FIGS. 6 through 10, only shield parts are labeled, cores and windings being more or less as shown in FIG. 5; except that whereas a single pair of mutually opposed three-turn windings disposed within mutually opposed C-shaped core recesses was shown at FIG. 5, two pairs of mutually opposed three-turn windings disposed within mutually opposed E-shaped core recesses are shown at FIGS. 6 through 10. In the description given with reference to FIGS. 6 through 10, note that even where half-cores are meant, the prefix "half-" may sometimes be omitted for convenience of description.

Figure 6:
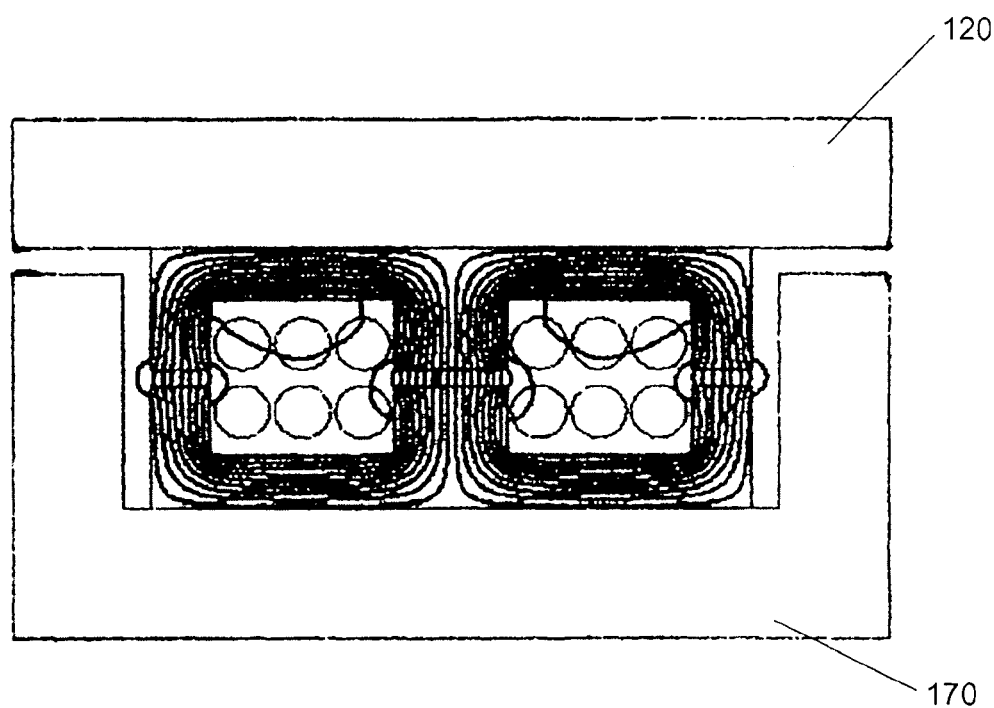
FIG. 6 is a sectional view showing a magnetic field as would be produced by the winding/core system shown and which was used to generate the shield current finite element simulation studies of FIGS. 7 through 10.

As the winding/core geometry is identical at FIGS. 6 through 10, the magnetic field produced thereby will be essentially the same in all cases, this common magnetic field profile being shown at FIG. 6. Note that although a shield 120, 170 is shown at FIG. 6 (this shield, it so happens, being the shield configuration shown in FIG. 8), this is provided only for reference purposes and is irrelevant to production of the magnetic field shown.

As can be seen at FIGS. 6 through 10, where the core material is discontinuous at the core airgap (i.e., where flux lines must cross the core-air-core interface(s)), the flux lines that would otherwise be contained (shunted) within the core material leak out to form fringing fields. At FIGS. 6 through 10, note that the core airgap is shown narrower than the shield airgap, this generally being preferred in some embodiments of the present invention where a narrow core airgap may be desirable to improve coupling between primary and secondary sides, reduce leakage inductance, reduce fringing, or the like, but where somewhat wider shield airgap(s) (and to some extent, somewhat wider winding airgap(s), although not shown as such in the drawings) may be desirable to reduce capacitance, permit looser dimensional tolerances on parts in mutual proximity during rotation, and so forth.

With reference to FIG. 6, it can be seen that magnetic flux lines are largely shunted by (confined within) the core, except where magnetic flux escapes therefrom in the vicinity of the core airgap; for this reason, it might be expected that, for the winding/core configuration shown, it might be possible to achieve effective shielding even where the shield has comparatively little electric-current-supporting ability at locations not in the vicinity of the core airgap. For example, where magnetic flux is sufficiently shunted by the cores, the two-part cutback nonadjacent-airgap shield configuration shown in FIG. 9 may provide adequate shielding; as another example, adequate shielding may be provided even where upper half-shield 120 is omitted from the two-part wraparound nonadjacent-airgap shield configuration shown in FIG. 8.

With continued reference to FIG. 6, to reduce the extent of flux line distortion in the vicinity of the core airgap, it is preferred in one or more embodiments of the present invention that the mutually opposed core surfaces separated by the core airgap (i.e., core-airgap interfaces) be smooth and mutually parallel and that such core-airgap interface surfaces be normal to the predominant direction of magnetic flux lines bridging the core airgap.

With continued reference to FIG. 6, note that use of an E-shaped core causes tandem flow of two sets of magnetic flux loops; i.e., the E-core can be thought of as approximating a situation in which two C-cores lie side-by-side. Note that where use of E-core(s) or other arrangement of reluctance-lowering material is such as to produce multiple sets of magnetic flux loops as is the case at FIG. 6, reference in the present description and claims to toroidal geometries, minor circles thereof, and so forth should not be understood to exclude the possibility of such multiple sets of magnetic flux loops, it being possible in general to apply various aspects of the present invention thereto. For example, even where there are multiple sets of magnetic flux loops, such magnetic flux loops can be expected to lie in meridional planes of the overall axisymmetric structure, and the geometry of alignment of such magnetic flux loops relative to the shield and the geometry by which fringing fields escaping from core airgap(s) create fringe field canceling currents in the shield is essentially unchanged; and in any event, it will be possible to greater or lesser extent to apply various aspects of the present invention separately to each set of magnetic flux loops shunted by each toroidal distribution of core material (e.g., each set of windings disposed within mutually opposed recesses of the mutually opposed E-cores at FIG. 6). Further note that although the drawings may show only C-cores and E-cores, higher-order cores (i.e., cores having more than two recesses; or having more than three arm-like pole members) are of course possible, and various aspects of the invention can be applied thereto with appropriate modification as necessary. Note that where, for example, an E-core is used, flux lines emanating from the core airgap at the central E-core pole member (e.g., the central core airgap at FIG. 6) will generally play a less significant role with respect to RF emission than flux lines emanating from the core airgaps at the E-core pole members at either side in FIG. 6, and so shielding can be expected in such case to focus attention on fringing fields emanating from core airgaps at peripheral pole members (i.e., distal pole members, where distal is as defined below with respect to FIG. 13 *ff.*).

Although not shown at FIGS. 6 through 10, an AC power supply is preferably connected to the three-turn primary winding disposed in the E-core recess at upper left in the drawing and to the three-turn primary winding disposed in the E-core recess at upper right in the drawing in such manner as to cause the net instantaneous current flowing in those primary windings to be zero. That is, where number of windings, selection of alternating current(s) flowing therethrough (e.g., two-phase, three-phase, polyphase, etc.), and so forth are such that net current flowing through the primary windings is instantaneously zero, currents induced in half-shields 120, 170 during operation of the shielded power coupling device can be expected to be smaller in magnitude than is the case when, e.g., single-phase AC current is used with a single winding, e.g., such as might be wound within the recess of a half-core having C-shaped cross-section, at each the primary and the secondary side, since the magnetization current in the primary will remain uncanceled in the single-phase/single-winding case.

That is, to the extent that the shield works as described thus far, it is to be expected that the net current in the shield will be equal in magnitude but opposite in sign to the net current in the windings. Where the primary and the secondary side of the rotary transformer each comprise a single winding, as is the case with the three-turn winding disposed within the single recess of the C-core at each the primary and secondary side at FIG. 5, as the load current present in opposite phases in the primary and the secondary windings mutually cancel, the net current in the windings will be the magnetization current present in the primary winding. But where the primary and the secondary side of the rotary transformer each comprise multiple windings, as is the case with the two three-turn windings respectively disposed within the two recesses of the E-core at each the primary and secondary side at FIGS. 6 through 10, it will be possible to obtain a situation in which the respective magnetization currents present in the multiple primary windings mutually cancel so as to produce a net instantaneous current of substantially zero in the primary windings. Even where net current in the windings is zero, the fact that the current in those windings is not perfectly lumped but has distribution in space means that there will still be currents flowing in the shield which induce magnetic fields that cancel the fringing fields and so forth; the field-canceling currents in such case will sum to zero but will dissipate power.

Shields shown at FIGS. 7 through 10 are capable of substantially canceling fringing fields as indicated in the drawings; more specifically, shields shown at FIGS. 7 through 10 have electrically conductive material at such locations and in such electrical conductivity or conductivities and thickness or thicknesses as is sufficient to permit flow of electric currents such as will induce a magnetic field capable of substantially canceling the fringing field before the fringing field would reach the shield exterior when the power coupling device is operated.

Figure 7:
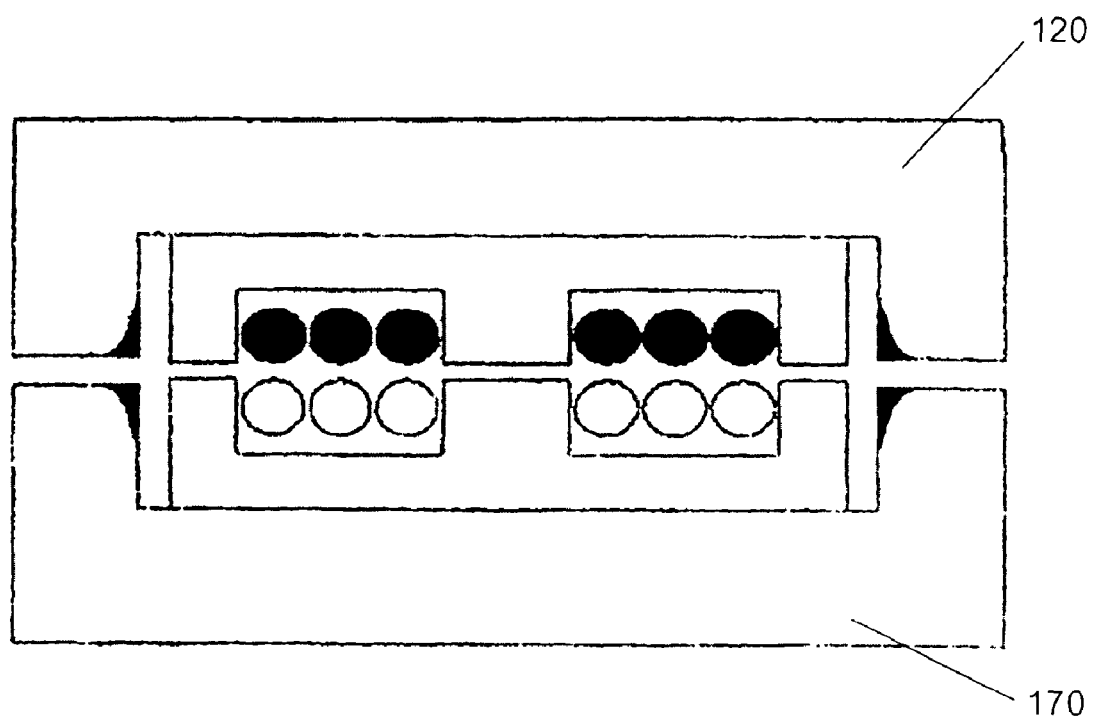
FIG. 7 is a sectional view showing a finite element simulation to determine where field-canceling currents flow when fringing fields emanating from the peripheries of core airgaps impinge on either part of a two-part wraparound shield having shield airgaps that are adjacent to the core airgaps.

At the finite element simulation shown in FIG. 7, at either the left side and the right side as viewed in the drawing, field-canceling currents flow when a fringing field emanating from the periphery of a core airgap impinges on either part 120, 170 of a two-part wraparound shield having shield airgaps that are adjacent to the core airgaps; during cancellation of fringing fields by the shield shown in FIG. 7, field-canceling currents flow within half-shields 120, 170 in a direction perpendicular to the plane of the page at the four darkened regions indicated in the drawing. At the finite element simulation shown in FIG. 8, field-canceling currents flow when fringing fields emanating from peripheries of core airgaps impinge on the same part 170 of a two-part wraparound shield having shield airgaps that are nonadjacent with respect to the core airgaps; during cancellation of fringing fields by the shield shown in FIG. 8, field-canceling currents flow within half-shield 170 in a direction perpendicular to the plane of the page at the two darkened regions indicated in the drawing. At the finite element simulation shown in FIG. 9, at either the left side and the right side as viewed in the drawing, field-canceling currents flow when a fringing field emanating from the periphery of a core airgap impinges on one or the other part 120, 170 of a two-part cutback shield having shield airgaps that are nonadjacent with respect to the core airgaps; during cancellation of fringing fields by the shield shown in FIG. 9, field-canceling currents flow within half-shields 120, 170 in a direction perpendicular to the plane of the page at the two darkened regions indicated in the drawing. At the finite element simulation shown in FIG. 10, field-canceling currents flow when fringing fields emanating from peripheries of core airgaps impinge on the single part 170 of a one-part wraparound shield having a shield airgap that is nonadjacent with respect to the core airgaps; during cancellation of fringing fields by the shield shown in FIG. 10, field-canceling currents flow within the single part 170 of the shield in a direction perpendicular to the plane of the page at the two darkened regions indicated in the drawing. At the one-part wraparound adjacent-airgap shield shown in FIG. 10, the single shield airgap in the upper portion of the drawing might be just large enough to allow for mechanical support and electrical connection.

In the configuration shown at FIG. 7, note that, at each the left side and the right side as viewed in the drawing, the shield airgap is adjacent to the core airgap, which is to say that the core airgap and the shield airgap more or less conform to substantially the same imaginary surface(s); i.e., the volume of space swept out by the core airgap (this being more or less planar, cylindrical, or conical as described above) is more or less coextensive with the volume of space swept out by the shield airgap.

Figure 8:
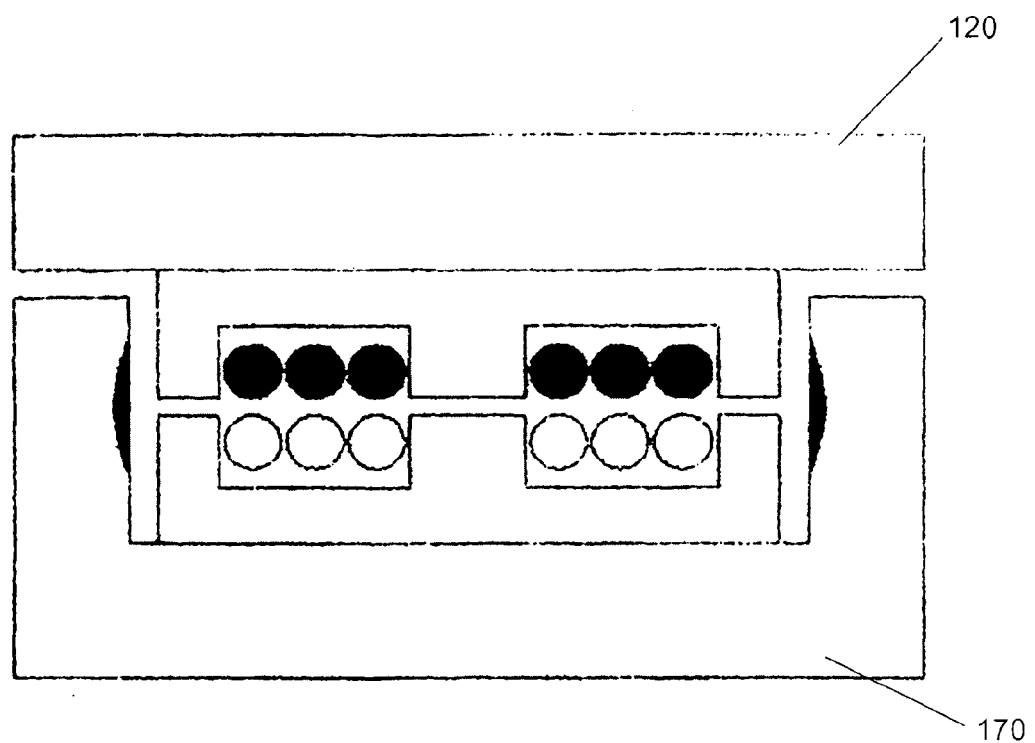
FIG. 8 is a sectional view showing a finite element simulation to determine where field-canceling currents flow when fringing fields emanating from peripheries of core airgaps impinge on the same part of a two-part wraparound shield having shield airgaps that are nonadjacent with respect to the core airgaps.
Figure 9:
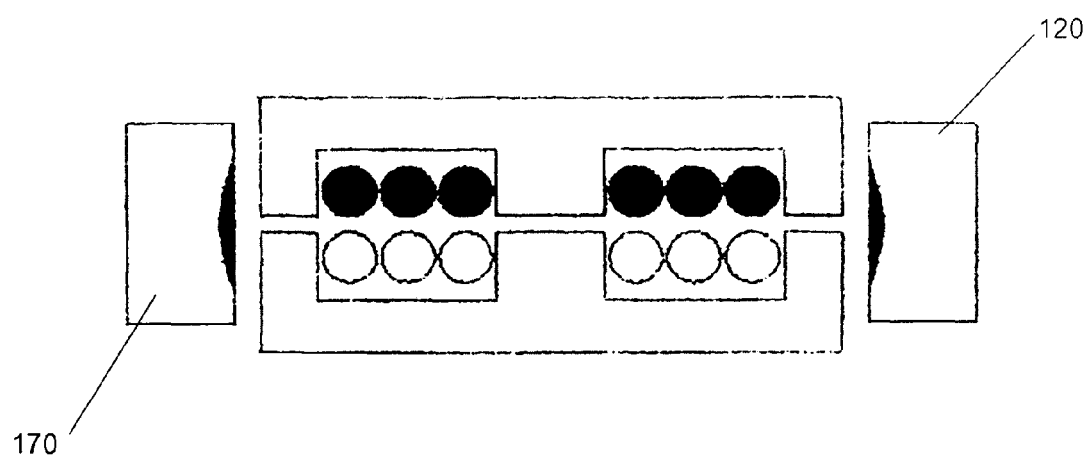
FIG. 9 is a sectional view showing a finite element simulation to determine where field-canceling currents flow when fringing fields emanating from the periphery of a core airgap impinge on a two-part cutback shield having shield airgaps that are nonadjacent with respect to the core airgaps.
Figure 10:
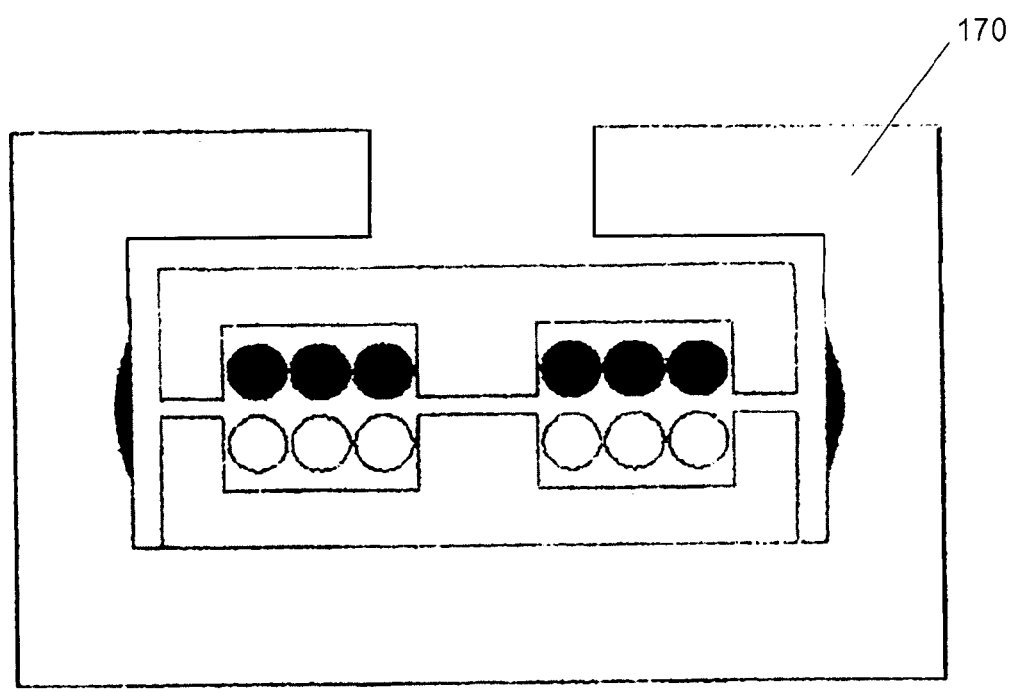
FIG. 10 is a sectional view showing a finite element simulation to determine where field-canceling currents flow when fringing fields emanating from peripheries of core airgaps impinge on a one-part wraparound shield having a shield airgap that is nonadjacent with respect to the core airgaps.

In the configurations shown at FIGS. 8 through 10, note that, at each the left side and the right side as viewed in the drawing, the shield airgap is not adjacent to the core airgap, which is to say that the shield has an overhanging or occluding profile such that electrically conductive material in the shield at least partially occludes the core airgap from the shield exterior; i.e., the core airgap and the shield airgap do not conform to the same imaginary surface, nor is the volume of space swept out by the core airgap coextensive with the volume of space swept out by the shield airgap.

Although for small shield airgaps such as those shown in FIG. 7 there is attenuation of fringing fields even when the shield airgap is adjacent to the core airgap as can be seen at FIG. 7, it is apparent that the fringing fields extend father into the shield airgap and come closer to emerging beyond the shield airgap to the shield exterior when the shield airgap is disposed adjacent to the core airgap as it is in FIG. 7 than when the shield airgap is disposed at a location removed from the core airgap as it is in FIGS. 8 through 10. Where shield thickness, shield electrical conductivity, power, frequency, and the like are such as to threaten ability of the shield to support fringe field canceling currents, this may have more deleterious effect with respect to RF noise emission when the shield airgap is disposed adjacent to the core airgap as at FIG. 7 than when the shield airgap is located more distant from the core airgap as at FIGS. 8 through 10, since in the latter case (i.e., where shield airgap and core airgap are mutually nonadjacent) there will generally be more opportunity for currents induced in the shield between the site of the fringing field (i.e., core airgap) and the site of the shield airgap to induce magnetic fields capable of canceling the fringing fields before the fringing fields would reach the shield exterior. Although the nonadjacent-type configuration shown in FIGS. 8 through 10 may therefore be better suited to applications involving high power and/or thin shields, it may be more convenient in practice to manufacture the adjacent-type configuration shown in FIG. 7.

Moreover, inasmuch as fringing fields and/or other magnetic fields misaligned such that magnetic flux loops are not completely confined to meridional planes, such that magnetic flux loops are not completely confined to planes of toroid minor circles, or such that lines of magnetic flux contain a component parallel to a surface bounding the volume of space swept out by shield airgap(s) 101, configurations in which shield airgap(s) is/are disposed at location(s) removed from core airgap(s) as is the case for the configurations shown at FIGS. 8 through 10 might be expected to provide better shielding than configurations in which shield airgap(s) is/are disposed at location(s) adjacent to core airgap(s) as is the case for the configuration shown at FIG. 7, since nonadjacent configurations such as those shown at FIGS. 8 through 10 may permit flow not only of shield currents in, say, the toroid major circle direction to induce a magnetic field tending to cancel the fringing field component in the toroid minor circle direction, but may also, to greater or lesser extent, permit flow of shield currents even in, say, the toroid minor circle direction to induce a magnetic field tending to cancel any fringing field component which may exist even in the toroid major circle direction. That is, whereas in the description given above with reference to FIGS. 4 and 5 it was contemplated that alignment of magnetic flux was such that electric currents induced in the shield did not have a component tending to cross shield airgap(s) 101, in real-life devices there may in fact be misaligned lines of magnetic flux emanating from the core airgap periphery or elsewhere which would tend to induce electric currents having a component in the toroid minor circle direction that would make the shield radiate in electric-dipole-like fashion if such induced currents were unable to flow because of presence of shield airgap(s) 101. To the extent that the shield has extension in the toroid minor circle direction, i.e., to the extent that the shield wraps angularly around the core/winding system as viewed in the meridional section shown in FIGS. 7 through 10, it may therefore be preferable to cause shield airgap(s) to be disposed at location(s) nonadjacent with respect to core airgap(s) as shown at FIGS. 8 through 10 rather than at location(s) adjacent to core airgap(s) as shown at FIG. 7.

With respect to definition of the shield airgap when the shield airgap is large, note that at FIG. 9 there are two large shield airgaps, these being at the upper portion and the lower portion of the drawing; while at FIG. 10 there is a single large airgap, this being at the upper portion of the drawing.

Especially where an adjacent-type configuration as shown in FIG. 7 is employed and taking the case where the shield is made from aluminum, it is preferred that the shield airgap be not greater than one-half of the thickness of the aluminum in the shield thereat, and it is more preferred that the shield airgap be not greater than one-quarter of the thickness of the aluminum in the shield thereat. Generalizing this to shields made from any of various electrically conductive materials, especially where an adjacent-type configuration as shown in FIG. 7 is employed, it is preferred that thickness of the shield in the region of the core airgap be sufficient to achieve an electrical conductivity equivalent to that of aluminum in a thickness of not less than two shield airgap thicknesses, and it is more preferred that thickness of the shield in the region of the core airgap be sufficient to achieve an electrical conductivity equivalent to that of aluminum in a thickness of not less than four shield airgap thicknesses.

Where a nonadjacent-type configuration as shown in FIGS. 8 through 10 is employed, it is preferred, as measured in a direction perpendicular to an imaginary surface bounding the volume of space swept out by the core airgap during operation of the shielded power coupling device, that the distance to the nearest portion of the shield airgap be not less than three core airgap thicknesses from the nearest portion of the core airgap, and it is more preferred that the distance therebetween be not less than five core airgap thicknesses.

Whether an adjacent-type configuration as shown in FIG. 7 is employed or a nonadjacent-type configuration as shown in FIGS. 8 through 10 is employed, it is preferred that thickness of the shield in the region of the core airgap be sufficient to achieve an electrical conductivity equivalent to that of aluminum in a thickness of not less than five core airgap thicknesses, and it is more preferred that thickness of the shield in the region of the core airgap be sufficient to achieve an electrical conductivity equivalent to that of aluminum in a thickness of not less than ten core airgap thicknesses.

Although adjacent-type and nonadjacent-type configurations are shown at FIGS. 7 through 10, there is of course no objection to employing a configuration that is partially adjacent and partially nonadjacent, or that is more or less intermediate between the configuration shown at FIG. 7 and any of the configurations shown at FIGS. 8 through 10.

Furthermore, with regard to desirability, in some embodiments of the present invention, for fringe field canceling zone(s) comprising electrically conductive material(s) to form substantially continuous electrical path(s) constituting closed electric circuit(s) around the axis of rotation, the fact that fringing fields impinge at four locations in the adjacent-type configuration of FIG. 7 but impinge at only two locations in the nonadjacent-type configuration of FIGS. 8 through 10 suggests that it will be preferred that there be four such continuous electrical paths serving as fringe field canceling zones for the adjacent-type configuration, but that two such continuous electrical paths serving as fringe field canceling zones might be sufficient for the nonadjacent-type configuration. Such continuous electrical path(s) constituting closed electric circuit(s) around the axis of rotation may, for example, be circular, annular, semitoroidal, and/or may take the form of ring-like band(s) adjacent to and alongside core airgap(s). Where such continuous electrical path(s) take the form of ring-like band(s) adjacent to and alongside core airgap(s), such ring-like band(s) might be substantially annular for power coupling devices having planar or cylindrical configuration, and such ring-like band(s) might be substantially conical sections for power coupling devices having conical configuration.

Figure 11:
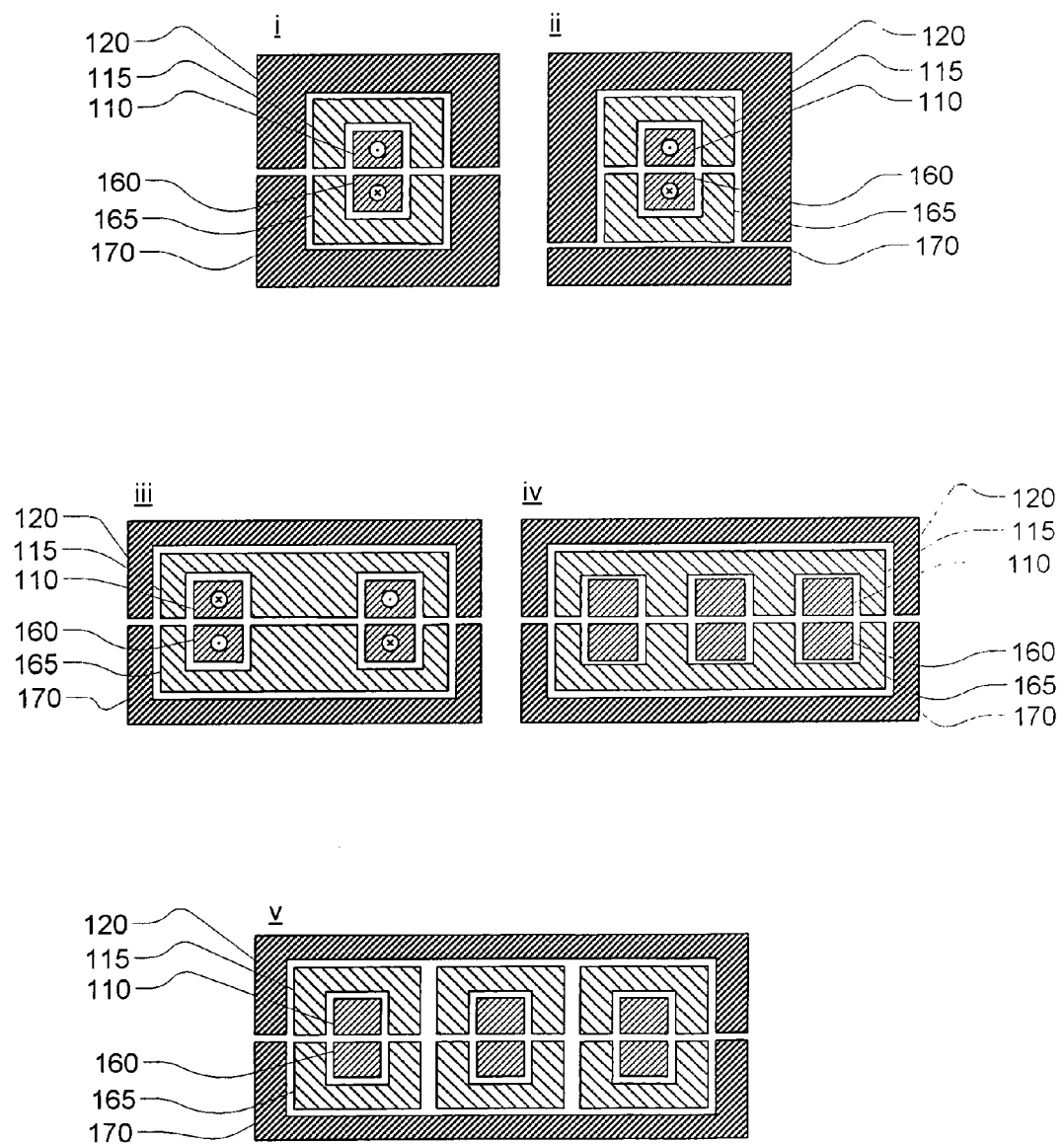
FIG. 11 shows several representative cross-sectional profiles that might be used to generate axisymmetric solids of revolution to which the structure of rotary transformers in accordance with embodiments of the present invention might conform.

Referring now to FIG. 11, this is a side view showing several representative cross-sectional profiles that might be used to generate axisymmetric solids of revolution to which the structure of rotary transformers in accordance with embodiments of the present invention might conform. At FIG. 11, like-numbered parts have function as described above. Each of the five configurations labeled i through v at FIG. 11 can be expected to provide adequate shielding when used as cross-sectional profile to generate a more or less axisymmetric solid of revolution therefrom. At such time, the axis of revolution about which such cross-sectional profile is swept to obtain the more or less axisymmetric rotary transformer structure of various embodiments of the present invention should lie outside of the cross-sectional profile but may be at any radius therefrom and at any orientation with respect thereto. Although reference numerals are shown to indicate parts, no implication of limitation is intended with respect to stationary versus moving sides, primary versus secondary sides, or the like, since these are in general interchangeable.

At FIG. 11, the inset labeled i shows a single primary winding and a single secondary winding respectively disposed within mutually opposed cores having C-shaped cross-section and shows a shield configuration such that shield airgaps are adjacent to core airgaps; the inset labeled ii shows a single primary winding and a single secondary winding respectively disposed within mutually opposed cores having C-shaped cross-section and shows a shield configuration such that shield airgaps are nonadjacent with respect to core airgaps; the inset labeled iii shows a double primary winding and a double secondary winding respectively disposed within mutually opposed cores having a common core structure having E-shaped cross-section and shows a shield configuration such that shield airgaps are adjacent to core airgaps; the inset labeled iv shows a winding/core arrangement having a common core structure suitable for three-phase alternating current and shows a shield configuration such that shield airgaps are adjacent to core airgaps; and the inset labeled v shows a winding/core arrangement having three separate core structures suitable for three-phase alternating current and shows a shield configuration such that shield airgaps are adjacent to core airgaps. Here, where number of windings, choice of alternating current(s) flowing therethrough (e.g., two-phase, three-phase, polyphase, etc.), and so forth are such as to allow a net instantaneous current of substantially zero to be made to flow through the primary windings (i.e., such that respective magnetization currents at respective primary windings mutually cancel), this being possible for the winding/core arrangements having multiple windings at each the primary and the secondary side as shown at insets iii, iv, and v, it will be possible to achieve significant reduction in shield current as was described above with reference to FIGS. 6 through 10.

As described above with reference to FIGS. 7 through 10, it is to be expected that all of the structures at FIG. 11 can be adequately shielded if the aluminum or other electrically conductive material used in the shield is present in sufficient thickness(es) at location(s) where necessary to support field-canceling currents such as will induce magnetic field(s) capable of canceling the magnetic field(s) responsible for such field-canceling currents before effects of the magnetic field(s) responsible for such field-canceling currents can reach shield outer surface(s); e.g., before such field-canceling currents would be conducted to shield outer surface(s). While the necessary electrically conductive material thickness in such case will in general vary as the reciprocal of the square root of the product of frequency and electrical conductivity, preferred ranges expressed in equivalent aluminum thicknesses as multiples of the core airgap and shields airgap dimension are as described above with reference to FIGS. 7 through 10. Moreover, formation of substantially continuous electrical path(s) constituting closed electric circuit(s) around the axis of rotation and so forth is similarly as discussed with reference to FIGS. 7 through 10.

Although specific axisymmetric configurations have been discussed and depicted in the drawings, the present invention is not intended to be limited thereto, it being possible, with appropriate modification as necessary, to apply the foregoing description to any suitable axisymmetric configuration.

Figure 12:
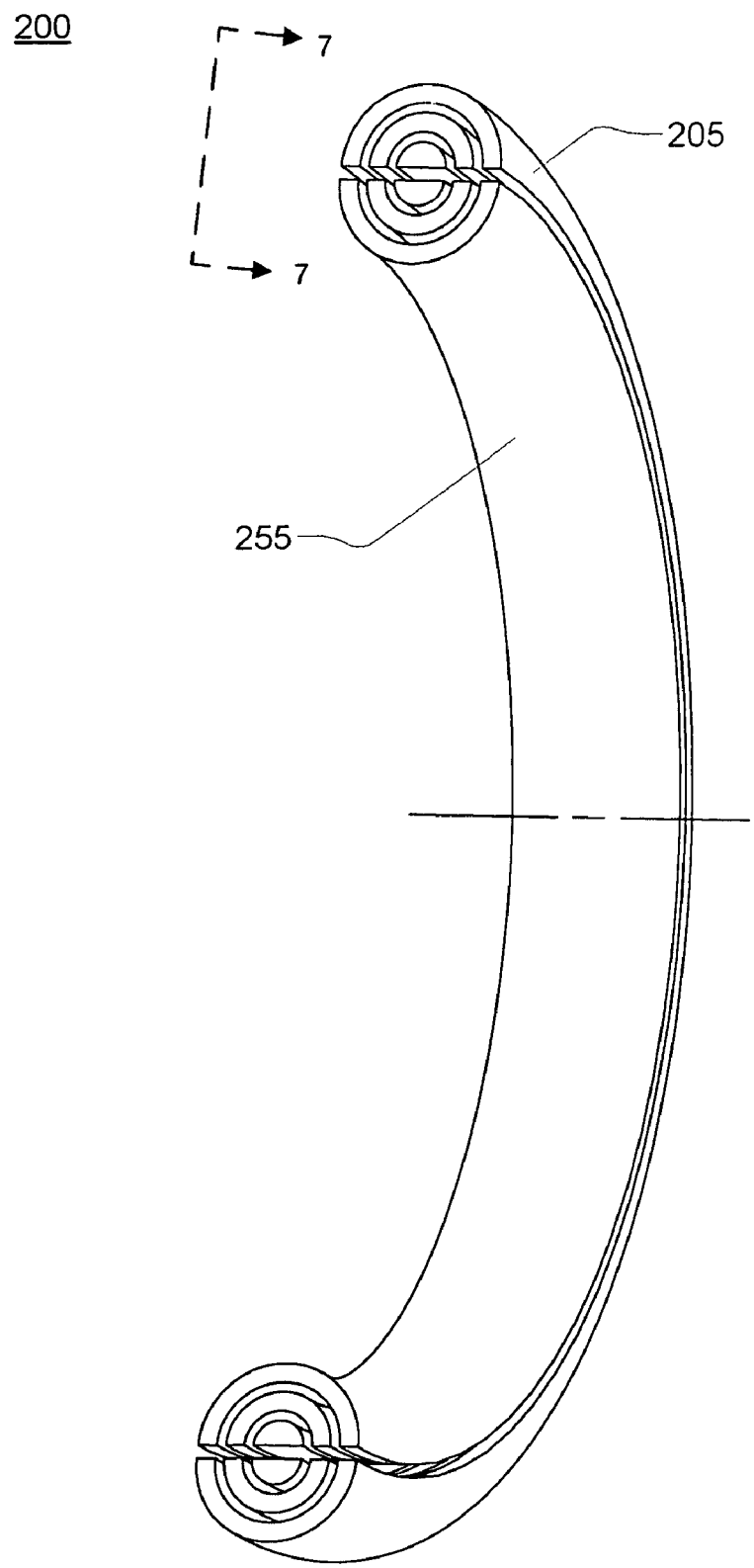
FIG. 12 is a perspective view of an idealized representation of cylindrical configuration 200 such as might be constituted or approximated by rotary transformers in accordance with embodiments of the present invention.

FIG. 12 is a perspective view of an idealized representation of a cylindrical configuration 200 such as might be constituted or approximated by rotary transformers in accordance with embodiments of the present invention. This configuration, in which half-couples 205, 255 of differing radii of curvature are arranged more or less concentrically in radially displaced fashion about the axis of rotation, is referred to as "cylindrical" because of the general shape of the volume of space swept out by airgap 202 which intervenes radially between and mutually separates half-couples 205, 255 and which is bounded by imaginary surfaces 245 and 295 (see FIG. 13). More rigorously, as described above with reference to FIG. 2, the volume of space swept out by airgap 202 during operation of the rotary transformer is annular, but as it is closer to being cylindrical than it is to being planar, this configuration is referred to herein as a cylindrical configuration. Note that although "radially displaced" is said, this is not to imply translational displacement since, as mentioned, the outer half-couple will in general be of larger radius of curvature than the inner half-couple; more accurately, the two half-couples (in this idealized illustrative example) can be thought of as being reflections of each other in polar coordinates across the airgap.

Figure 13:
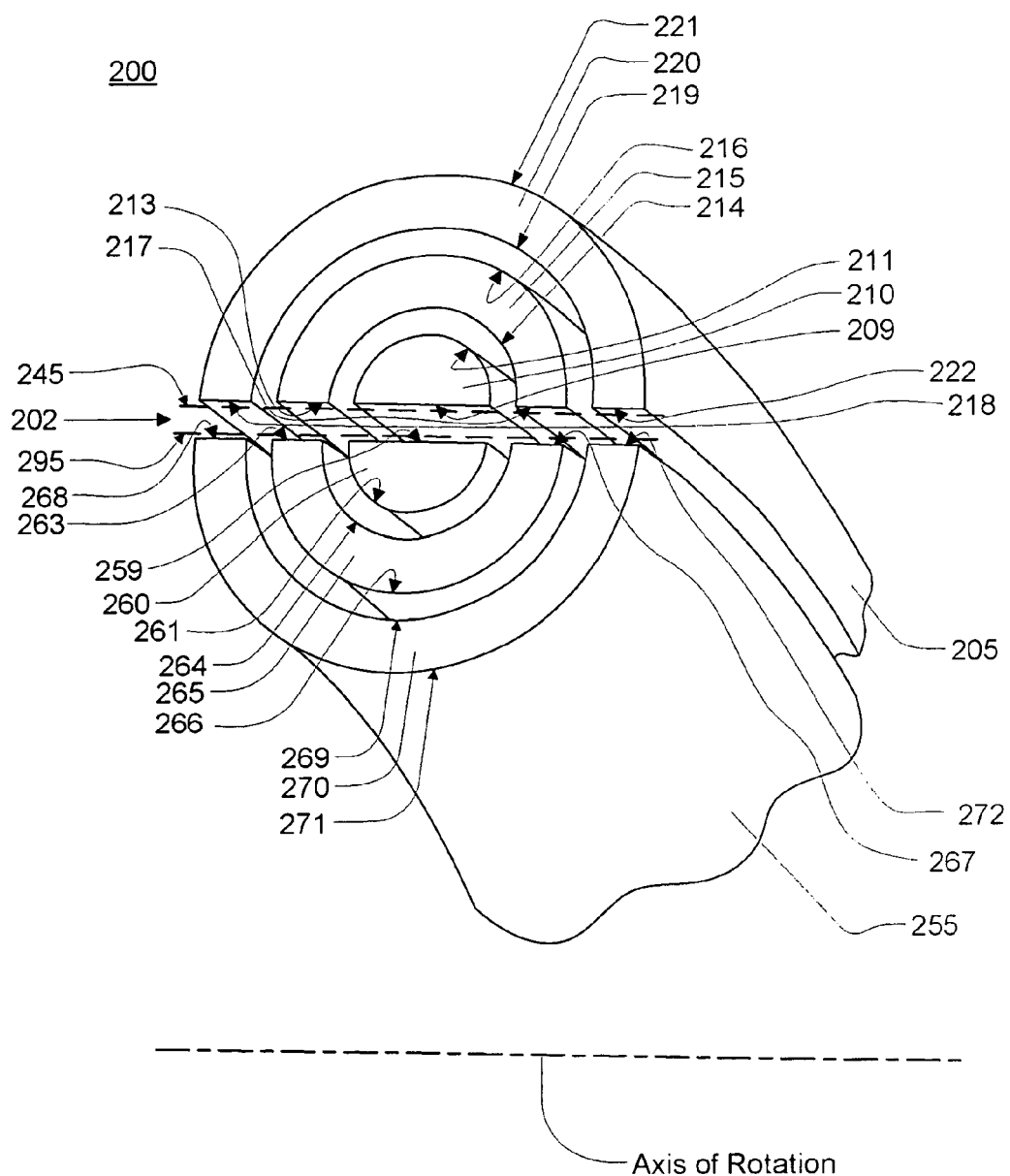
FIG. 13 is a meridional section of cylindrical configuration 200 shown in FIG. 12.

FIG. 13 is a meridional section of cylindrical configuration 200 shown in FIG. 12.

Cylindrical configuration 200 is a toroidal structure separated, so as to permit relative rotation, by airgap 202 into outer half-couple 205, which is bounded on the proximal (here and below, proximal and distal being as reckoned from a central location intermediate within airgap 202 as viewed in meridional section) side thereof by outer imaginary surface 245; and inner half-couple 255, which is bounded on the proximal side thereof by inner imaginary surface 295.

Outer half-couple 205 comprises three coaxial half-shells or layers 210, 215, 220, these being, in order from airgap 202: winding 210, core 215, and shield 220. Proximal surface 209 of winding 210 is shown as more or less conforming to outer imaginary surface 245; gaps of indeterminate thickness (intended to include the possibility of zero gap; i.e., contiguous arrangement) are shown as intervening between distal surface 211 of winding 210 and proximal surface 214 of core 215, and between distal surface 216 of core 215 and proximal surface 219 of shield 220; and outer half-couple 205 is bounded distally by distal surface 221 of shield 220. In the description given with reference to FIG. 13, note that even where half-cores and half-shields are meant, the prefix "half-" may sometimes be omitted for convenience of description.

Inner half-couple 255 comprises three coaxial half-shells or layers 260, 265, 270, these being, in order from airgap 202: winding 260, core 265, and shield 270. Proximal surface 259 of winding 260 is shown as more or less conforming to inner imaginary surface 295; gaps of indeterminate thickness (intended to include the possibility of zero gap; i.e., contiguous arrangement) are shown as intervening between distal surface 261 of winding 260 and proximal surface 264 of core 265, and between distal surface 266 of core 265 and proximal surface 269 of shield 270; and inner half-couple 255 is bounded distally by distal surface 271 of shield 270.

Winding 210 of outer half-couple 205 and winding 260 of inner half-couple 255 are arranged in mutual opposition across airgap 202 so as to permit mutual inductive coupling therebetween. Airgap interface 213 of outer core 215 appearing on the left side in FIG. 13 (hereinafter "outer core left airgap interface 213") is arranged in mutual opposition across airgap 202 with airgap interface 263 of inner core 265 appearing on the left side in FIG. 13 (hereinafter "inner core left airgap interface 263"), and airgap interface 217 of outer core 215 appearing on the right side in FIG. 13 (hereinafter "outer core right airgap interface 217") is arranged in mutual opposition across airgap 202 with airgap interface 267 of inner core 265 appearing on the right side in FIG. 13 (hereinafter "inner core right airgap interface 267") so as to complete and/or lower reluctance of a magnetic circuit linking magnetic flux produced around winding 210 of outer half-couple 205 and winding 260 of inner half-couple 255 in the fashion indicated above at the description given with reference to FIG. 2. To facilitate alignment of the magnetic field such that loops of magnetic flux lie in meridional planes, it is preferred that mutually opposed core-airgap interface surfaces be smooth, mutually parallel, and normal to the predominant direction of magnetic flux lines bridging the core airgap therebetween. Airgap interface 218 of outer shield 220 appearing on the left side in FIG. 13 (hereinafter "outer shield left airgap interface 218") is arranged in mutual opposition across airgap 202 with airgap interface 268 of inner shield 270 appearing on the left side in FIG. 13 (hereinafter "inner shield left airgap interface 268"), and airgap interface 222 of outer shield 220 appearing on the right side in FIG. 13 (hereinafter "outer shield right airgap interface 222") is arranged in mutual opposition across airgap 202 with airgap interface 272 of inner shield 270 appearing on the right side in FIG. 13 (hereinafter "inner shield right airgap interface 272") such that, except for airgap 202, shields 220, 270 more or less completely enshroud and enclose therewithin windings 210, 260 and cores 215, 265; i.e., windings 210, 260 and cores 215, 265 are, except for airgap 202, interior to and enclosed by shields 220, 270. Furthermore, airgap interfaces 218, 222 of shield 220 of outer half-couple 205, airgap interfaces 213, 217 of core 215 of outer half-couple 205, and proximal surface 209 of winding 210 of outer half-couple 205 all more or less conform to outer imaginary surface 245; and airgap interfaces 268, 272 of shield 270 of inner half-couple 255, airgap interfaces 263, 267 of core 265 of inner half-couple 255, and proximal surface 259 of winding 260 of inner half-couple 255 all more or less conform to inner imaginary surface 295.

Figure 14:
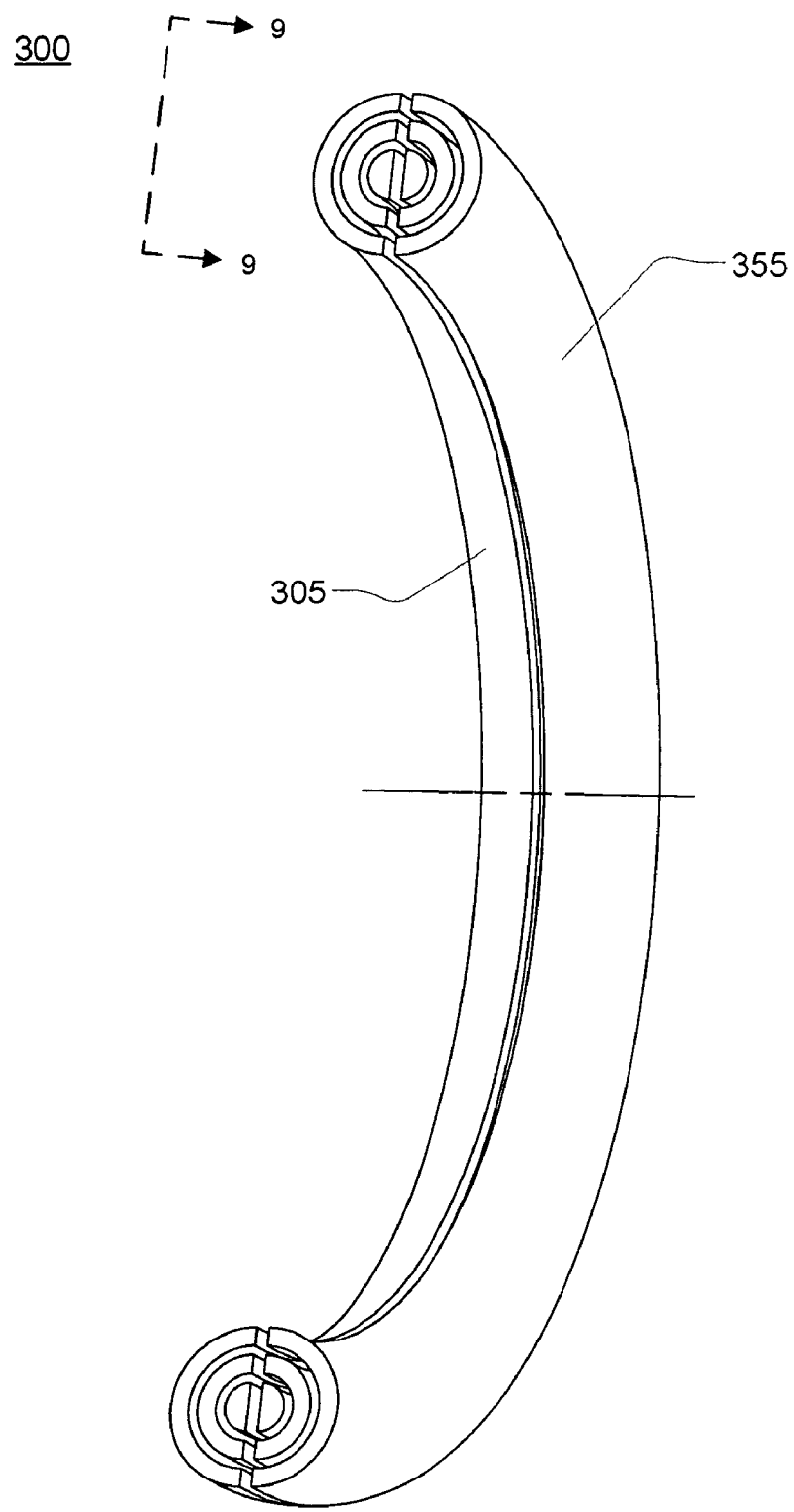
FIG. 14 is a perspective view of an idealized representation of a planar configuration 300 such as might be constituted or approximated by rotary transformers in accordance with embodiments of the present invention.

FIG. 14 is a perspective view of an idealized representation of a planar configuration 300 such as might be constituted or approximated by rotary transformers in accordance with embodiments of the present invention. This configuration, in which half-couples 305, 355 of identical radii of curvature are arranged side-by-side in axially displaced fashion along the axis of rotation, is referred to as "planar" because of the general shape of the volume of space swept out by airgap 302 which intervenes axially between and mutually separates half-couples 305, 355 and which is bounded by imaginary surfaces 345 and 395 (see FIG. 15). More rigorously, as described above with reference to FIG. 2, the volume of space swept out by airgap 302 during operation of the rotary transformer is annular, but as it is closer to being planar than it is to being cylindrical, this configuration is referred to herein as a planar configuration (or sometimes as a plane circular configuration). Note that although "axially displaced" is said, this is not to imply simple translational displacement; more accurately, the two half-couples (in this idealized illustrative example) can be thought of as being reflections of each other in rectangular coordinates across the airgap.

Figure 15:
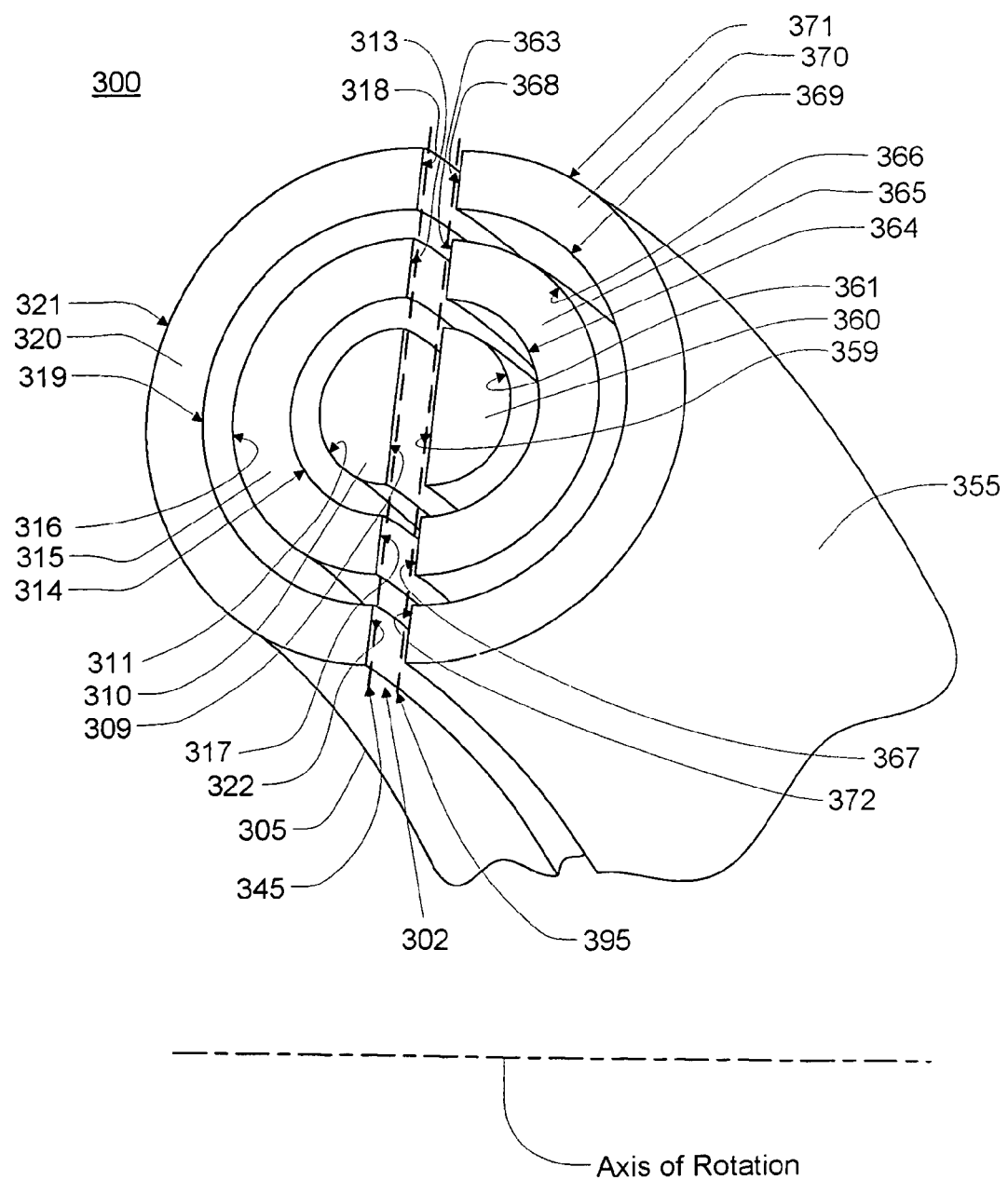
FIG. 15 is a meridional section of planar configuration 300 shown in FIG. 14.

FIG. 15 is a meridional section of planar configuration 300 shown in FIG. 14. Planar configuration 300 is a toroidal structure separated, so as to permit relative rotation, by airgap 302 into half-couple 305 appearing on the left side in FIGS. 14 and 15 (hereinafter "left half-couple 305"), which is bounded on the proximal (here and below, proximal and distal being as reckoned from a central location intermediate within airgap 302 as viewed in meridional section) side thereof by left imaginary surface 345; and half-couple 355 appearing on the right side in FIGS. 14 and 15 (hereinafter "right half-couple 355"), which is bounded on the proximal side thereof by right imaginary surface 395.

Left half-couple 305 comprises three coaxial half-shells or layers 310, 315, 320, these being, in order from airgap 302: winding 310, core 315, and shield 320. Proximal surface 309 of winding 310 is shown as more or less conforming to left imaginary surface 345; gaps of indeterminate thickness (intended to include the possibility of zero gap; i.e., contiguous arrangement) are shown as intervening between distal surface 311 of winding 310 and proximal surface 314 of core 315, and between distal surface 316 of core 315 and proximal surface 319 of shield 320; and left half-couple 305 is bounded distally by distal surface 321 of shield 320. In the description given with reference to FIG. 15, note that even where half-cores and half-shields are meant, the prefix "half-" may sometimes be omitted for convenience of description.

Right half-couple 355 comprises three coaxial half-shells or layers 360, 365, 370, these being, in order from airgap 302: winding 360, core 365, and shield 370. Proximal surface 359 of winding 360 is shown as more or less conforming to right imaginary surface 395; gaps of indeterminate thickness (intended to include the possibility of zero gap; i.e., contiguous arrangement) are shown as intervening between distal surface 361 of winding 360 and proximal surface 364 of core 365, and between distal surface 366 of core 365 and proximal surface 369 of shield 370; and right half-couple 355 is bounded distally by distal surface 371 of shield 370.

Winding 310 of left half-couple 305 and winding 360 of right half-couple 355 are arranged in mutual opposition across airgap 302 so as to permit mutual inductive coupling therebetween. Airgap interface 313 of left core 315 appearing on the side away from the axis of rotation in FIG. 15 (hereinafter "left core outer airgap interface 313") is arranged in mutual opposition across airgap 302 with airgap interface 363 of right core 365 appearing on the side away from the axis of rotation in FIG. 15 (hereinafter "right core outer airgap interface 363"), and airgap interface 317 of left core 315 appearing on the side toward the axis of rotation in FIG. 15 (hereinafter "left core inner airgap interface 317") is arranged in mutual opposition across airgap 302 with airgap interface 367 of right core 365 appearing on the side toward the axis of rotation in FIG. 15 (hereinafter "right core inner airgap interface 367") so as to complete and/or lower reluctance of a magnetic circuit linking magnetic flux produced around winding 310 of left half-couple 305 and winding 360 of right half-couple 355 in the fashion indicated above at the description given with reference to FIG. 2. To facilitate alignment of the magnetic field such that loops of magnetic flux lie in meridional planes, it is preferred that mutually opposed core-airgap interface surfaces be smooth, mutually parallel, and normal to the predominant direction of magnetic flux lines bridging the core airgap therebetween. Airgap interface 318 of left shield 320 appearing on the side away from the axis of rotation in FIG. 15 (hereinafter "left shield outer airgap interface 318") is arranged in mutual opposition across airgap 302 with airgap interface 368 of right shield 370 appearing on the side away from the axis of rotation in FIG. 15 (hereinafter "right shield outer airgap interface 370"), and airgap interface 322 of left shield 320 appearing on the side toward the axis of rotation in FIG. 15 (hereinafter "left shield inner airgap interface 322") is arranged in mutual opposition across airgap 302 with airgap interface 372 of right shield 370 appearing on the side toward the axis of rotation in FIG. 15 (hereinafter "right shield inner airgap interface 372") such that, except for airgap 302, shields 320, 370 more or less completely enshroud and enclose therewithin windings 310, 360 and cores 315, 365; i.e., windings 310, 360 and cores 315, 365 are, except for airgap 302, interior to and enclosed by shields 320, 370. Furthermore, airgap interfaces 318, 322 of shield 320 of left half-couple 305, airgap interfaces 313, 317 of core 315 of left half-couple 305, and proximal surface 309 of winding 310 of left half-couple 305 all more or less conform to left imaginary surface 345; and airgap interfaces 368, 372 of shield 370 of right half-couple 355, airgap interfaces 363, 367 of core 365 of right half-couple 355, and proximal surface 359 of winding 360 of right half-couple 355 all more or less conform to right imaginary surface 395.

Figure 16:
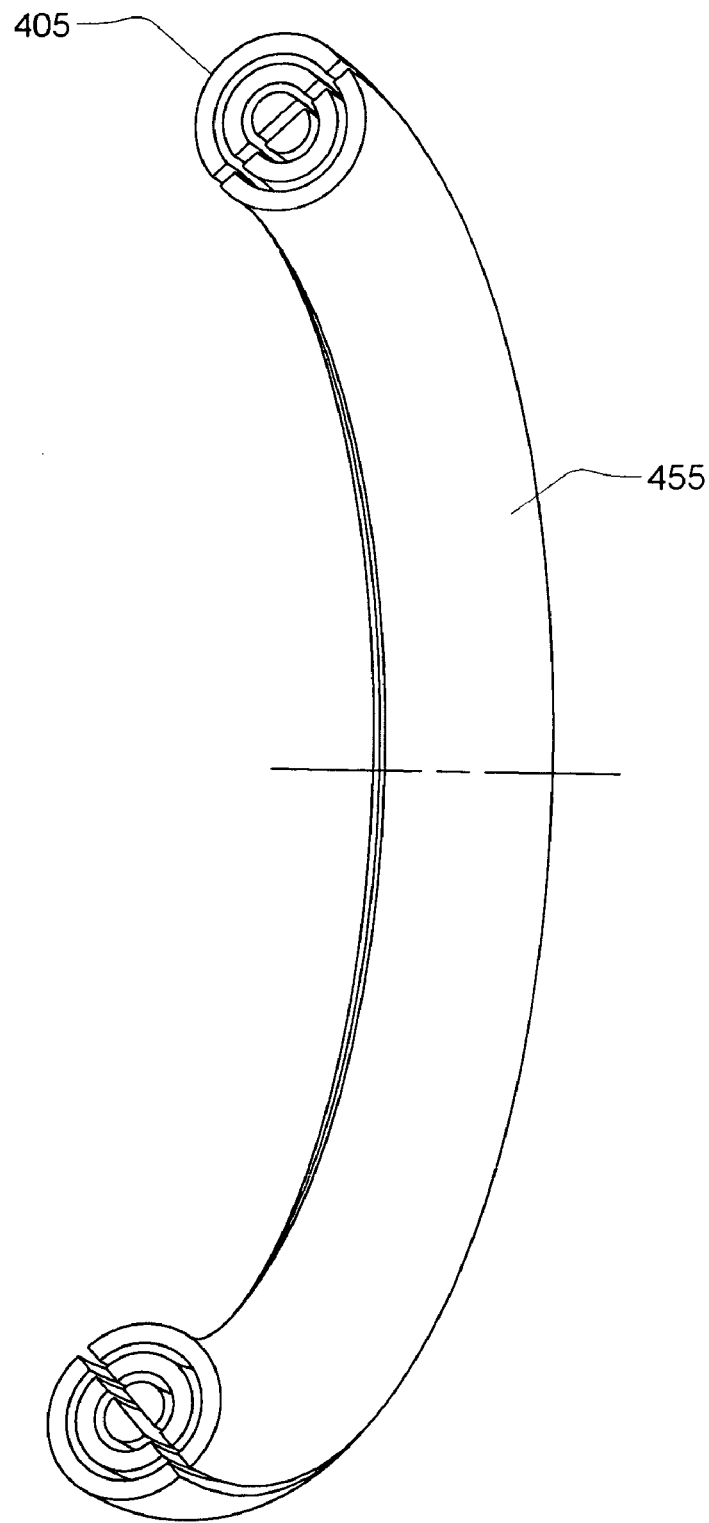
FIG. 16 is a perspective view of an idealized representation of a conical configuration 400 such as might be constituted or approximated by rotary transformers in accordance with embodiments of the present invention.

FIG. 16 is a perspective view of an idealized representation of a conical configuration 400 such as might be constituted or approximated by rotary transformers in accordance with embodiments of the present invention. This configuration, in which half-couples 405, 455 are arranged in both axially displaced and radially displaced fashion with respect to the axis of rotation, is referred to as "conical" because of the general shape of the volume of space swept out by the airgap which intervenes both axially and radially between and mutually separates half-couples 405, 455. As conical configuration 400 may be described in terms of radially displaced features in accordance with the description given with reference to cylindrical configuration 200 shown in FIG. 13, or may be described in terms of axially displaced features in accordance with the description given with reference to planar configuration 300 shown in FIG. 15, description of the meridional section of conical configuration 400 is omitted here for brevity but may be understood to be similar to the foregoing descriptions with reference to FIGS. 13 and 15 in which like-numbered parts have like function.

FIGS. 12 through 16 being idealized configurations presented for illustrative purposes, the various features depicted therein are not necessarily intended to indicate specific geometries or dimensions but are rather intended to suggest the overall schematic arrangement of those features in the context of a rotary transformer having cylindrical, planar, or conical configuration. That is, where practical, a power coupling device might be fabricated exactly as depicted at any of FIGS. 12 through 16, e.g., such that a solid single-turn winding is disposed within a homogeneous half-core having C-shaped cross-section, and these are in turn nested within a homogeneous half-shield having C-shaped cross-section, to form each of two semitoroidal half-couples as depicted in the drawings; but more generally, where "winding," "core," and "shield" (or "half-core" or "half-shield") are said, this is not to necessarily imply that these must be continuous or homogeneous, or that structures having any particular dimensions or composition must necessarily occupy the regions representing each of these at FIGS. 12 through 16, these terms rather indicating schematic or conceptual layers serving respective functions of winding, core, and shield in the rotary transformer, without regard to dimensions, geometry, composition, structure, or the like, except where otherwise specifically indicated. Moreover, at least with regard to the descriptions given with reference to idealized configurations at FIGS. 12 through 16, except where otherwise clear from context, "winding" is interchangeable with "winding layer," "core" is interchangeable with "core layer," and "shield" is interchangeable with "shield layer."

At each of FIGS. 12 through 16, respective half-couples constituting a rotary transformer are reflections of each other across a cylindrical, planar, or conical airgap (i.e., there is symmetry with respect to an imaginary surface at the midline of the airgap), and arrangement of windings, cores, and shields is furthermore axisymmetric (e.g., toroidal), the axis of symmetry being collinear with the axis of rotation. Here, windings and shields preferably support flow of current circumferentially about the axis of rotation (e.g., along circles coaxial with toroid major circles), and the winding/core arrangement preferably causes loops of magnetic flux mutually linking the half-couples to lie in meridional planes (e.g., planes of toroid minor circles). Here, where the core layer is absent or does not have significant reluctance-lowering ability, winding orientation will dominate and so is preferably such as to cause loops of magnetic flux mutually linking half-couples to lie in meridional planes; but where the core layer is present and the material employed therein has significant reluctance-lowering ability, distribution of such reluctance-lowering material within the core layer will dominate and so is preferably such as to cause loops of magnetic flux mutually linking half-couples to lie in meridional planes. Although windings in FIGS. 12 through 16 are represented at each half-couple by only a single feature having semicircular cross-section disposed within the single recess of a core having C-shaped cross-section, these should be understood to schematically represent any suitable winding/core arrangement, including arrangements in which additional arm-like pole members intervene between multiple windings such as, for example, at the E-core configurations in FIGS. 6 through 10 and at inset iii of FIG. 11, or at the triple-winding configurations suitable for three-phase AC at insets iv and v in FIG. 11. Although shields in FIGS. 12 through 16 are represented by two-part wraparound shields having shield airgaps that are adjacent to the core airgaps, these should be understood to schematically represent any suitable shield configuration, including any of the configurations (e.g., single-part, multipartite, adjacent-airgap, nonadjacent-airgap, cutback, wraparound, etc.) described with reference to FIGS. 6 through 11.

That is, it is sufficient in some embodiments of the present invention for shield(s) 220, 270, 320, 370 to be such that electrically conductive material is present at least where magnetic flux from winding(s) 210, 260, 310, 360 and/or core(s) 215, 265, 315, 365 escapes those interior layers to impinge on shield layer(s) and/or is misaligned. Here, "escape of flux" refers to failure of magnetic flux from winding(s) 210, 260, 310, 360 to be shunted and contained within core(s) 215, 265, 315, 365; i.e., whereas presence of reluctance-lowering material in core(s) 215, 265, 315, 365 around winding(s) 210, 260, 310, 360 may be expected to reduce leakage inductance and prevent flux from escaping beyond core(s) 215, 265, 315, 365, absence or insufficiency of reluctance-lowering material, discontinuities in reluctance distribution (e.g., airgaps), and the like may allow flux to escape and impinge on the shield layer. Here, "misalignment of flux" refers to a situation in which there are magnetic flux loops that do not lie in meridional planes; i.e., whereas flux loops may be expected to circulate about minor circles lying in meridional planes when current flows circumferentially along a major circle in a more or less toroidal system such as that shown in FIGS. 1 and 2, discontinuities in reluctance distribution (e.g., airgaps), deviation from axisymmetry, and the like may cause the planes in which those flux loops lie to be other than meridional planes, meaning that such misaligned flux loops would have a component perpendicular to meridional planes, which is to say that there would be a flux component in the rotary transformer circumferential direction.

For example, in an embodiment of the present invention in which there is no core layer, or in which the reluctance of cores 215, 265, 315, 365 is not low enough to significantly shunt magnetic flux therewithin, as flux would escape essentially everywhere (the core airgap would essentially extend into and occupy the entire core layer), electrically conductive material would in such embodiments of the present invention need to be essentially everywhere throughout the shield layer except for small shield airgap(s) as necessary to permit relative rotation.

But in embodiments of the present invention in which there is an effective core layer such that reluctance of cores 215, 265, 315, 365 is low enough to significantly shunt magnetic flux therewithin, provided that the core material distribution is reasonably axisymmetric, it may be sufficient for there to be electrically conductive material present only where fringing fields escape from core airgaps as shown at regions 103 in FIG. 5. And because core airgaps run along the circumference between half-couples 205, 255, 305, 355 of the rotary transformer on either side in a direction perpendicular to the direction of an imaginary line drawn between corresponding parts of respective half-couples (e.g., as viewed in meridional section), it may be sufficient for electrically conductive material to be present only in circumferential zone(s) near core airgaps.

For example, such circumferential zone(s) of electrically conductive material might be disposed adjacent cores 215, 265 of cylindrical configuration 200, near where left airgap interface 213 of outer half-couple 205 opposes left airgap interface 268 of inner half-couple 255 and near where right airgap interface 217 of outer half-couple 205 opposes right airgap interface 267 of inner half-couple 255; or might be disposed adjacent cores 315, 365 of planar configuration 300, near where outer airgap interface 313 of left half-couple 305 opposes outer airgap interface 368 of left half-couple 305 and near where inner airgap interface 317 of left half-couple 305 opposes inner airgap interface 367 of right half-couple 355.

Such circumferential zones of electrically conductive material correspond more or less to fringe field canceling zones described above, and correspond more or less to darkened regions indicating flow of field-canceling current at the finite element simulations in FIGS. 7 through 10. From the definition of "distal" given above as being reckoned from a central location intermediate within the airgap as viewed in meridional section, such circumferential zone(s) of electrically conductive material might be described as being located in distally adjacent fashion with respect to the core airgaps.

For example, referring to FIGS. 12 and 13 (cylindrical configuration 200) and taking the case of an adjacent-airgap multipartite shield similar to that shown in FIG. 7, this might mean two circumferential zones of electrically conductive material at each of shields 220, 270 (corresponding to half-shields 120, 170 in FIG. 7), for a total of four circumferential zones of electrically conductive material. Or with continued reference to FIGS. 12 and 13 (cylindrical configuration 200) but taking instead the case of a nonadjacent-airgap shield similar to that shown in FIG. 8 or FIG. 10, this might mean two circumferential zones of electrically conductive material at only the lower shield 270 (corresponding to half-shield 170 in FIGS. 8 and 10), for a total of two circumferential zones of electrically conductive material. Although specific description has here been made with respect to cylindrical configuration 200 shown in FIGS. 12 and 13, similar characteristics will apply to planar configuration 300 shown in FIGS. 14 and 15, and to conical configuration 400 shown in FIG. 16.

That is, for nonadjacent-airgap configurations such as those shown in FIGS. 9 through 10, where shield airgap(s) are large but are far enough from core airgap(s) to allow field-canceling currents produced by flux escaping from core airgap(s) to flow in the electrically conductive material of the shield(s) in such fashion as to cancel the effects of the leaked flux before those effects would reach shield airgap(s), i.e., fringe field canceling zone(s) do not extend as far as shield airgap(s), there might be adequate shielding even where electrically conductive material is present only in circumferential zones as described above. This being the case, adequate shielding may be possible even where a cutback-type shield of the type shown in FIG. 9 is employed, or where one half-shield is omitted such that only a single-part shield such as lower half-shield 170 shown in FIGS. 8 and 10 is employed.

Or in embodiments of the present invention in which there is an effective core layer such that reluctance of cores 215, 265, 315, 365 is low enough to significantly shunt magnetic flux therewithin but in which there may be local misalignment of flux (e.g., because of failure of cores 215, 265, 315, 365 to conform to axisymmetry), it may be sufficient for shield(s) 220, 270, 320, 370 to be such that electrically conductive material is present only near location(s) at which there is such misalignment of flux, provided that such location(s) is/are distant enough from shield airgap(s) to allow field-canceling currents to flow in the electrically conductive material of shield(s) 220, 270, 320, 370 in such fashion as to cancel the effects of the leaked flux before those effects would reach shield airgap(s) or other such shield discontinuity or discontinuities (and provided that thickness of shield thereat is sufficient to prevent effects of leaked flux from reaching shield outer surface(s)).

Consistent with general description concerning preferred ranges for shield thickness(es) and electrical conductivity or conductivities given with reference to FIGS. 7 through 10, for the shield shown in FIGS. 12 through 16 as well it will similarly be preferred that shield thickness at locations where magnetic flux impinges thereon be sufficient to allow field-canceling currents to flow in the electrically conductive material of the shield(s) in such fashion as to cancel the effects of the impinging flux before those effects would reach the shield outer surface(s) and/or shield airgap(s). Except where otherwise clear from context, all of the preferred ranges and accompanying description given with reference to FIGS. 7 through 10 may be understood to apply to the configurations shown in FIGS. 12 through 16.

As mentioned above, FIGS. 12 through 16 are idealized configurations presented for illustrative purposes, and while the present invention may be carried out in the context of configurations closely resembling the configurations depicted, it is also possible to carry out aspects of the invention in the context of configurations that vary considerably from the configurations depicted while still remaining within the scope of aspects of the present invention. Note that while a few representative toroidal solids of revolution have been chosen for purposes of illustration, differently shaped or oriented toroidal solids of revolution, or annular solids of revolution, or toroids or solids of revolution based on any other suitable cross-section, might just as easily have been used; and as these are being presented for purposes of illustration and merely as a convenient means for introducing and describing various features of some embodiments of the present invention, the present invention should not be understood to be limited, for example, to solids of revolution having circular cross-section.

Next described are practical examples of how the overall axisymmetric structure of the power coupling device may be obtained in practice using commercially available parts and methods. For example, where large-diameter ferrite rings or the like are not commercially available, it may be desirable to fabricate cores from multiplicities of C-core segments and/or other such commercially available core segments. While any appropriate manufacturing method may of course be used to obtain any of the various components of the power coupling device; including, without limitation, molding, casting, extrusion, and so forth, the examples described below with reference to FIGS. 17 and 18 each employ mutually opposed annular cores built up from a multiplicity of ferrite core segments arranged in mutually adjacent fashion so as to collectively approximate a substantially annular and/or semitoroidal core configuration, a cylindrical configuration being shown at FIG. 17 and a planar configuration being shown at FIG. 18. Here, "cylindrical" and "planar" refer to the shape of the volume of space occupied by the airgap intervening between stationary and moving sides of the rotary transformer; as described above with reference to FIG. 1, the cylindrical configuration is alternatively referred to as "radially displaced," and the planar configuration is alternatively referred to as "axially displaced."

Figure 17:
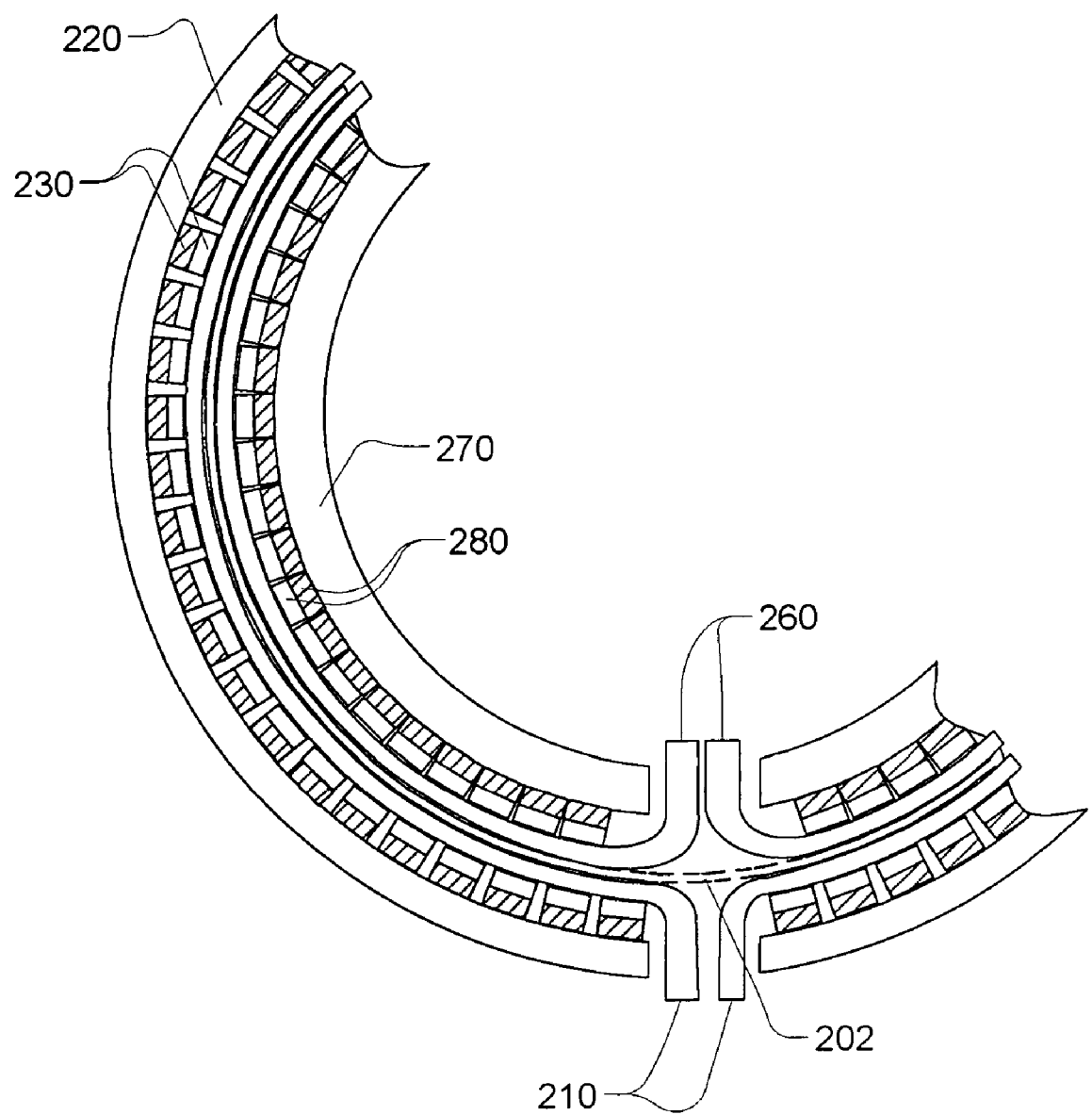
FIG. 17 is a sectional view of a practical example showing how a shielded power coupling device having cylindrical configuration may be fabricated through arrangement of multiplicities of ferrite core segments 230, 280 in mutually adjacent fashion so as to collectively approximate mutually opposed cores which are substantially annular and/or semitoroidal.

Referring now to FIG. 17, this is a sectional view of a practical example showing how a shielded power coupling device having cylindrical configuration approximating that shown in FIGS. 12 and 13 may be fabricated in accordance with one or more embodiments of the present invention through arrangement of a multiplicity of commercially available ferrite core segments 230, 280 in mutually adjacent fashion so as to collectively approximate mutually opposed cores which are substantially annular and/or semitoroidal, cross-sectional profile being similar to that shown in FIG. 5 or FIG. 13. At FIG. 17, the power coupling device is shown as cut in half so that its constituent components (windings, cores, and shields) can be seen. In the description given with reference to FIG. 17, note that even where half-cores and half-shields are meant, the prefix "half-" may sometimes be omitted for convenience of description.

Here, the power coupling device includes primary core 230 and secondary core 280. Primary core 230 defines a primary core recess or groove in which primary electrically conductive winding 210 is situated. Secondary core 280 defines a secondary core recess or groove in which secondary electrically conductive winding 260 is situated. In the embodiment shown at FIG. 17, primary core 230 and secondary core 280 each have substantially semitoroidal configuration, i.e. are shaped as half-toroidal shells. In the present embodiment, the primary and secondary core recesses defined by cores 230 and 280 are substantially annular. Here, although the outer core has been taken to correspond to a rotary transformer primary core, and the inner core has been taken to correspond to a rotary transformer secondary core; the inner core might just as easily have been taken to correspond to a rotary transformer primary core, and the outer core might just as easily have been taken to correspond to a rotary transformer secondary core.

As seen in FIG. 17, secondary core 280 is disposed adjacent primary core 230, the primary and secondary cores being arranged so as to form an airgap 202 therebetween (although not visible in the section shown in the drawing, ends of arm-like pole members of C-core segments making up cores 230, 280 partially wrap around windings 210, 260 to reach as far as airgap 202). The secondary core recess is disposed opposite the primary core recess and is spaced apart therefrom. The airgap 202 permits relative rotation of the cores about an axis of rotation. In this way, at least one of the cores may be disposed on a rotating unit of a system, for example on the rotating gantry in a CT scanner, so as to rotate together with the rotating unit and deliver power to the unit. The cores might, for example, be made of a magnetically permeable material, which may include, but is not limited to, ferrite, silicon iron, nickel iron alloy, stainless steel, and cobalt iron alloy.

In the embodiment illustrated in FIG. 17, primary core 230 and secondary core 280 have different radii of curvature about a common axis of axisymmetry, airgap 202 intervening radially between primary core 230 and secondary core 280, and the axis of axisymmetry being substantially collinear with the axis of rotation of the rotary transformer which constitutes the power coupling device. That is, in the configuration shown at FIG. 17, respective half-couples constituting a rotary transformer are reflections of each other across a cylindrical airgap (i.e., there is symmetry with respect to an imaginary surface at the midline of the airgap), and arrangement of windings, cores, and shields is furthermore axisymmetric (e.g., toroidal), the axis of symmetry being collinear with the axis of rotation.

The shielded power coupling device shown in FIG. 17 may be understood, in its simplest form, as two arcuate electrically conductive elements 210 and 260 serving as windings, surrounded by ferrite segments constituting toroidal half-shells 230 and 280 serving as cores, with shields 220 and 270 at the periphery thereof as described below. Semitoroidal cores 230 and 280 at FIG. 17 may be of substantially C-shaped cross-section or may be of E-shaped cross-section, or may be of any other suitable configuration, including, without limitation, the configurations of any of the cores described above with reference to FIGS. 6 through 16. Note that while windings 210 and 260 are shown as single-turn windings in the embodiment shown at FIG. 17, this is purely for illustrative purposes, as fractional- and/or multiple-turn windings are also within the scope of various aspects of the present invention as described above with reference to FIG. 1. Furthermore, where core(s) having E-shaped cross-section or other such cross-section facilitating formation of multiple recesses at each the primary and the secondary side of the rotary transformer are employed, multiple windings may be disposed at each the primary and the secondary side so as to permit application of alternating current (e.g., two-phase, three-phase, polyphase, etc.) in such manner as to cause the net instantaneous current flowing through the primary windings to be substantially zero (i.e., such that respective magnetization currents at respective primary windings mutually cancel), as was described above with reference to FIGS. 6 through 11. At FIG. 17, note that whereas toroidal core half-shells 230 and 280 are shown with ferrite core segments omitted in the regions where winding leads 210 and 260 enter and exit therefrom, this is only for convenience of illustration, it being preferred from the standpoint of alignment of magnetic flux and therefore of operation of the shield that there be minimal interruption in axisymmetry of the ferrite core segment arrangement, as will be explained in further detail with reference to FIGS. 19 through 22.

At FIG. 17, the primary and secondary cores are, except for shield airgaps permitting relative movement, collectively enshrouded by electrically conductive shields 220 and 270 (although not visible in the section shown in the drawing, half-shields 220 and 270 partially wrap around the winding/core system to reach as far as airgap 202). At FIG. 17, note that whereas electrically conductive shields 220 and 270 are shown as broken in the circumferential direction in the regions where winding leads 210 and 260 enter and exit core half-shells 230 and 280, this is only for convenience of illustration, it being preferred from the standpoint of operation of the shield that half-shields 220 and 270 have electrically conductive material wherever magnetic flux escaping from the winding/core system would impinge thereon, e.g., at fringe field canceling zones at peripheries of core airgaps (e.g., in distally adjacent fashion with respect to the core airgaps, as described above with reference to FIGS. 12 through 16; and as the core airgaps run the entire length of the circumference, such fringe field canceling zones will preferably run the entire length of the circumference alongside the core airgaps); and it being preferred from the standpoint of operation of the shield that half-shields 220 and 270 comprise electrically conductive material forming substantially continuous electrical path(s) constituting closed electric circuit(s) around the axis of rotation, as was explained above with reference to FIGS. 5 through 16.

In the configuration shown at FIG. 17, windings and shields preferably support flow of current circumferentially about the axis of rotation (e.g., along circle(s) coaxial with toroid major circle(s)), and the winding/core arrangement preferably causes loops of magnetic flux mutually linking the half-couples to lie in meridional planes (e.g., planes of toroid minor circles). Consistent with general description concerning preferred ranges for shield thickness(es) and electrical conductivity or conductivities given with reference to FIGS. 7 through 10, for half-shields 220 and 270 shown in FIG. 17 as well it will similarly be preferred that shield thickness at locations where magnetic flux impinges thereon be sufficient to allow field-canceling currents to flow in the electrically conductive material of the shield(s) in such fashion as to cancel the effects of the impinging flux before those effects would reach the shield outer surface(s) and/or shield airgap(s). Except where otherwise clear from context, all of the preferred ranges and accompanying description given with reference to FIGS. 7 through 10 may be understood to apply to the configuration shown in FIG. 17. Although the shield depicted at FIG. 17 is a two-part wraparound shield comprising half-shields 220 and 270 having shield airgaps adjacent to core airgaps, it is alternatively or additionally possible to employ any suitable shield configuration, including any of the configurations (e.g., single-part, multipartite, adjacent-airgap, nonadjacent-airgap, cutback, wraparound, etc.) described with reference to FIGS. 6 through 11.

Figure 18:
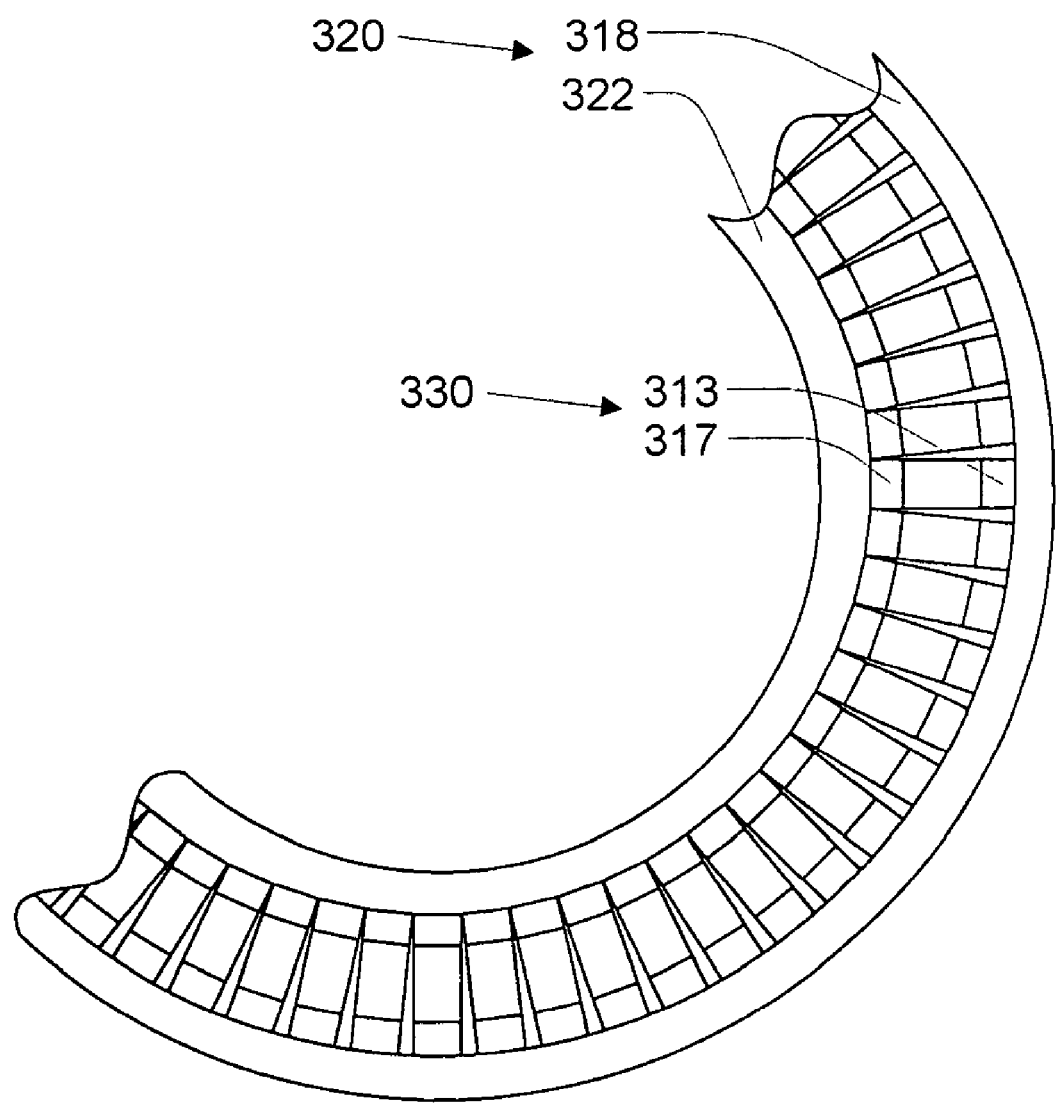
FIG. 18 is a side view of a practical example showing how a shielded power coupling device having planar configuration may be fabricated through arrangement of a multiplicity of ferrite core segments 330, 380 in mutually adjacent fashion so as to collectively approximate mutually opposed cores which are substantially annular and/or semitoroidal.

Referring now to FIG. 18, this is a side view of a practical example showing how a shielded power coupling device having planar configuration approximating that shown in FIGS. 14 and 15 may be fabricated in accordance with one or more embodiments of the present invention through arrangement of a multiplicity of commercially available ferrite core segments 330, 380 in mutually adjacent fashion so as to collectively approximate mutually opposed cores which are substantially annular and/or semitoroidal. At FIG. 18, note that only one side (e.g., the primary side) of the rotary transformer making up the shielded power coupling device is shown; moreover, only the core and shield are visible, windings that would be routed along the core recess during assembly being omitted from the present drawing. To complete assembly of the axially displaced rotary transformer, the other side (e.g., the secondary side) would be assembled in similar fashion as the side thereof which is shown in FIG. 18, except that this other side would need to be essentially a mirror image of the side shown in FIG. 18 so that when windings are placed in the recesses thereof and the open faces of the semitoroidal cores and windings are made to face each other in mutual opposition, a cross-sectional profile such as that shown in FIG. 5 or FIG. 15 is obtained. When a rotary transformer having planar configuration as in the present embodiment is assembled in such fashion, the primary core and the secondary core will have identical radii of curvature about a common axis of axisymmetry, an airgap intervening axially between the primary core and the secondary core such that the primary core and the secondary core are arranged side-by-side, and the axis of axisymmetry being substantially collinear with the axis of rotation of the power coupling device. In the description given with reference to FIG. 18, note that even where half-cores and half-shields are meant, the prefix "half-" may sometimes be omitted for convenience of description.

Here, such a power coupling device would, after assembly as described above, include primary core 330 and secondary core 380. In such case, primary core 330 would define a primary core recess or groove in which primary electrically conductive winding 310 would be situated. Secondary core 380 would define a secondary core recess or groove in which secondary electrically conductive winding 360 would be situated. In the embodiment shown at FIG. 18, primary core 330 and secondary core 380 would, after assembly as described above, each have substantially semitoroidal configuration, i.e. these would be shaped as half-toroidal shells. In the present embodiment, the primary and secondary core recesses defined by cores 330 and 380 would, after assembly as described above, be substantially annular. Here, the half-core shown in FIG. 18 might be taken to be, say, the left core as viewed edge-on when two mirror-image half-cores are assembled side-by-side in axially displaced fashion together with respective windings and shields to obtain cross-sectional profile as shown in FIG. 5 or FIG. 15 as described above, and might, for example, correspond to a rotary transformer primary core; and the half-core not shown in the drawing might be taken to be, say, the right core as viewed edge-on when two mirror-image half-cores are assembled side-by-side in axially displaced fashion as described above, and might, for example, correspond to a rotary transformer secondary core. Alternatively, the right core might correspond to a rotary transformer primary core, and the left core might correspond to a rotary transformer secondary core. At FIG. 18, where left core 330 is shown as having airgap interface 313 and airgap interface 317, and where left shield 320 is shown as having airgap interface 318 and airgap interface 322, these are as described above with reference to FIG. 15.

After inserting windings and assembling mirror-image half-couples such as that shown in FIG. 18 to obtain cross-sectional profile as shown in FIG. 5 or FIG. 15 as described above, secondary core 380 would be disposed adjacent primary core 330, the primary and secondary cores being arranged so as to form an airgap 302 therebetween. The secondary core recess would be disposed opposite the primary core recess and would be spaced apart therefrom. The airgap 302 permits relative rotation of the cores about an axis of rotation. In this way, at least one of the cores may be disposed on a rotating unit of a system, for example on the rotating gantry in a CT scanner, so as to rotate together with the rotating unit and deliver power to the unit. The cores might, for example, be made of a magnetically permeable material, which may include, but is not limited to, ferrite, silicon iron, nickel iron alloy, stainless steel, and cobalt iron alloy.

After inserting windings and assembling mirror-image half-couples such as that shown in FIG. 18 as described above, primary core 330 and secondary core 380 would have identical radii of curvature about a common axis of axisymmetry, airgap 302 intervening axially between primary core 330 and secondary core 380, and the axis of axisymmetry being substantially collinear with the axis of rotation of the rotary transformer which constitutes the power coupling device. That is, after assembling mirror-image half-couples as described above, respective half-couples constituting the rotary transformer will be reflections of each other across a planar airgap (i.e., there is symmetry with respect to an imaginary surface at the midline of the airgap), and arrangement of windings, cores, and shields is furthermore axisymmetric (e.g., toroidal), the axis of symmetry being collinear with the axis of rotation.

The shielded power coupling device obtained by inserting windings and assembling mirror-image half-couples such as that shown in FIG. 18 to obtain a cross-sectional profile as shown in FIG. 5 or FIG. 15 as described above may be understood, in its simplest form, as two arcuate electrically conductive elements 310 and 360 serving as windings, surrounded by ferrite segments constituting toroidal half-shells 330 and 380 serving as cores, with shields 320 and 370 at the periphery thereof as described below. Semitoroidal cores 330 and 380 in the assembled power coupling device may be of substantially C-shaped cross-section or may be of E-shaped cross-section, or may be of any other suitable configuration, including, without limitation, the configurations of any of the cores described above with reference to FIGS. 6 through 16. As windings 310 and 360, any of single-turn windings, or fractional-turn windings, and/or multiple-turn windings may be employed as described above with reference to FIG. 1. Furthermore, where core(s) having E-shaped cross-section or other such cross-section facilitating formation of multiple recesses at each the primary and the secondary side of the rotary transformer are employed, multiple windings may be disposed at each the primary and the secondary side so as to permit application of alternating current (e.g., two-phase, three-phase, polyphase, etc.) in such manner as to cause the net instantaneous current flowing through the primary windings to be substantially zero (i.e., such that respective magnetization currents at respective primary windings mutually cancel), as was described above with reference to FIGS. 6 through 11. With respect to the regions where winding leads 310 and 360 enter and exit toroidal core half-shells 330 and 380, it is preferred from the standpoint of alignment of magnetic flux and therefore of operation of the shield that there be minimal interruption in axisymmetry of the ferrite core segment arrangement, as will be explained in further detail with reference to FIGS. 19 through 22.

After inserting windings and assembling mirror-image half-couples such as that shown in FIG. 18 as described above, the primary and secondary cores will be, except for shield airgaps permitting relative movement, collectively enshrouded by electrically conductive shields 320 and 370. After assembly as described above, it is preferred from the standpoint of operation of the shield that half-shields 320 and 370 have electrically conductive material wherever magnetic flux escaping from the winding/core system would impinge thereon, e.g., at fringe field canceling zones at peripheries of core airgaps (e.g., in distally adjacent fashion with respect to the core airgaps, as described above with reference to FIGS. 12 through 16; and as the core airgaps run the entire length of the circumference, such fringe field canceling zones will preferably run the entire length of the circumference alongside the core airgaps); and it is preferred from the standpoint of operation of the shield that half-shields 320 and 370 comprise electrically conductive material forming substantially continuous electrical path(s) constituting closed electric circuit (s) around the axis of rotation, as was explained above with reference to FIGS. 5 through 16.

In the configuration obtained after inserting windings and assembling mirror-image half-couples such as that shown in FIG. 18 to obtain cross-sectional profile as shown in FIG. 5 or FIG. 15 as described above, windings and shields preferably support flow of current circumferentially about the axis of rotation (e.g., along circles coaxial with toroid major circles), and the winding/core arrangement preferably causes loops of magnetic flux mutually linking the half-couples to lie in meridional planes (e.g., planes of toroid minor circles). Consistent with general description concerning preferred ranges for shield thickness(es) and electrical conductivity or conductivities given with reference to FIGS. 7 through 10, for half-shields 320 and 370 as well it will similarly be preferred that shield thickness at locations where magnetic flux impinges thereon be sufficient to allow field-canceling currents to flow in the electrically conductive material of the shield(s) in such fashion as to cancel the effects of the impinging flux before those effects would reach shield outer surface(s) and/or shield airgap(s). Except where otherwise clear from context, all of the preferred ranges and accompanying description given with reference to FIGS. 7 through 10 may be understood to apply to the configuration obtained after inserting windings and assembling mirror-image half-couples such as that shown in FIG. 18 as described above. Although the shield in the configuration obtained after assembly as described above will be a two-part wraparound shield comprising half-shields 320 and 370 having shield airgaps adjacent to core airgaps, it is alternatively or additionally possible to employ any suitable shield configuration, including any of the configurations (e.g., single-part, multipartite, adjacent-airgap, nonadjacent-airgap, cutback, wraparound, etc.) described with reference to FIGS. 6 through 11.

Practical examples showing how shielded power coupling devices having cylindrical and planar configuration may be fabricated through arrangement of multiplicities of ferrite core segments have been described with reference to FIGS. 17 and 18; practical fabrication of a shielded power coupling devices having conical configuration through arrangement of multiplicities of ferrite core segments, although not described, is also possible and within the scope of the present invention.

Figure 19:
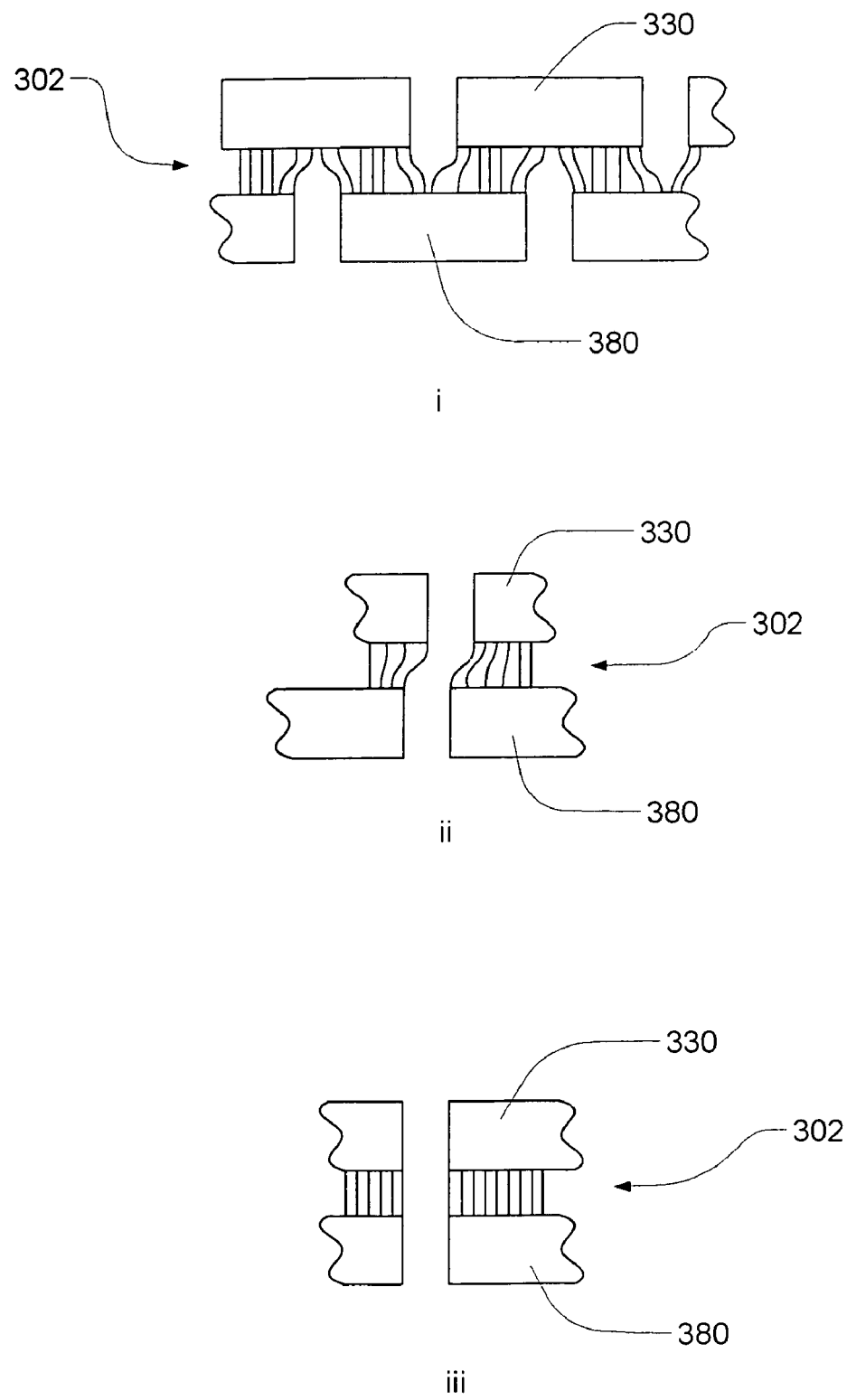
FIG. 19, in which a power coupling device of planar configuration having mutually opposed cores respectively made up of multiplicities of ferrite core segments 330, 380 as shown in FIG. 18 is drawn as would be seen if viewed edge-on within the plane of the paper at FIG. 18, shows how lines of magnetic flux bridging core airgap 302 might alternately become aligned and misaligned during rotation of the power coupling device.

Referring now to FIG. 19, here, a power coupling device of planar configuration having mutually opposed cores respectively made up of multiplicities of ferrite core segments 330, 380 as described with reference to FIG. 18 is drawn as would be seen if viewed edge-on within the plane of the paper at FIG. 18 (i.e., the power coupling device obtained by inserting windings and assembling mirror-image half-couples such as that shown in FIG. 18 is shown as would be seen if viewed in such fashion). Although the planar configuration is shown in FIG. 19, similar behavior will be exhibited by rotary transformers having cylindrical or conical configuration where core(s) is/are made up of multiplicities of such ferrite core segments or there is otherwise interruption of axisymmetry. At FIG. 19, insets i, ii, and iii show how magnetic flux lines bridge the core airgap at three different angular positions assumed by the rotary transformer during operation of the power coupling device.

At FIG. 19, it can be seen how lines of magnetic flux bridging core airgap 302 might alternately become aligned and misaligned ("misalignment" here meaning that lines of magnetic flux mutually linking primary and secondary cores no longer lie in meridional planes, e.g., no longer lie in planes of toroid minor circles) during rotation of the power coupling device due to presence of spaces between mutually adjacent ferrite core segments making up respective cores 330, 380. That is, as indicated in the description with reference to FIGS. 17 and 18, any of the cores in the embodiments shown in the drawings may comprise a multiplicity of core segments, e.g., C-core ferrite segments, so as to, for example, collectively approximate substantially annular and/or semitoroidal configurations. To the extent that use of such an arrangement of mutually adjacent core segments results in a segmented core that deviates from axisymmetry, this can be expected to cause misalignment of magnetic flux loops as, say, high-reluctance regions on one side of the core airgap alternately come into alignment with high-and low-reluctance regions on the other side of the core airgap during operation of the power coupling device, causing flux loops to, for example, intermittently be confined and then not be confined to planes of toroid minor circles or to meridional planes.

Where available of course, it may be preferred to use wedge-shaped core segments of appropriate dimensions rather than segments having rectangular profile when fabricating cores from multiplicities of core segments so as to reduce the size of the spaces therebetween which cause the flux line misalignment shown in FIG. 19. Furthermore, given the same C-core dimensions, for example, the cylindrical configuration shown in FIG. 17 might be expected to exhibit less flux line misalignment than the planar configuration shown in FIG. 18 because of the fact that pie-shaped wedging of core segments, occurring as an artifact of use of core segments having rectangular profile to approximate a curved surface, is less pronounced for the cylindrical configuration shown in FIG. 17. But where, e.g., for reasons of manufacturability, an integral number of core segments is used, core segments are all of identical dimensions, core segments having rectangular profile are used to approximate a curved surface, or for other such reasons there are spaces between mutually adjacent core segments on each side (i.e., primary and secondary sides) of the rotary transformer, such spaces alternately lining up with core segments and with spaces therebetween present on the other side (e.g., secondary side) of the rotary transformer as a result of relative rotation during operation of the power coupling device, distortion of magnetic flux lines can increase RF emission because such distortion may interfere with operation of the shield as described above with reference to FIG. 5 through 11. Furthermore, this flux line distortion effect may be made much more pronounced when the space between core segments is on the order of or greater than the size, in the direction of rotation, of the core segment itself, as would be the case were a core segment completely omitted, for example (this is the reason for the cautionary statement at the description with reference to FIG. 17 to the effect that although ferrite core segments are shown in FIG. 17 as being omitted in the regions where winding leads 210 and 260 enter and exit the respective cores, this is only for convenience of illustration, it being preferred that there be minimal interruption in the axisymmetry of the ferrite core segment arrangement).

To minimize such misalignment of magnetic flux loops, and thus improve operation of the shield as described above with reference to FIGS. 5 through 18, it is therefore preferred, where core(s) comprise multiplicity or multiplicities of core segments, that choice of core segments and arrangement of those core segments be such that the space intervening between any two mutually adjacent segments in the circumferential direction (direction of rotation) is not more than the width of any one of the core segments in the circumferential direction; it is more preferred that such space be not more than one-half of the width of any one of the core segments in the circumferential direction.

Figure 20:
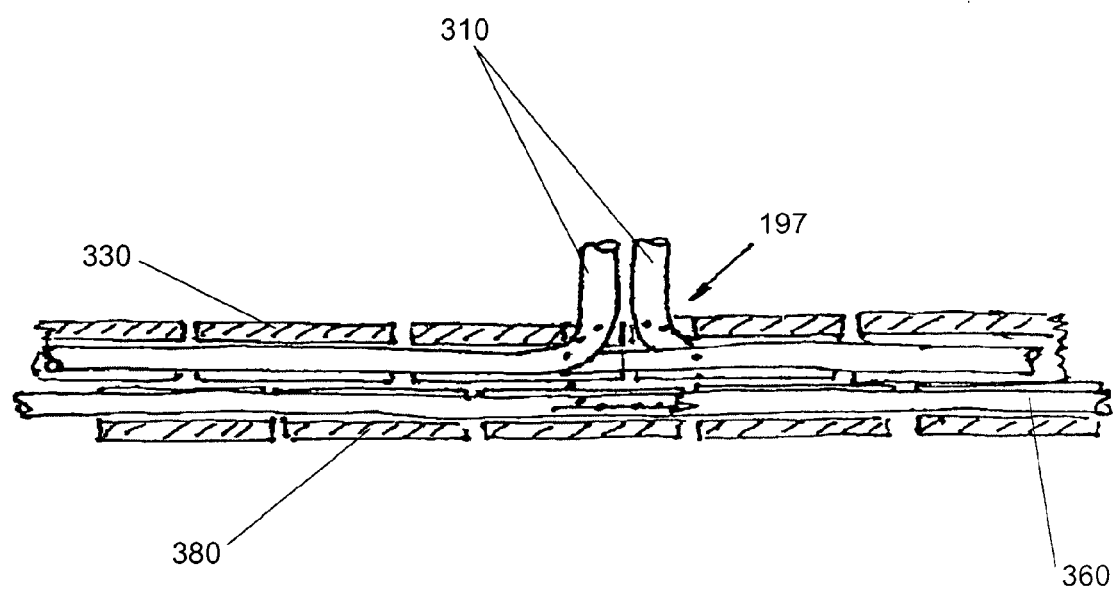
FIG. 20, in which a power coupling device of planar configuration having mutually opposed cores respectively made up of multiplicities of ferrite core segments 330, 380 as shown in FIG. 18 is drawn in cutaway fashion to reveal the windings 310, 360 therewithin as would be seen if viewed edge-on within the plane of the paper at FIG. 18, shows how a virtual current loop 197 might be formed where winding lead wires enter and exit a core recess.

Referring now to FIG. 20, another potential loss of axisymmetry can arise, for example, where it is necessary to bring the leads for windings 310, 360 into and out of the core recesses. At FIG. 20, a power coupling device of planar configuration having mutually opposed cores respectively made up of multiplicities of core segments 330, 380 as shown in FIG. 18 is drawn in cutaway fashion to reveal the windings 310, 360 therewithin as would be seen if viewed edge-on within the plane of the paper at FIG. 18 (i.e., the power coupling device obtained by inserting windings and assembling mirror-image half-couples such as that shown in FIG. 18 is shown as would be seen if viewed in such fashion). Although the planar configuration is shown in FIG. 20, similar behavior will be exhibited by rotary transformers having cylindrical or conical configuration where lead wires for winding(s) enter and exit core recess(es).

As indicated above, it is generally not preferred that core segment(s) be omitted, or that spacing between mutually adjacent core segments be significantly increased, to make room for winding lead wires, since doing so will tend to interrupt core axisymmetry and potentially increase misalignment of magnetic flux lines such that a situation similar to that shown in FIG. 19 could occur.

FIG. 20 also indicates another potential contribution to magnetic flux line misalignment, and therefore to possible interference with preferred shield operation and/or potential increased RF emission. That is, at FIG. 20, it can be seen how a virtual current loop 197 might be formed where winding lead wires 310 enter and exit a core recess in such fashion as to form two legs of a more or less equilateral triangle, the third leg of which may be formed by presence of a mutually opposed winding 360, the opposed winding 360 thus potentially aggravating the situation with respect to formation of such a virtual current loop 197. As the magnetic fields of the paired winding lead wires tend to mutually cancel where those lead wires can be paired close together (particularly when those lead wires are twisted and are collectively shielded), note that it is where the paired lead wires diverge from one another (as can be seen at FIG. 20) that such a virtual current loop 197 will generally form, the magnitude of the problem represented by the virtual current loop 197 generally increasing with the size of the more or less equilateral triangle formed by those diverging lead wires. Whereas in an idealized rotary transformer having a single-turn winding such as that depicted at FIGS. 14 and 15 it might be possible to cause the winding leads to enter and exit the core recess in perfect right-angle fashion such that no space intervenes therebetween, in practical embodiments it may be difficult to avoid formation of such a virtual current loop 197. Note that the current flowing in such a virtual current loop 197 will correspond to a current expected based on the full power being transferred by the power coupling device and not just to the magnetization current; that is, although the current flowing in such a virtual current may be a small proportion of the current corresponding to the power transferred by the power coupling device, where a large amount of power is being transferred across the power coupling device, the current flowing in such a virtual current loop 197 may be quite large. Moreover, as the magnetic field produced by such a virtual current loop 197 will not in general be aligned such that lines of magnetic flux attributable thereto lie within meridional planes, such misalignment of magnetic flux can therefore have significant deleterious effect on operation of the shield.

Figure 21:
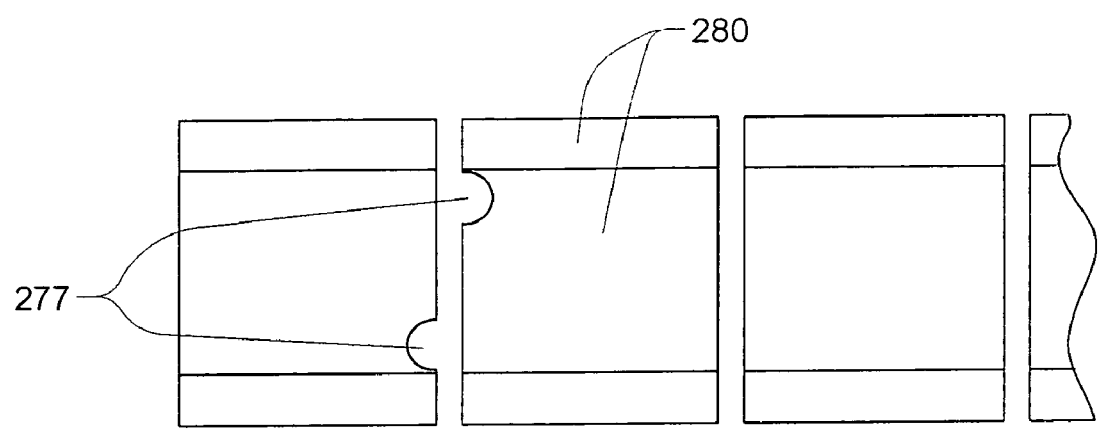
FIG. 21, in which ferrite core segments 280 making up a portion of the inner core of the power coupling device having cylindrical configuration shown in FIG. 17 are drawn as would be seen if viewed edge-on within the plane of the paper at FIG. 17, shows a pair of passageways 277 permitting passage of winding lead wires and disposed in kitty-corner fashion on mutually adjacent core segments.

To avoid the need to omit core segment(s) and/or increase spacing between mutually adjacent core segment(s) for passage of winding lead wire(s), it is therefore preferred in one or more embodiments of the present invention, where a multiplicity of core segments are used to approximate axisymmetric core(s), that core segment(s) be provided with passageway(s) permitting passage therethrough of winding lead wire(s). Moreover, to minimize formation of virtual current loops as described above with reference to FIG. 20, and thus improve operation of the shield as described above with reference to FIGS. 5 through 18, it is preferred in one or more embodiments of the present invention that lead wires of winding(s) pass through core(s) in such fashion and at such location(s) as will substantially eliminate or minimize formation of such virtual current loop(s). For example, core segments 280 having passageways 277 as shown at FIG. 21 might be employed to achieve this twin purpose. At FIG. 21, although notched passageways 277 are shown, there is no particular objection to use of holes or the like as passageways 277.

Referring to FIG. 21, where a multiplicity of commercially available core segments 280 are used to approximate axisymmetric core(s), employment of passageways 277 will make it possible for winding lead wires to enter and exit core recess(es) in such fashion as to not increase spacing between mutually adjacent core segments or otherwise significantly interrupt core axisymmetry. Furthermore, core segments 280 having passageways 277 for lead wires as shown at FIG. 21 may be used to substantially eliminate or minimize formation of virtual current loop(s) by minimizing size of the generally triangular region formed in part by diverging winding leads. Although core segments 280 having passageways 277 are shown for C-core segments forming a single recess for, e.g., a single winding at FIG. 21, it is of course also possible to employ such passageways in the context of E-core segments or other such core segments forming multiple recesses for, e.g., multiple-turn windings (e.g., FIG. 22 shows a three-turn winding in each recess formed by mutually adjacent E-core segments), in which case core segments having passageways for winding lead wires may be used to substantially eliminate or minimize formation of virtual current loop(s) by minimizing size of the generally triangular region formed in part by diverging winding leads while at the same time accommodating intervening wire diameters, as described below with reference to FIG. 22.

At FIG. 21, ferrite core segments 280 making up a portion of the inner core of the power coupling device having cylindrical configuration shown in FIG. 17 are drawn as would be seen if viewed edge-on within the plane of the paper at FIG. 17. Here, a preferred embodiment in which a pair of passageways 277 permitting passage of winding lead wires are disposed in kitty-corner fashion on mutually adjacent core segments is shown. Although FIG. 21 shows a pair of passageways 277 disposed in kitty-corner fashion on mutually adjacent core segments, similar effect may be obtained where such passageways are not disposed in kitty-corner fashion on mutually adjacent core segments but are instead disposed on the same core segment at diagonally opposed locations at either end in the direction in which the winding is wound within the core recess; i.e., such as would be the case if the passageway 277 at the leftmost core segment in FIG. 21 were instead disposed in the corresponding location on the core segment in the central portion of FIG. 21 so as to cause both passageways 277 to be on the same core segment. Although core segments used to approximate cores for the cylindrical configuration happen to be shown in FIG. 21, similar structure and operation will be possible for rotary transformers having planar or conical configuration where core(s) is/are made up of multiplicities of such ferrite core segments; furthermore, although C-core segments happen to be shown in FIG. 21, similar structure and operation will be possible for E-core segments or segments of any other suitable cross-sectional profile (e.g., E-core segments happen to be shown in FIG. 22, where routing of a winding and the lead wires for same is shown).

Figure 22:
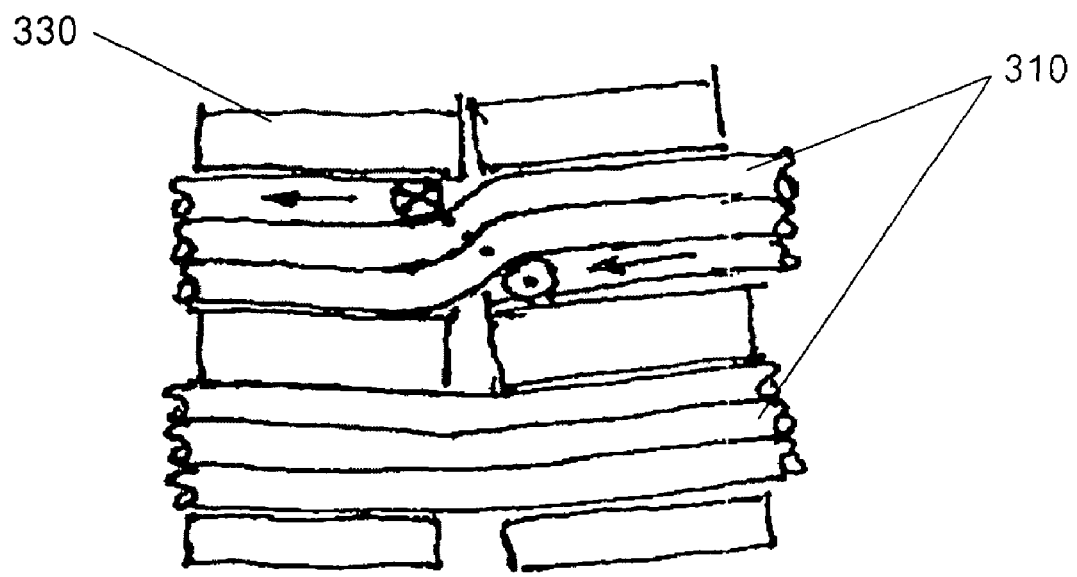
FIG. 22, in which core segments 330 making up a portion of the core of one half-couple of the power coupling device having planar configuration shown in FIG. 18 are drawn in side view as at FIG. 18 except that the core at FIG. 22 employs E-core segments instead of the C-core segments employed in the core at FIG. 18, shows how a three-turn winding 310 (here, referring to the winding 310 in the upper portion of the drawing) might be routed along a core recess such that the winding lead wires enter and exit the core recess by way of passageways disposed in kitty-corner fashion on mutually adjacent core segments 330.

Referring to FIG. 22, here, core segments 330 making up a portion of the core of one half-couple of the power coupling device having planar configuration shown in FIG. 18 are drawn in side view as at FIG. 18 except that the core at FIG. 22 employs E-core segments instead of the C-core segments employed in the core at FIG. 18. At FIG. 22, it can be seen how a three-turn winding 310 in one of the recesses (here, referring to the recess in the upper portion of the drawing) of a core made up of a multiplicity of E-core ferrite segments might be routed along that recess and might be made to pass through passageways disposed in kitty-corner fashion on mutually adjacent core segments 330 as shown in FIG. 21 to emerge from the back faces of such mutually adjacent core segments 330 in the manner shown in FIG. 20. Diagonal or kitty-corner arrangement of passageways in the case of the three-turn winding shown in FIG. 22 facilitates routing of the winding as it is wound in the recess, especially where allowance must be made to accommodate intervening winding wire diameter(s) where the winding must bend to conform and make a "change of lanes" as each turn brings the winding into the vicinity of where the lead wires enter and exit the recess (e.g., at FIG. 22, distance between passageways must be sufficient to allow two wire diameters to intervene between locations where lead wires enter and exit the recess).

With combined reference to FIGS. 20 and 21, where passageway(s) 277 are employed for passage of winding lead wire(s) therethrough as described above, it is preferred at such time that passageway(s) 277 be disposed on core segment(s) (e.g., core segments 330 at FIG. 20 or core segments 280 at FIG. 21) at such location(s) and in such manner as to not substantially alter reluctance of the path taken by magnetic lines of flux therethrough during operation of the power coupling device. That is, reluctance of ferrite being, for example, 50 to 100 times less than reluctance of air, flux line density will generally be highest near the core airgap; and furthermore, as shielding is especially sensitive to flux line geometry in the vicinity of fringing fields where magnetic flux escapes from the core airgap, it is preferred that in forming hole(s), notch(es), or the like to achieve such passageway(s) 277, no material be removed from core segment surfaces that face the airgap; i.e., it is preferred that the core-airgap interface be smooth and uniform, and that there be no mechanical omission, interruption, or disturbance of the core-airgap interface. It is further preferred that such passageway(s) 277 be present at location(s) on, say, the back face of the core segment, or at other such location(s) relatively distant from the core airgap, where absence of core material will have little adverse effect on the magnetic flux lines that bridge the airgap.

At FIG. 21, note that passageways 277 are present at the back face of the core segments 280, away from surfaces serving as pole faces (core-airgap interfaces) during operation of the power coupling device. Furthermore, at FIGS. 20 through 22, whereas passageway(s) 277 are present only where needed, i.e. only where winding lead wires actually pass through core material, since presence of passageway(s) 277 at core segment back face(s) or other such preferred location(s) safely away from core airgap(s) significantly reduces adverse effect of passageway(s) 277 on the magnetic path taken by magnetic flux lines during operation of the power coupling device, to reduce cost, improve manufacturability, and so forth, there is no particular objection to providing such passageway(s) 277 on all core segments making up the core(s) and not just on core segment(s) at which winding lead wires actually pass therethrough.

As described above, it is preferred that arrangement of windings and/or distribution of reluctance-lowering material at cores be such as to align magnetic flux such that magnetic flux loops lie in meridional planes, e.g., planes of minor circle(s) where the overall axisymmetric structure is more or less toroidal. It is furthermore preferred, especially where core(s) comprise a multiplicity of core segments, that there be minimal interruption to axisymmetry, e.g., due to arrangement, including spacing, of core segments, or due to manner in which winding lead wire(s) enter and/or exit core recess(es); e.g., passageway(s) are preferably employed. It is furthermore preferred that winding lead wire(s), for example, pass through core(s) in such fashion and at such location(s) as will substantially eliminate or minimize formation of virtual current loop(s). For effective shielding as described above with reference to FIGS. 5 through 18, it is preferred in one or more embodiments of the present invention that misaligned magnetic flux including that due to fringing fields and virtual current loops be not more than $\frac{1}{100}$th of total magnetic flux linking the cores during operation of the power coupling device; it is more preferred that such misaligned magnetic flux be not more than $\frac{1}{1,000}$th of total magnetic flux linking the cores during operation of the power coupling device; and it is still more preferred that such misaligned magnetic flux be not more than $\frac{1}{10,000}$th of total magnetic flux linking the cores during operation of the power coupling device.

Note that where fractional-turn windings are employed, to avoid a situation in which variation in current density at different points along the circumference of the overall axisymmetric structure of the power coupling device causes distortion of magnetic flux lines, i.e., causes loops of magnetic flux linking respective cores to deviate from meridional planes, it is preferred that such fractional turns be arranged so as to collectively constitute a single full turn (e.g., three fractional turns, each of which occupies one-third of the circumference of a toroid major circle, might be employed), and it is furthermore preferred during operation of the shielded power coupling device that current be made to flow through all fractional turns in such fashion as to achieve a more or less uniform magnetic field at substantially all locations around the circumference of the overall axisymmetric structure.

Any suitable material and assembly method may be used for the windings, cores, and shield(s) of the shielded power coupling device. Wire(s), e.g., Litz wire, wound around core(s) might typically serve as winding(s), but any suitable material and manufacturing method, including molding, casting, extrusion, and so forth might also be employed. Although practical examples have been described in which large-diameter ferrite cores were built up from multiplicities of core segments, the present invention is not limited thereto, it being possible to employ cast, molded, extruded, or like core elements where available. Furthermore, although ferrite has been mentioned as one specific example of a preferred core material, the present invention is not limited thereto, it being possible to use silicon iron, nickel iron alloy, stainless steel, cobalt iron alloy, or any other suitable material. Although aluminum has been mentioned as one specific example of a preferred shield material, the present invention is not limited thereto, it being possible to alternatively or additionally employ other metal(s), other electrically conductive material (s), and/or any other suitable material(s) for same. Those skilled in the art will appreciate that the shielded power coupling device may be manufactured in any of a wide variety of ways; as one example, wires serving as windings may be wound within recesses of multiplicities of core segments arranged to approximate axisymmetric structures as described above with reference to FIGS. 17 and 18, such core segments being potted or embedded within, or otherwise held in place relative to, electrically conductive material serving as continuous electrical path(s) around the axis of axisymmetry as described above with reference to FIGS. 5 through 18. At such time, sheet metal, channel or other such extruded stock, or the like might be wrapped in arcuate or helical fashion and held together with electrically conductive epoxy or the like to approximate axisymmetric shield(s) as described above with reference to any of FIGS. 5 through 18. At such time, it is preferred for proper operation of the shield that proper attention be given to arrangement/distribution of core material, core airgap geometry, core segment spacing, passageways for ingress/egress of winding lead wires, and so forth, in order to minimize deviation of the magnetic field from meridional planes during operation of the shielded power coupling device. It is furthermore preferred that proper attention be given to orientation and location of shield airgap(s), to arrangement of electrically conductive material within shield (s) for sufficient current-carrying capacity at fringe field canceling zones, to location of such zones relative to fringing fields emanating from core airgap peripheries, to creation of preferably circular electrically continuous path(s) constituting closed electric circuit(s) about the axes of axisymmetry and rotation, and so forth.

Although specific axisymmetric configurations have been discussed and depicted in the drawings, the present invention is not intended to be limited thereto, it being possible, with appropriate modification as necessary, to apply the foregoing description to any suitable axisymmetric configuration. Furthermore, although the terms "axisymmetry," "toroidal," and so forth have been employed to provide a general framework within which to discuss direction of current, magnetic flux lines, and so forth, such framework should not be taken overly literally to mean that axisymmetry or toroidal geometry must be strictly adhered to for benefit to be obtained from the shielded power coupling device of the present invention or that deviation from strict axisymmetry or toroidal geometry would necessarily be outside the scope of the claims; in particular, note that significant deviation from axisymmetry and/or toroidal geometry may be possible, e.g., with respect to shield shape, without necessarily significantly impairing operation of the shielded power coupling device while still remaining within the scope of the claims and/or within the basic parameters set forth for satisfactory shield operation as described, for example, with reference to FIGS. 5 through 22.

Moreover, while at least one shield airgap (including configurations having one large shield airgap as at FIG. 10) will in general be necessary to permit relative movement between half-couples, there is no particular objection to having multiple shield airgap(s) and/or core airgap(s). Furthermore, there is no objection to employing multiple ganged and/or nested sets of half-couples with multiple airgaps therebetween to allow for relative rotation, a few representative examples of which are shown in FIG. 23.

Figure 23:
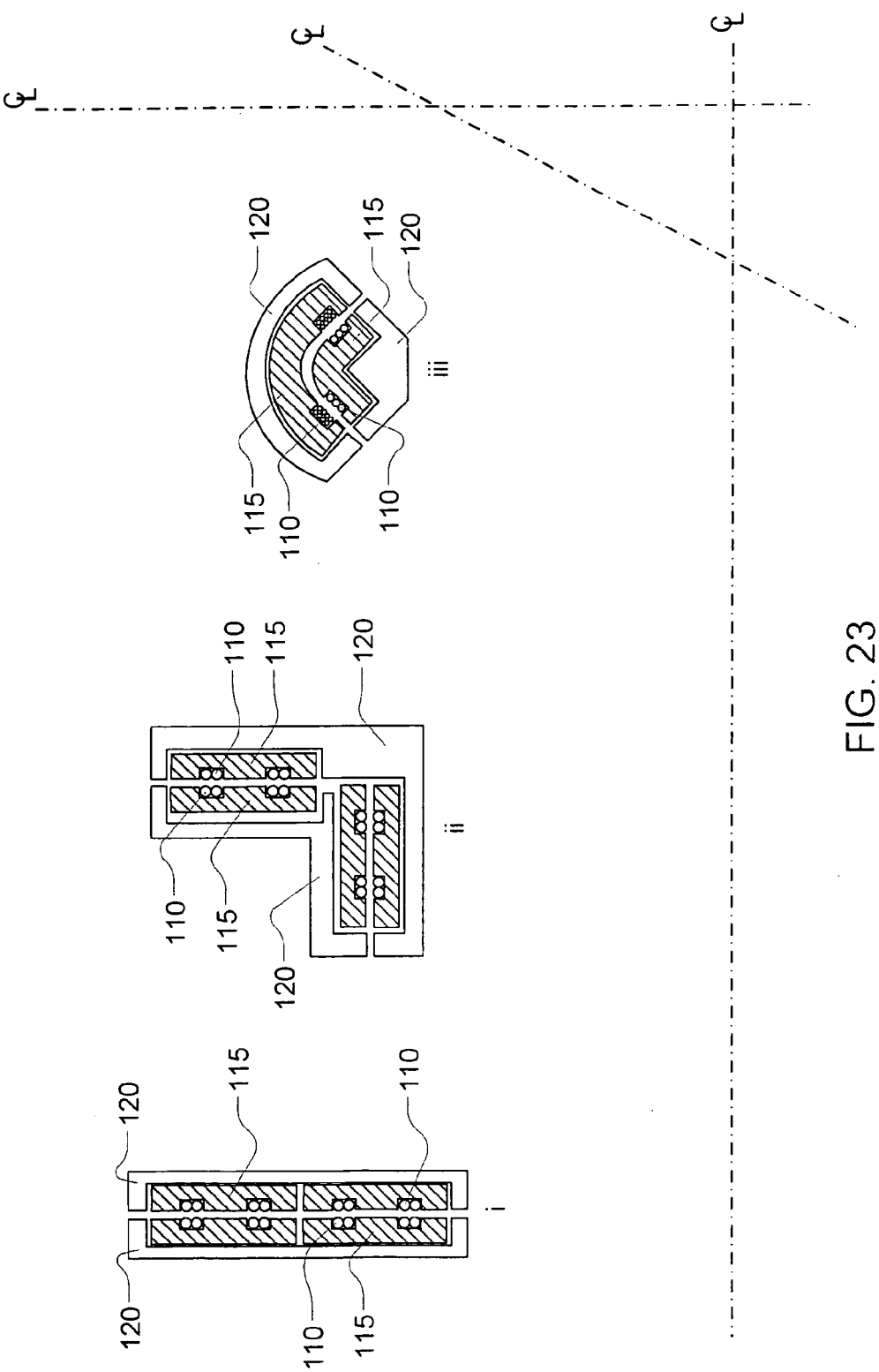
FIG. 23 shows several representative cross-sectional profiles that might be used to generate axisymmetric solids of revolution to which the structure of rotary transformers in accordance with embodiments of the present invention might conform, this drawing in particular demonstrating how multiple ganged or nested sets of rotary transformer half-couples might be incorporated into various integral structures.

FIG. 23 shows several representative cross-sectional profiles that might be used to generate axisymmetric solids of revolution to which the structure of rotary transformers in accordance with embodiments of the present invention might conform, this drawing in particular demonstrating how multiple ganged or nested sets of rotary transformer half-couples might be incorporated into various integral structures. In the drawing, like-numbered parts have function as described above, except that for convenience no distinction has been made in labeling between stationary and rotating sides (i.e., stationary-side reference numerals have been used for half-couples on both sides notwithstanding the fact that in practice one side of each such pair of half-couples would typically serve as rotary transformer primary side while the other side of same would typically serve as rotary transformer secondary side). Each of the three configurations labeled i through iii at FIG. 23 can be expected to provide adequate shielding when used as cross-sectional profile to generate a more or less axisymmetric solid of revolution therefrom. In the drawing, horizontal, vertical, and oblique center lines have been drawn in schematic fashion to indicate that the axis of revolution about which such a cross-sectional profile is swept to obtain the more or less axisymmetric rotary transformer structure of various embodiments of the present invention should lie outside of the cross-sectional profile but may be at any radius therefrom and at any orientation with respect thereto.

The power coupling device of the present invention may be useful for transmitting power in systems including at least one rotating unit, such as a CT scanner. In systems including a stationary member, and a rotatable member coupled to the stationary member, the power coupling device of the present invention may transmit power from the power source to either the stationary member or the rotatable member or both. For example, the stationary member may be the stationary gantry in a CT scanner, and the rotatable member may be the rotatable gantry in the CT scanner and may include an x-ray source.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A shielded power coupling device configured to transfer electric power between a stationary subsystem and a rotatable subsystem that is inductively coupled to and arranged in close proximity to the stationary subsystem and that, during operation of the shielded power coupling device, is capable of rotating about an axis of rotation which is also substantially an axis of symmetry for both the stationary subsystem and the rotating subsystem, the shielded power coupling device comprising:
   a) an inductive field generating element capable of converting electric power to an inductive coupling field;
   b) an inductive coupling field receiving element capable of converting the inductive coupling field to electric power;
   c) an inductive coupling efficiency increasing element capable of increasing inductive coupling between the inductive field generating element and the inductive coupling field receiving element, wherein the inductive coupling efficiency increasing element comprises a primary core and a secondary core separated by a core airgap, and wherein the inductive field generating element and the inductive coupling field receiving element are disposed in mutually opposed core recesses of the primary core and secondary core, respectively; and
   d) shielding peripheral to the inductive coupling efficiency increasing element that is capable of substantially eliminating leakage of electromagnetic radiation from the shielded power coupling device when the shielded power coupling device is operated at power levels exceeding 2.5 kW, wherein the shielding comprises first and second shields separated by a shield airgap, wherein the primary and secondary cores are disposed in mutually opposed shield recesses of the first and second shields, respectively, and wherein the shield airgap is greater than the core airgap.

2. A shielded power coupling device transferring electric power between a stationary member and a rotating member, the shielded power coupling device comprising:
 a) a reluctance-decreasing primary core defining a first primary core recess;
 b) a reluctance-decreasing secondary core disposed adjacent the primary core and defining a first secondary core recess, the primary core and the secondary core being arranged so as to form a core airgap therebetween permitting relative rotation of the primary core and the secondary core about an axis of rotation;
 c) a first electrically conductive primary winding disposed substantially within the first primary core recess;
 d) a first electrically conductive secondary winding disposed substantially within the first secondary core recess; and
 e) a shield comprising first and second shields separated by a shield airgap, wherein the primary and secondary cores are disposed in mutually opposed shield recesses of the first and second shields, respectively, and wherein the shield airgap is greater than the core airgap;
 f) wherein a first primary electric current flowing through the first primary winding produces a first secondary electric current flowing through the first secondary winding, creating a fringing field at the periphery of the core airgap; and
 g) wherein the shield substantially cancels the fringing field when the shielded power coupling device is operated at power levels exceeding 2.5 kW.

3. A shielded power coupling device in accordance with claim 2 wherein the shield forms at least one substantially continuous electrical path constituting a closed electric circuit around the axis of rotation.

4. A shielded power coupling device in accordance with claim 2 wherein the shield forms at least one substantially circular electrical path constituting a closed electric circuit around the axis of rotation.

5. A shielded power coupling device in accordance with claim 2 wherein the shield comprises electrically conductive material in at least one ring-like band adjacent to and alongside the core airgap.

6. A shielded power coupling device in accordance with claim 2 wherein the shield has electrically conductive material at such locations and in such electrical conductivity or conductivities and thickness or thicknesses as is sufficient to support electric currents capable of inducing a magnetic field that is capable of substantially canceling the fringing field.

7. A shielded power coupling device in accordance with claim 2 wherein, during cancellation of the fringing field by the shield, an image current flowing in the shield produces a magnetic field that is capable of canceling the fringing field.

8. A shielded power coupling device in accordance with claim 7 wherein the net image current in the shield flows substantially circumferentially about the axis of rotation during cancellation of the fringing field by the shield.

9. A shielded power coupling device in accordance with claim 7 wherein the overall configuration of the shielded power coupling device is substantially axisymmetric, and the net image current in the shield flows substantially circumferentially about the axis of axisymmetry during cancellation of the fringing field by the shield.

10. A shielded power coupling device in accordance with claim 7 wherein the overall configuration of the shielded power coupling device is substantially toroidal, and the net image current in the shield flows substantially along a circle coaxial with a major circle thereof during cancellation of the fringing field by the shield.

11. A shielded power coupling device in accordance with claim 2 wherein, during cancellation of the fringing field by the shield, a net image current flows in the shield that is substantially equal in magnitude but opposite in sign to the net electric current flowing through the windings.

12. A shielded power coupling device in accordance with claim 2 wherein the shield is a single-part shield having a shield airgap that is substantially nonadjacent with respect to the core airgap.

13. A shielded power coupling device in accordance with claim 12 wherein, as measured in a direction perpendicular to an imaginary surface bounding the volume of space swept out by the core airgap during operation of the shielded power coupling device, the shield airgap is not less than three core airgap thicknesses from the core airgap.

14. A shielded power coupling device in accordance with claim 12 wherein, as measured in a direction perpendicular to an imaginary surface bounding the volume of space swept out by the core airgap during operation of the shielded power coupling device, the shield airgap is not less than five core airgap thicknesses from the core airgap.

15. A shielded power coupling device in accordance with claim 2 wherein thickness of the shield in the region of the core airgap is sufficient to achieve an electrical conductivity equivalent to that of aluminum in a thickness of not less than five core airgap thicknesses.

16. A shielded power coupling device in accordance with claim 2 wherein thickness of the shield in the region of the core airgap is sufficient to achieve an electrical conductivity equivalent to that of aluminum in a thickness of not less than ten core airgap thicknesses.

17. A shielded power coupling device in accordance with claim 2 wherein the shield is a multipartite shield having a shield airgap permitting relative movement during operation of the shielded power coupling device.

18. A shielded power coupling device in accordance with claim 17 wherein the shield airgap is substantially adjacent the core airgap.

19. A shielded power coupling device in accordance with claim 18 wherein thickness of the shield in the region of the core airgap is sufficient to achieve an electrical conductivity equivalent to that of aluminum in a thickness of not less than five core airgap thicknesses.

20. A shielded power coupling device in accordance with claim 18 wherein thickness of the shield in the region of the core airgap is sufficient to achieve an electrical conductivity equivalent to that of aluminum in a thickness of not less than ten core airgap thicknesses.

21. A shielded power coupling device in accordance with claim 18 wherein thickness of the shield in the region of the core airgap is sufficient to achieve an electrical conductivity equivalent to that of aluminum in a thickness of not less than two shield airgap thicknesses.

22. A shielded power coupling device in accordance with claim 18 wherein thickness of the shield in the region of the core airgap is sufficient to achieve an electrical conductivity equivalent to that of aluminum in a thickness of not less than four shield airgap thicknesses.

23. A shielded power coupling device in accordance with claim 2 wherein, during operation of the shielded power coupling device, the net electric current flowing through the windings is substantially zero.

24. A shielded power coupling device in accordance with claim 2 wherein
 a) the primary core further defines a second primary core recess;
 b) the secondary core further defines a second secondary core recess;
 c) the shielded power coupling device further comprises:
  i) a second electrically conductive primary winding disposed substantially within the second primary core recess; and
  ii) a second electrically conductive secondary winding disposed substantially within the second secondary core recess;
 d) wherein a second primary electric current flowing through the second primary winding produces a second secondary electric current flowing through the second secondary winding; and
 e) during operation of the shielded power coupling device, the instantaneous net electric current flowing through the primary windings is substantially zero.

25. A shielded power coupling device in accordance with claim 2 wherein the secondary core recesses are disposed opposite the primary core recesses and are spaced apart therefrom.

26. A shielded power coupling device in accordance with claim 2 wherein the recesses are substantially annular.

27. A shielded power coupling device in accordance with claim 2 wherein the cores are of substantially semitoroidal configuration.

28. A shielded power coupling device in accordance with claim 2 wherein the primary core and the secondary core are of substantially axisymmetric configuration with mutually collinear axes of symmetry thereof being collinear with the axis of rotation.

29. A shielded power coupling device in accordance with claim 2 wherein, during operation of the shielded power coupling device, the core airgap sweeps out a volume in space of configuration substantially corresponding to one or more species selected from among the group consisting of planar configuration, cylindrical configuration, and conical configuration.

30. A shielded power coupling device in accordance with claim 2 wherein a volume in space swept out by the core airgap during operation of the shielded power coupling device is of substantially planar configuration and intervenes axially with respect to the axis of rotation between the primary core and the secondary core.

31. A shielded power coupling device in accordance with claim 2 wherein a volume in space swept out by the core airgap during operation of the shielded power coupling device is of substantially cylindrical configuration and intervenes radially with respect to the axis of rotation between the primary core and the secondary core.

32. A shielded power coupling device in accordance with claim 2 wherein a volume in space swept out by the core airgap during operation of the shielded power coupling device is of substantially conical configuration and intervenes both axially and radially with respect to the axis of rotation between the primary core and the secondary core.

33. A shielded power coupling device in accordance with claim 2 wherein the shield is of substantially axisymmetric configuration with axis of symmetry thereof being collinear with the axis of rotation.

34. A shielded power coupling device in accordance with claim 2 wherein loops of magnetic flux linking the primary core and the secondary core during operation of the shielded power coupling device lie in substantially meridional planes with respect to the axis of rotation.

35. A shielded power coupling device in accordance with claim 2 wherein mutually opposed core surfaces separated by the core airgap are substantially smooth, substantially mutually parallel, and substantially normal to the predominant direction of magnetic flux lines bridging the mutually opposed core surfaces during operation of the shielded power coupling device.

36. A shielded power coupling device in accordance with claim 2 wherein the overall configuration of the shielded power coupling device is substantially toroidal, loops of magnetic flux linking the primary core and the secondary core during operation of the shielded power coupling device lying substantially in planes of minor circles thereof.

37. A shielded power coupling device in accordance with claim 2 wherein, as viewed in a meridional section with respect to the axis of rotation, except for lines of magnetic flux that are responsible for presence of the fringing field, lines of magnetic flux linking the primary core and the secondary core during operation of the shielded power coupling device bridge the core airgap so as to be normal to an imaginary surface bounding a volume in space swept out by the core airgap during operation of the shielded power coupling device.

38. A shielded power coupling device in accordance with claim 2 wherein the primary core and the secondary core each comprise a plurality of core segments arranged in substantially mutually adjacent fashion so as to collectively approximate a substantially axisymmetric configuration.

39. A shielded power coupling device in accordance with claim 38 wherein at each the primary core and the secondary core, the core segments are arranged such that space intervening between mutually adjacent segments in a circumferential direction with respect to the axis of rotation is not more than the width of one of the core segments in the circumferential direction.

40. A shielded power coupling device in accordance with claim 38 wherein at each the primary core and the secondary core, the core segments are arranged such that space intervening between mutually adjacent segments in a circumferential direction with respect to the axis of rotation is not more than one-half of the width of one of the core segments in the circumferential direction.

41. A shielded power coupling device in accordance with claim 38 wherein at least one of the core segments has a passageway permitting passage therethrough of a lead wire for at least one of the windings.

42. A shielded power coupling device in accordance with claim 41 wherein the passageway is disposed on the core segment at such location and in such manner as to not substantially alter reluctance of the path taken by magnetic lines of flux therethrough during operation of the power coupling device.

43. A shielded power coupling device in accordance with claim 41 wherein the passageway is disposed on the core segment at a location other than a core-airgap interface.

44. A shielded power coupling device in accordance with claim 41 wherein the passageway is disposed on the core segment at a location on the core segment which is a back face that is a farthest surface thereof from the core airgap.

45. A shielded power coupling device in accordance with claim 38 wherein passageways permitting passage of at least one pair of lead wires for at least one of the windings are disposed in kitty-corner fashion on mutually adjacent core segments.

46. A shielded power coupling device in accordance with claim 38 wherein passageways permitting passage of at least one pair of lead wires for at least one of the windings are disposed on the same core segment at diagonally opposed locations at either end thereof in the direction in which at least one of the windings is wound within at least one of the recesses.

47. A shielded power coupling device in accordance with claim 2 wherein lead wires of the first primary winding pass through the primary core in such fashion and at such locations as will substantially minimize magnetic field of a virtual current loop formed in part by the first primary winding lead wires.

48. A shielded power coupling device in accordance with claim 2 wherein lead wires of the secondary winding pass through the first secondary core in such fashion and at such locations as will substantially minimize magnetic field of a virtual current loop formed in part by the first secondary winding lead wires.

49. A shielded power coupling device in accordance with claim 2 wherein misaligned magnetic flux including that due to the fringing field and any virtual current loops is not more than 1/100th of total magnetic flux linking the cores during operation of the shielded power coupling device.

50. A shielded power coupling device in accordance with claim 2 wherein misaligned magnetic flux including that due to the fringing field and any virtual current loops is not more than 1/1,000th of total magnetic flux linking the cores during operation of the shielded power coupling device.

51. A shielded power coupling device in accordance with claim 2 wherein misaligned magnetic flux including that due to the fringing field and any virtual current loops is not more than 1/10,000th of total magnetic flux linking the cores during operation of the shielded power coupling device.

52. A shielded power coupling device comprising:
   a) a primary winding
      i) having substantially axisymmetric configuration, and
      ii) defining a circumferential direction;
   b) a secondary winding
      i) having substantially axisymmetric configuration,
      ii) substantially concentric with the primary winding,
      iii) capable of rotating relative to the primary winding, and
      iv) inductively coupled to the primary winding;
   c) an inductive coupling efficiency increasing element comprising a primary core and a secondary core separated by a core airgap, and wherein the primary winding and the secondary winding are disposed in mutually opposed core recesses of the primary core and secondary core, respectively; and
   d) a shield having at least one shield airgap permitting relative rotation between the primary winding and the secondary winding, wherein the shield airgap is greater than the core airgap, wherein the shield is operative to substantially eliminate leakage of electromagnetic radiation from the shielded power coupling device when the shielded power coupling device is operated at power levels exceeding 2.5 kW;
   e) wherein the shield supports flow of electric current in the circumferential direction.

53. A shielded power coupling device comprising:
   a) at least two substantially arcuate windings arranged in mutually radially and/or axially displaced fashion relative to an approximate major circle of an imaginary toroid, wherein the at least to arcuate windings include a primary winding and a secondary winding; and
   b) an inductive coupling efficiency increasing element comprising a primary core and a secondary core separated by a core airgap, wherein the primary winding and the secondary winding are disposed in mutually opposed core recesses of the primary core and secondary core, respectively;
   c) at least one electrically conductive shield encircling and/or encircled by the windings, wherein the shield includes at least one shield airgap, and wherein the shield airgap is greater than the core airgap;
   d) wherein, upon application of an alternating electric current to at least one of the windings, flux lines linking at least a portion of the windings lie substantially in planes of minor circles of the imaginary toroid; and,
   e) the shield supports flow of electric current along a direction of a circle coaxial with the major circle of the imaginary toroid sufficient to induce a magnetic field capable of substantially canceling a magnetic field due to a net electric current flowing in the windings upon application of the alternating electric current to at least one of the windings when the shielded power coupling device is operated at power levels exceeding 2.5 kW.

54. A shielded power coupling device transferring electric power between a stationary subsystem and a rotatable subsystem that is inductively coupled to and arranged in close proximity to the stationary subsystem and that, during operation of the shielded power coupling device, is capable of rotating about an axis of rotation which is also substantially an axis of symmetry for both the stationary subsystem and the rotating subsystem, the shielded power coupling device comprising:
   a) inductive field generating means for converting electric power to an inductive coupling field;
   b) inductive coupling field receiving means for converting the inductive coupling field to electric power;
   c) inductive coupling efficiency increasing means for increasing inductive coupling between the inductive field generating means and the inductive coupling field receiving means, wherein the inductive coupling efficiency increasing element comprises a primary core and a secondary core separated by a core airgap, and wherein the inductive field generating element and the inductive coupling field receiving element are disposed in mutually opposed core recesses of the primary core and secondary core, respectively; and
   d) shielding means peripheral to the inductive coupling efficiency increasing means for substantially eliminating leakage of electromagnetic radiation from the shielded power coupling device when the shielded power coupling device is operated at power levels exceeding 2.5 kW, wherein the shielding means comprises first and second shields separated by a shield airgap, wherein the primary and secondary cores are disposed in mutually opposed shield recesses of the first and second shields, respectively, and wherein the shield airgap is greater than the core airgap.

55. A flux-aligning core set for use with two or more windings, including a primary winding and a secondary winding, and one or more shields, the core set comprising:
   a) a plurality of flux-aligning core segments, each of which,
      i) is composed of one or more substances having reluctance lower than that of air, and
      ii) has at least two arm-like members;
   b) wherein the plurality of flux-aligning core segments are arranged in substantially axisymmetric fashion such that i) at least one of the winding or windings can be routed along one or more circumferentially oriented cradle-like recesses formed by cooperation of at least two of the two or more arm-like members of each of at least a portion of the plurality of flux-aligning core segments; and ii) when at least two of the two or more arm-like members of each of at least a portion of the plurality of flux-aligning core segments are arranged in mutual opposition across a core airgap with at least two arm-like members of each of at least a portion of a counterpart plurality of core segments of a counterpart core set that is substantially a reflection of the flux-aligning core set across the airgap, at least a portion of the flux-aligning core segments and at least a portion of the counterpart core segments cooperate to complete or lower reluctance of a multiplicity of magnetic paths,
1) passing through the flux-aligning core set and the counterpart core set to bridge the airgap, and
2) substantially lying in meridional planes relative to the axis of axisymmetry; and c) a shield having at least one shield airgap permitting relative rotation between the primary winding and the secondary winding, wherein the shield airgap is greater than the core airgap, wherein the shield is operative to substantially eliminate leakage of electromagnetic radiation from the shielded power coupling device when the shielded power coupling device is operated at power levels exceeding 2.5 kW.

56. A passage-containing core segment composed of one or more substances having reluctance lower than that of air and comprising:

a) two or more passages permitting passage of two or more windings therethrough; and b) two or more arm-like members creating one or more cradle-like recesses therebetween along which at least one of the windings can be routed;

c) wherein at least one of the passage or passages is disposed on the passage-containing core segment in at least one location such that, when at least two of the two or more arm-like members of the passage-containing core segment are arranged in mutual opposition across a core airgap with at least two arm-like members of a first counterpart core segment that is substantially a reflection of the passage-containing core segment across the airgap, reluctance of a magnetic path passing through the passage-containing core segment and the first counterpart core segment to bridge the airgap is not substantially different than what the reluctance of the magnetic path would be were there no passage in the passage-containing core segment; and d) a shield having at least one shield airgap permitting relative rotation between a primary winding and a secondary winding of the two or more windings, wherein the shield airgap is greater than the core airgap, wherein the shield is operative to substantially eliminate leakage of electromagnetic radiation from the shielded power coupling device when the shielded power coupling device is operated at power levels exceeding 2.5 kW.

57. A system including a shielded inductive power coupling device, the system comprising:

a) a stationary member;
b) a rotatable member inductively coupled to the stationary member;
c) a power source; and
d) a shielded inductive power coupling device responsive to the power source and capable of transmitting power from the power source to at least one of the stationary member and the rotatable member, the inductive power coupling device comprising:
  i) a primary reluctance-decreasing core defining a primary core recess;
  ii) a secondary reluctance-decreasing core defining a secondary core recess and disposed adjacent the primary core;
  iii) a primary electrically conductive winding disposed within the primary core recess;
  iv) a secondary electrically conductive winding disposed within the secondary core recess; and
  v) an electrically conductive shield, wherein the shield has at least one shield airgap;
  vi) wherein the primary and secondary cores are arranged so as to form a core airgap therebetween permitting relative rotation of the cores about an axis of rotation, wherein the shield airgap is greater than the core airgap;
  vii) a primary electric current flowing through the primary winding produces a secondary electric current flowing through the secondary winding, creating a fringing field at the periphery of the core airgap; and
  viii) the shield is operative to substantially cancel the fringing field when the shielded power coupling device is operated at power levels exceeding 2.5 kW.

58. A system in accordance with claim 57 wherein
a) the system is a CT scanner;
b) the stationary member comprises a stationary gantry in the CT scanner; and
c) the rotatable member includes an x-ray source.

* * * * *